(12) United States Patent
Lu et al.

(10) Patent No.: US 7,582,775 B2
(45) Date of Patent: Sep. 1, 2009

(54) VITAMIN D RECEPTOR MODULATORS

(75) Inventors: Jianliang Lu, Fishers, IN (US); Tainwei Ma, Carmel, IN (US); Sunil Nagpal, Carmel, IN (US); Quanrong Shen, Fishers, IN (US); Alan M. Warshawsky, Carmel, IN (US); Ying Kwong Yee, Carmel, IN (US); Michael John Rupp, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 53 days.

(21) Appl. No.: 10/579,564

(22) PCT Filed: Nov. 16, 2004

(86) PCT No.: PCT/US2004/037181

§ 371 (c)(1),
(2), (4) Date: May 12, 2006

(87) PCT Pub. No.: WO2005/051940

PCT Pub. Date: Jun. 9, 2005

(65) Prior Publication Data

US 2007/0149810 A1 Jun. 28, 2007

Related U.S. Application Data

(60) Provisional application No. 60/523,600, filed on Nov. 20, 2003.

(51) Int. Cl.
C07D 333/00 (2006.01)
(52) U.S. Cl. ....................................................... 549/49
(58) Field of Classification Search ................... 549/49
See application file for complete search history.

(56) References Cited

U.S. PATENT DOCUMENTS

| 5,962,698 | A | * | 10/1999 | Berg et al. | 549/51 |
| 5,985,895 | A | * | 11/1999 | Wermuth et al. | 514/317 |
| 6,110,963 | A | * | 8/2000 | Malamas | 514/443 |
| 6,218,430 | B1 | | 4/2001 | Allegretto et al. | |
| 6,531,459 | B1 | | 3/2003 | Steinmeyer et al. | |
| 2006/0094778 | A1 | | 5/2006 | Nagpal et al. | |
| 2006/0135484 | A1 | | 6/2006 | Nagpal et al. | |
| 2006/0287536 | A1 | | 12/2006 | Dahnke et al. | |
| 2006/0293385 | A1 | | 12/2006 | Gajewski et al. | |
| 2007/0105951 | A1 | | 5/2007 | Gajewski et al. | |
| 2007/0106095 | A1 | | 5/2007 | Lu et al. | |

FOREIGN PATENT DOCUMENTS

| WO | WO 2004/048309 | 6/2004 |
| WO | WO 2005/051893 | 6/2005 |
| WO | WO 2006/069153 | 6/2006 |
| WO | WO 2006/069154 | 6/2006 |

OTHER PUBLICATIONS

Carsten Carlberg & Antonio Mourino: Expert Opinion, vol. 13, No. 6, 2003, pp. 761-772, XP002331659, pp. 763-765.
Masahiko Inouye, Toshiyuki Miyake, Masaru Furusyo, Hiroyuki Nakazumi: "Molecular recognition of beta-Ribofuranosides by synthetic polypyridine_macrocyclic receptors" J.Am. Chem. Soc. vol. 117, 1995, pp. 12416-12425, XP001206518.
Ping Huang, John Ramphal, James Wei, Congxin, Liang, Bahija Jallal, Gerald McMahon and Cho Tang: "Structure-based design and discovery of novel inhibitors of protein tyrosine phosphatases" Bioorganic & Medicinal Chemistry, vol. 11, 2003, pp. 1835-1849, XP001206517.
Boehm, M., "Novel Nonsecosteroidal Vitamin D Mimics Exert VDR-modulating Activities" *Chemistry & Biology*, 1999, 265-275, vol. 6(5).
Nagpal, S. et al. "Vitamin D Analogs: Mechanism of Action of Therapeutic Applications", *Curr. Med. Chem.* 2001, 1661-1679, vol. 8.
Bouillon R., et al. Endocrine Rev. 1995, 200-257, vol. 16.
Swann et al. "Rational Design of Vitamin D3 Analogues Which Selectively Restore Activity to a Vitamin D Receptor Mutant Associated with Rickets" *Org. Lett.* 2002, p. 1863-3866 vol. 4.
Swann et al. "Structure-Based Design of Selective Agonists for a Rickets-Associated Mutant of the Vitamin D Receptor" *J. Am. Chem. Soc.* 2002 13795-13805, vol. 124.

* cited by examiner

*Primary Examiner*—D. Margaret Seaman
*Assistant Examiner*—Nizal S Chandrakumar
(74) *Attorney, Agent, or Firm*—James B. Myers

(57) ABSTRACT

The present invention relates to novel, non-secosteroidal, phenyl-benzothiophene compounds with vitamin D receptor (VDR) modulating activity that are less hypercalcemic than 1α,25 dihydroxy vitamin D3. These compounds are useful for treating bone disease and psoriasis.

17 Claims, No Drawings

VITAMIN D RECEPTOR MODULATORS

This application is submitted as a United States national phase entry, pursuant to 35 U.S.C. §371, of PCT/US2004/037181, filed on 16 Nov. 2004, which claims the benefit of U.S. provisional patent application Ser. No. 60/523,600, filed 20 Nov. 2003, which is incorporated by reference herein.

BACKGROUND OF THE INVENTION

Vitamin $D_3$ Receptor (VDR) is a ligand dependent transcription factor that belongs to the superfamily of nuclear hormone receptors. The VDR protein is 427 amino acids, with a molecular weight of ~50 kDa. The VDR ligand, 1α,25-dihydroxyvitamin D3 (the hormonally active form of Vitamin D) has its action mediated by its interaction with the nuclear receptor known as Vitamin D receptor ("VDR"). The VDR ligand, 1α,25-dihydroxyvitamin D3 (1α,25(OH)$_2$D$_3$) acts upon a wide variety of tissues and cells both related to and unrelated to calcium and phosphate homeostasis.

The activity 1α,25-dihydroxyvitamin D3 in various systems suggests wide clinical applications. However, use of conventional VDR ligands is hampered by their associated toxicity, namely hypercalcemia (elevated serum calcium). Currently, 1α,25(OH)$_2$D$_3$, marketed as Rocaltrol® pharmaceutical agent (product of Hoffmann-La Roche), is administered to kidney failure patients undergoing chronic kidney dialysis to treat hypocalcemia and the resultant metabolic bone disease. Other therapeutic agents, such as Calcipotriol® (synthetic analog of 1α,25(OH)$_2$D$_3$) show increased separation of binding affinity on VDR from hypercalcemic activity.

Chemical modifications of 1α,25(OH)$_2$D$_3$ have yielded analogs with attenuated calcium mobilization effects (R. Bouillon et. al., Endocrine Rev. 1995, 16, 200-257). One such analog, Dovonex® pharmaceutical agent (product of Bristol-Meyers Squibb Co.), is currently used in Europe and the United States as a topical treatment for mild to moderate psoriasis (K. Kragballe et. al., Br. J. Dermatol. 1988, 119, 223-230).

Other Vitamin $D_3$ mimics have been described in the publication, *Vitamin D Analogs: Mechanism of Action of Therapeutic Applications*, by Nagpal, S.; Lu, J.; Boehm, M. F., Curr. Med. Chem. 2001, 8, 1661-1679.

Although some degree of separation between the beneficial action and calcium raising (calcemic) effects has been achieved with these VDR ligands, to date the separation has been insufficient to allow for oral administration to treat conditions such as osteoporosis, cancers, leukemias, and severe psoriasis.

One example of a major class of disorder that could benefit from VDR mediated biological efficacy in the absence of hypercalcemia is osteoporosis. Osteoporosis is a systemic disorder characterized by decreased bone mass and microarchitectural deterioration of bone tissue leading to bone fragility and increased susceptibility to fractures of the hip, spine, and wrist (World Health Organization WHO 1994). Osteoporosis affects an estimated 75 million people in the United States, Europe, and Japan.

Within the past few years, several antiresorptive therapies have been introduced. These include bisphosphonates, hormone replacement therapy (HRT), a selective estrogen receptor modulator (SERM), and calcitonins. These treatments reduce bone resorption, bone formation, and increase bone density. However, none of these treatments increase true bone volume nor can they restore lost bone architecture.

Another major disorder that could benefits from VDR mediated biological activity is psoriasis. Psoriasis is one of the most common dermatologic diseases and is a chronic inflammatory skin condition characterized by erythematous, sharply demarcated papules and rounded plaques, covered by silvery micaceous scale.

Synthetic VDR ligands with reduced calcemic potential have been synthesized. For example, a class of bis-phenyl compounds stated to mimic 1α,25-dihydroxyvitamin $D_3$ is described in U.S. Pat. No. 6,218,430 and the article; "Novel nonsecosteroidal vitamin D mimics exert VDR-modulating activities with less calcium mobilization than 1α,25-Dihydroxyvitamin $D_3$" by Marcus F. Boehm, et. al., *Chemistry & Biology* 1999, Vol 6, No. 5, pgs. 265-275.

Synthetic VDR ligands having an aryl-thiophene nucleus are described in U.S. provisional patent application Ser. No. 60/384151, filed 29 May 2002.

There remains a need for improved treatments using alternative or improved pharmaceutical agents that mimic 1α,25-dihydroxyvitamin $D_3$ to stimulate bone formation, restore bone quality, and treat other diseases without the attendant disadvantage of hypercalcemia.

SUMMARY OF THE INVENTION

Novel compounds having a nucleus of Formula "(TP)", "(PT)", or (PT6) have been found effective as Vitamin D Receptor modulators (VDRM):

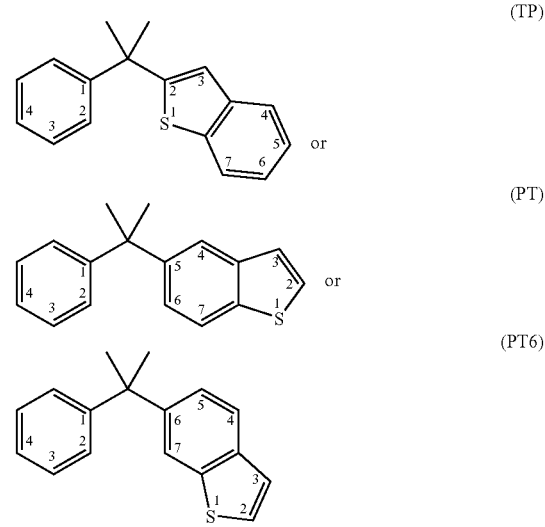

Compounds of the invention with VDR modulating activities are represented by formulae (IA)

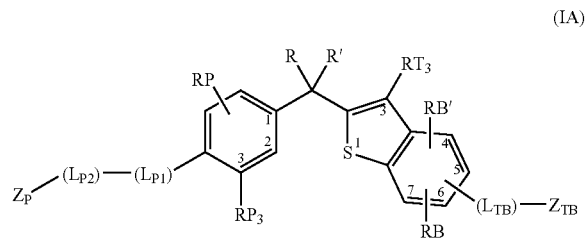

wherein the variables R, R', RP, RP$_3$, L$_{P1}$, L$_{P2}$, Z$_P$, RB, RB', RT$_3$, L$_{TB}$ and Z$_{TB}$ are as hereinafter defined.

Compounds of the invention with VDR modulating activities are also represented by formulae (IB)

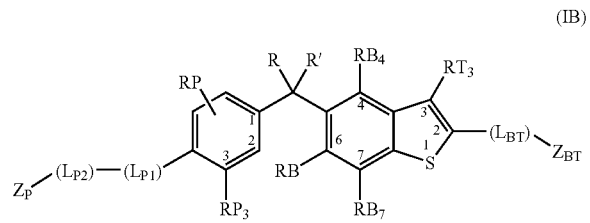
(IB)

wherein the variables R, R', RP, RP$_3$, L$_{P1}$, L$_{P2}$, Z$_P$, RB$_7$, RB, RB$_4$, RT$_3$, L$_{BT}$ and Z$_{BT}$ are as hereinafter defined.

Compounds of the invention with VDR modulating activities are also represented by formulae (IC)

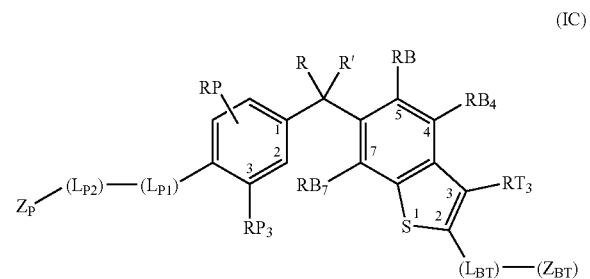
(IC)

wherein the variables R, R', RP, RP$_3$, L$_{P1}$, L$_{P2}$, Z$_P$, RB$_7$, RB, RB$_4$, RT$_3$, L$_{BT}$ and Z$_{BT}$ are as hereinafter defined.

In another aspect, the present invention is directed towards pharmaceutical compositions containing pharmaceutically effective amounts of compounds of formulae IA, IB, IC or a pharmaceutically acceptable salt or a prodrug thereof, either singly or in combination, together with pharmaceutically acceptable carriers and/or auxiliary agents.

Another aspect of the invention is a pharmaceutical formulation for treatment or prevention of osteoporosis containing pharmaceutically effective amounts of the vitamin D receptor modulator compound of formulae IA, IB, or IC alone or together with pharmaceutically effective amounts of co-agents conventionally used for the treatment of osteoporosis.

Another aspect of the invention is a pharmaceutical formulation for treatment or prevention of psoriasis containing pharmaceutically effective amounts of the vitamin D receptor modulator compound of formulae IA, IB, or IC alone or together with pharmaceutically effective amounts of co-agents conventionally used for the treatment of psoriasis.

Another aspect of the invention is a pharmaceutical formulation for treatment or prevention of prostate cancer containing pharmaceutically effective amounts of the vitamin D receptor modulator compound of formulae IA, IB, IC alone or together with pharmaceutically effective amounts of co-agents conventionally used for the treatment of prostate cancer.

Another aspect of the invention is to use the compounds of formulae IA, IB, or IC to treat disease states responsive to Vitamin D receptor ligands.

Another aspect of the invention is the prevention and treatment of acne, actinic keratosis, alopecia, Alzheimer's disease, autoimmune induced diabetes, benign prostatic hyperplasia, bladder cancer, bone fracture healing, breast cancer, Crohn's disease, prostate cancer, colon cancer, Type I diabetes, host-graft rejection, hypercalcemia, Type II diabetes, leukemia, multiple sclerosis, insufficient sebum secretion, osteomalacia, osteoporosis, insufficient dermal firmness, insufficient dermal hydration, myelodysplastic syndrome, psoriatic arthritis, psoriasis, renal osteodystrophy, rheumatoid arthritis, scleroderma, seborrheic dermatitis, skin cancer, systemic lupus erythematosis, skin cell damage from Mustard vesicants, ulcerative colitis, and wrinkles, by administering to a mammal in need thereof a pharmaceutically effective amount of a compound of Formulae IA, IB, or IC.

DETAILED DESCRIPTION OF THE INVENTION

Definitions

The term, "abscess" refers to adverse complications often associated with surgery, trama, or diseases that predispose the host to abscess formation from encapsulated bacteria lymphocytes, macrophages, and etc.

The term, "adhesion" refers to the adverse and abnormal union of surfaces normally separate by the formation of new fibrous tissue resulting from an inflammatory process.

The term, "compound of the invention" refers to a compound represented by Formulae IA, IB, or IC or as set out as products of the Examples or synthesis schemes described herein.

The term, "Active Ingredient" means a compound of the invention.

The term, "Mustard" is inclusive of both sulfur mustards and nitrogen mustards, either alone or in any combination. Examplary of such compounds are the vesicants; bis(2-chloroethyl)sulfide (Chemical Agent Symbol HD), Cl(CH$_2$)$_2$S(CH$_2$)$_2$Cl 1,2-bis(2-chloroethylthio)ethane (Chemical Agent Symbol Q), Cl(CH$_2$)$_2$S(CH$_2$)$_2$S(CH$_2$)$_2$Cl; bis(2-chloroethylthioethyl)ether, Cl(CH$_2$)$_2$S(CH$_2$)$_2$O(CH$_2$)$_2$S(CH$_2$)$_2$Cl (Chemical Agent Symbol T); tris(2-chloroethyl)amine (Chemical Agent Symbol HN3) N(CH$_2$CH$_2$Cl)$_3$; N-methyl-2,2'-dichlorodiethylamine (Chemical Agent Symbol NH2); and 2,2'-dichlorotriethylamine, CH$_3$CH$_2$N(CH$_2$CH$_2$Cl)$_2$ (Chemical Agent Symbol NH1).

The term, "(Acidic Group)" means an organic group that acts as a proton donor capable of hydrogen bonding. Illustrative of an (Acidic Group) is a group selected from the following:

—C(O)OH,

-5-tetrazolyl,

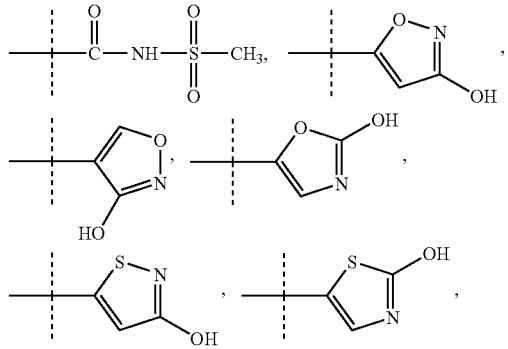

-continued

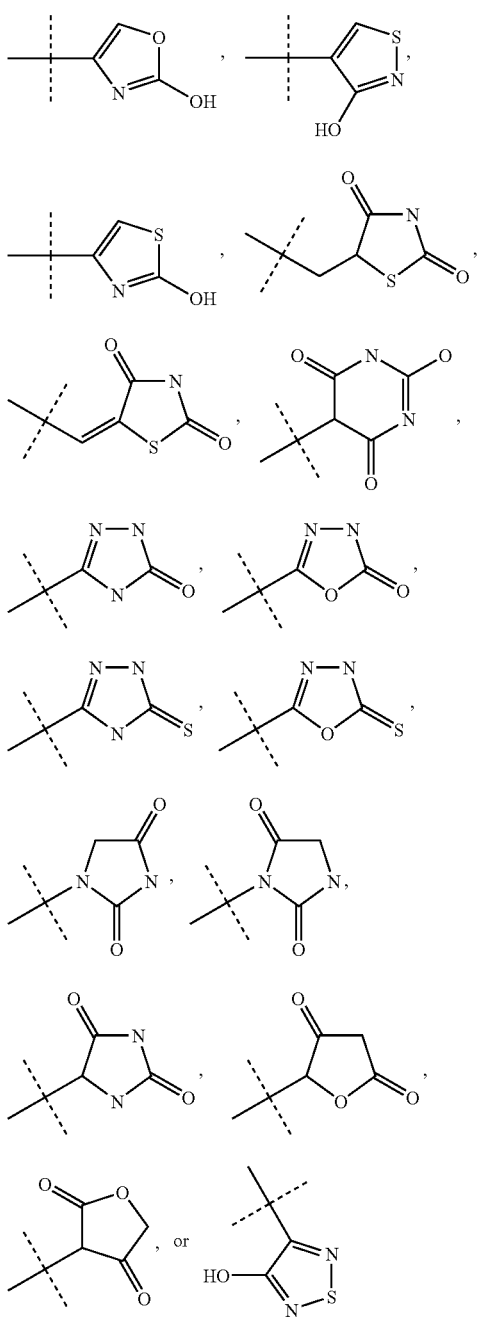

The term, "-1,3-thiazolidine-2,4-dione-5-ethylidene", refers to the radical represented by the structural formula:

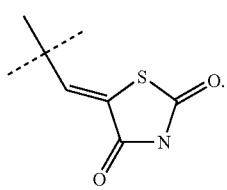

The term, "—CH$_2$—C(O)—N-pyrrolidine" refers to the radical represented by the structural formula:

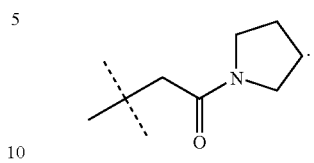

The term, "—CH$_2$—N-pyrrolidin-2-one" refers to the radical represented by the structural formula:

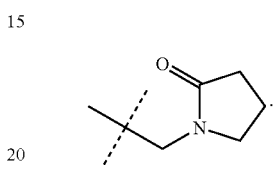

The term, "—CH$_2$-(1-methylpyrrolidin-2-one-3-yl)" refers to the organic radical represented by the structural formula:

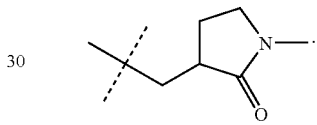

The term, "1,3,4-oxadiazolin-2-one-5-yl" refers to the organic radical represented by the structural formula:

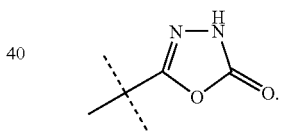

The term, "1,3,4-oxadiazolin-2-thione-5-yl" refers to the organic radical represented by the structural formula:

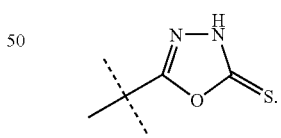

The terml, "imidazolidine-2,4-dione-5-yl" refers to the organic radical represented by the structural formula:

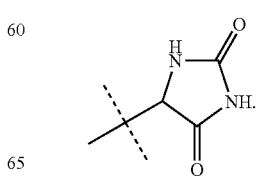

The term, "isoxazol-3-ol-5-yl" refers to the organic radical represented by the structural formula:

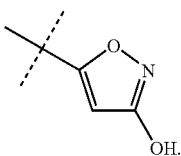

The dotted line symbol crossing a solid line representing a bond

means that the bond so marked is the bond of attachment.

The term, "mammal" includes humans.

The term "halo" refer to fluorine, chlorine, bromine, and iodine.

The term "sulfonate" refers to the group

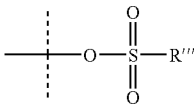

where R''' is $C_1$-$C_5$ alkyl, $C_1$-$C_5$ fluoroalkyl,

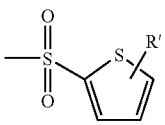

where R' is —CO$_2$H, —CO$_2$R''', —OH, —CF$_3$, or $C_1$-$C_5$ alkyl.

The term "sulfonamide" refers to the group methyl, ethyl, branched $C_3$-$C_5$ alkyl,

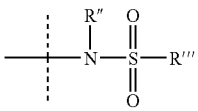

where R'' is H, $C_1$-$C_5$ alkyl, $C_1$-$C_5$ fluoroalkyl, or

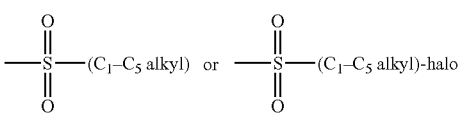

where R''' is $C_1$-$C_5$ alkyl, $C_1$-$C_5$ fluoroalkyl,

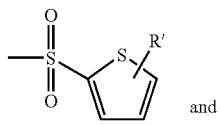

where R' is —CO2H, —CO2R''', —OH, —CF3, or $C_1$-$C_5$ alkyl.

The term, "$C_{1-3}$ alkyl" refers to an alkyl group selected from methyl, ethyl, n-propyl, and isopropyl.

The term, "branched $C_3$-$C_5$ alkyl" is an alkyl group selected from 1-methylethyl; 1-methylpropyl; 2-methylpropyl; 1,1-dimethylethyl; 1,1-dimethylpropyl; 1,2-dimethylpropyl; or 2,2-dimethylpropyl. Preferred branched $C_3$-$C_5$ alkyl groups are 2-methylpropyl and 1,1-dimethylethyl, with the 1,1-dimethylethyl group being most preferred.

The term "alkenyl" refers to aliphatic groups wherein the point of attachment is a carbon-carbon double bond, for example vinyl, 1-propenyl, and 1-cyclohexenyl. Alkenyl groups may be straight-chain, branched-chain, cyclic, or combinations thereof, and may be optionally substituted. Suitable alkenyl groups have from 2 to about 20 carbon atoms.

The term "$C_1$-$C_5$ alkyl" refers to saturated aliphatic groups including straight-chain, branched-chain, and cyclic groups and any combinations thereof. Examples of $C_1$-$C_5$ alkyl groups are methyl, ethyl, n-propyl, from 1-methylethyl; n-butyl, 1-methylpropyl; 2-methylpropyl; 1,1-dimethylethyl; n-amyl, 1,1-dimethylpropyl; 1,2-dimethylpropyl; and 2,2-dimethylpropyl.

The term "cycloalkyl" includes organic radicals such as cyclopropyl, cyclobutyl, cyclopentyl and cyclohexyl.

The term, "cycloalkenyl" includes organic radicals such as cyclopropenyl, cyclobutenyl, cyclopentenyl and cyclohexenyl.

The term, "$C_1$-$C_5$ fluoroalkyl" is an alkyl group containing fluorine and includes organic radicals such as —CF$_3$, —CHF$_2$, —CH$_2$F, —CF$_2$CF$_3$, —CHFCF$_3$, —CH$_2$CF$_3$, —CH$_2$CHF$_2$, and —CH$_2$CH$_2$F, with —CF$_3$ being preferred.

The abbreviation, "Me" means methyl.
The abbreviation, "Et" means ethyl.
The abbreviation, "iPr" means 1-methylethyl.
The abbreviation, "tBu" means 1,1-dimethylethyl.

The term,"terminal hydroxyalkyl" is a group selected from
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
1-hydroxy-2-methyl-1-(methylethyl)propyl,
2-methyl-3-hydroxy-4-dimethylpentyl,
2-methyl-3-hydroxy-3-ethylpentyl,
2-ethyl-3-hydroxy-3-ethylpentyl,
2-ethyl-3-hydroxy-4-dimethylpentyl,
1-hydroxycycloalkenyl; and
1-hydroxycycloalkyl.

The term, "3-methyl-3-hydroxypentyl" refers to the radical having the structural formula:

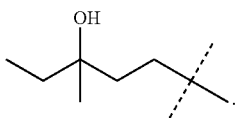

The term, "3-methyl-3-hydroxypentenyl" refers to the radical having the structural formula (both cis and trans isomers):

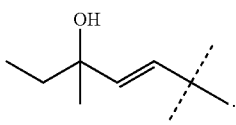

The term, "3-methyl-3-hydroxypentynyl" refers to the radical having the structural formula:

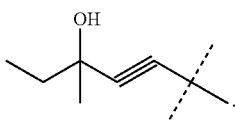

The term, "3-ethyl-3-hydroxypentyl" refers to the radical having the structural formula:

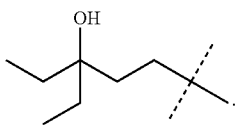

The term, "3-ethyl-3-hydroxypentenyl" refers to the radical having the structural formula (both cis and trans isomers):

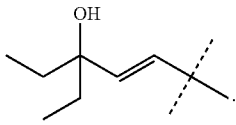

The term, "3-ethyl-3-hydroxypentynyl" refers to the radical having the structural formula:

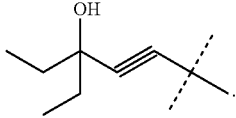

The term, "3-propyl-3-hydroxypentyl" refers to the radical having the structural formula:

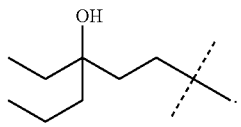

The term, "3-propyl-3-hydroxypentenyl" refers to the radical having the structural formula (both cis and trans isomers):

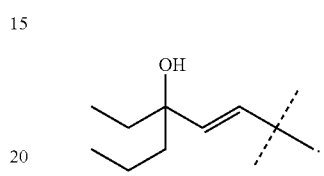

The term, "3-propyl-3-hydroxypentynyl" refers to the radical having the structural formula:

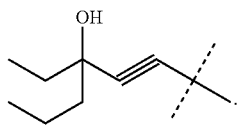

The term, "3-ethyl-3-hydroxy-4-methylpentyl" refers to the radical having the structural formula:

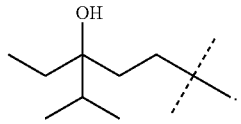

The term, "3-ethyl-3-hydroxy-4-methylpentenyl" refers to the radical having the structural formula (both cis and trans isomers):

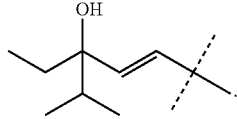

The term, "3-ethyl-3-hydroxy-4-methylpentynyl" refers to the radical having the structural formula:

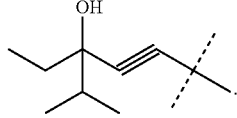

The term, "1-hydroxy-2-methyl-1-(methylethyl)propyl" refers to the radical having the structural formula:

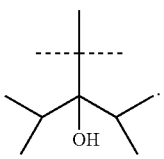

The term, "3-methyl-3-hydroxy-4,4-dimethylpentyl" refers to the radical having the structural formula:

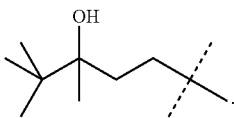

The term, "3-methyl-3-hydroxy-4,4-dimethylpentenyl." refers to the radical having the structural formula (both cis and trans isomers):

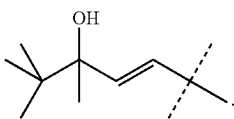

The term, "3-methyl-3-hydroxy-4,4-dimethylpentynyl" refers to the radical having the structural formula:

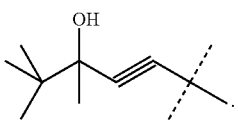

The term, "3-ethyl-3-hydroxy-4,4-dimethylpentyl" refers to the radical having the structural formula:

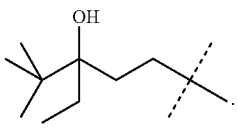

The term, "3-ethyl-3-hydroxy-4,4-dimethylpentenyl" refers to the radical having the structural formula (both cis and trans isomers):

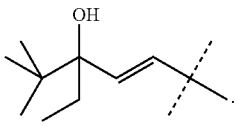

The term, "3-ethyl-3-hydroxy-4,4-dimethylpentynyl" refers to the radical having the structural formula:

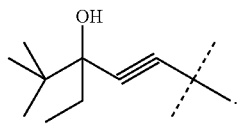

The term, "1-hydroxycycloalkenyl" refers to a radical selected from 1-hydroxycyclopentenyl, 1-hydroxycyclohexenyl, 1-hydroxycycloheptenyl, or 1-hydroxycyclooctenyl.

The term "hydroxycycloalkyl" refers to a radical having the general structural formula:

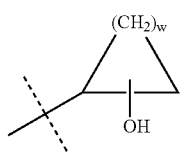

where w is an integer from 1 to 6 and the hydroxyl radical is substituted on any ring carbon atom.

The term "1-hydroxycycloalkyl" refers to a radical having the general structural formula:

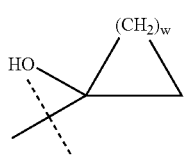

Examples of 1-hydroxycycloalkyl radicals are 1-hydroxycyclopropyl, 1-hydroxycyclobutyl, 1-hydroxycyclopentyl, 1-hydroxycyclohexyl, 1-hydroxycycloheptyl, and 1-hydroxycyclooctyl.

The abbreviation, "Me" means methyl.
The abbreviation, "Et" means ethyl.
The abbreviation, "iPr" means 1-methylethyl.
The abbreviation, "nPr" means n-propyl.
The abbreviation, "3Me3OH-Pentyl" means 3-methyl-3-hydroxypentyl.
The abbreviation, "3Me3OH-Pentenyl" means 3-methyl-3-hydroxypentenyl
The abbreviation, "3Me3OH-Pentynyl" means 3-methyl-3-hydroxypentynyl
The abbreviation, "3Et3OH-Pentyl" means 3-ethyl-3-hydroxypentyl.
The abbreviation, "3Et3OH-Pentenyl" means 3-ethyl-3-hydroxypentenyl
The abbreviation, "3Et3OH-Pentynyl" means 3-ethyl-3-hydroxypentynyl
The abbreviation, "3Pr3OH-Pentyl" means 3-propyl-3-hydroxypentyl.
The abbreviation, "3Pr3OH-Pentenyl" means 3-propyl-3-hydroxypentenyl.
The abbreviation, "3Pr3OH-Pentynyl" means 3-propyl-3-hydroxypentynyl.
The abbreviation, "3Et3OH4Me-Pentyl" means 3-ethyl-3-hydroxy-4-methylpentyl.

The abbreviation, "3Et3OH4Me-Pentenyl" means 3-ethyl-3-hydroxy-4-methylpentenyl, The abbreviation, "3Et3OH4Me-Pentynyl" means 3-ethyl-3-hydroxy-4-methylpentynyl.

The abbreviation, "1OH2Me1MeEt-Propyl" means 1-hydroxy-2-methyl-1-(methylethyl)propyl.

Compounds of the Invention:

The compounds of the invention with vitamin receptor modulating (VDRM) activity are represented by formula (IA) or a pharmaceutically acceptable salt or a prodrug derivative thereof:

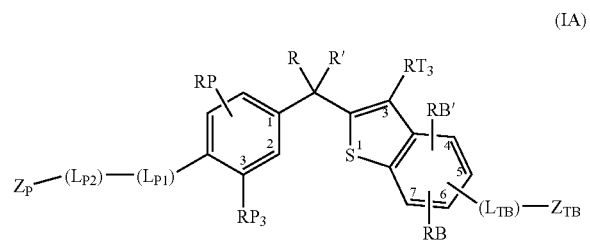

(IA)

wherein

R and R' are independently $C_1$-$C_5$ alkyl, $C_1$-$C_5$ fluoroalkyl, or together R and R' form a substituted or unsubstituted, saturated or unsaturated carbocyclic ring having from 3 to 8 carbon atoms;

$RP_3$ and RB are independently selected from the group consisting of hydrogen, halo, $C_1$-$C_5$ alkyl, $C_1$-$C_5$ fluoroalkyl, —O—$C_1$-$C_5$ alkyl, —S—$C_1$-$C_5$ alkyl, —O—$C_1$-$C_5$ fluoroalkyl, —CN, —$NO_2$, acetyl, —S—$C_1$-$C_5$ fluoroalkyl, $C_2$-$C_5$ alkenyl, $C_3$-$C_5$ cycloalkyl, and $C_3$-$C_5$ cycloalkenyl;

RP, $RT_3$, and RB' are independently selected from hydrogen, halo, $C_1$-$C_5$ alkyl, $C_1$-$C_5$ fluoroalkyl, —O—$C_1$-$C_5$ alkyl, —S—$C_1$-$C_5$ alkyl, —O—$C_1$-$C_5$ fluoroalkyl, —CN, —$NO_2$, acetyl, —S—$C_1$-$C_5$ fluoroalkyl, $C_2$-$C_5$ alkenyl, $C_3$-$C_5$ cycloalkyl, or $C_3$-$C_5$ cycloalkenyl;

($L_{P1}$), ($L_{P2}$), and ($L_{TB}$) are divalent linking groups independently selected from the group consisting of

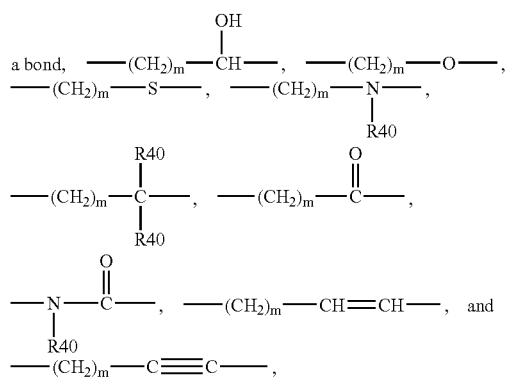

where m is 0, 1, or 2, and each R40 is independently hydrogen, $C_1$-$C_5$ alkyl, or $C_1$-$C_5$ fluoroalkyl;

$Z_P$ is
  branched $C_3$-$C_5$ alkyl,
  3-methyl-3-hydroxypentyl,
  3-methyl-3-hydroxypentenyl,
  3-methyl-3-hydroxypentynyl,
  3-ethyl-3-hydroxypentyl,
  3-ethyl-3-hydroxypentenyl,
  3-ethyl-3-hydroxypentynyl,
  3-ethyl-3-hydroxy-4-methylpentyl,
  3-ethyl-3-hydroxy-4-methylpentenyl,
  3-ethyl-3-hydroxy-4-methylpentynyl,
  3-propyl-3-hydroxypentyl,
  3-propyl-3-hydroxypentenyl,
  3-propyl-3-hydroxypentynyl,
  1-hydroxy-2-methyl-1-(methylethyl)propyl,
  2-methyl-3-hydroxy-4-dimethylpentyl,
  2-methyl-3-hydroxy-3-ethylpentyl,
  2-ethyl-3-hydroxy-3-ethylpentyl,
  2-ethyl-3-hydroxy-4-dimethylpentyl,
  3-methyl-3-hydroxy-4,4-dimethylpentyl,
  3-methyl-3-hydroxy-4,4-dimethylpentenyl,
  3-methyl-3-hydroxy-4,4-dimethylpentyl,
  3-ethyl-3-hydroxy-4,4-dimethylpentynyl,
  3-ethyl-3-hydroxy-4,4-dimethylpentenyl,
  3-ethyl-3-hydroxy-4,4-dimethylpentynyl,
  1-hydroxycycyclopentenyl,
  1-hydroxycyclohexenyl,
  1-hydroxycycloheptenyl,
  1-hydroxycyclooctenyl,
  1-hydroxycyclopropyl,
  1-hydroxycyclobutyl,
  1-hydroxycyclopentyl,
  1-hydroxycyclohexyl,
  2-oxocyclohexyloxy
  2-oxocyclohexylmethyl
  3-methyl-2-oxocyclohexyloxy,
  3-methyl-2-oxocyclohexylmethyl,
  3,3-dimethyl-2-oxocyclohexyloxy,
  3,3-dimethyl-2-oxocyclohexylmethyl,
  2-hydroxycyclohexyloxy,
  2-hydroxycyclohexylmethyl,
  3-methyl-2-hydroxycyclohexyloxy,
  3-methyl-2-hydroxycyclohexylmethyl,
  3,3-dimethyl-2-hydroxycyclohexyloxy,
  3,3-dimethyl-2-hydroxycyclohexylmethyl,
  1-hydroxycycloheptyl, or
  1-hydroxycyclooctyl;

provided, however, that when
  $Z_P$ is
  3-methyl-3-hydroxypentyl,
  3-methyl-3-hydroxypentenyl,
  3-methyl-3-hydroxypentynyl,
  3-ethyl-3-hydroxypentyl,
  3-ethyl-3-hydroxypentenyl,
  3-ethyl-3-hydroxypentynyl,
  3-ethyl-3-hydroxy-4-methylpentyl,
  3-ethyl-3-hydroxy-4-methylpentenyl,
  3-ethyl-3-hydroxy-4-methylpentynyl,
  3-propyl-3-hydroxypentyl,
  3-propyl-3-hydroxypentenyl,
  3-propyl-3-hydroxypentynyl,
  3-methyl-3-hydroxy-4,4-dimethylpentyl,
  3-methyl-3-hydroxy-4,4-dimethylpentenyl,
  3-methyl-3-hydroxy-4,4-dimethylpentyl,
  3-ethyl-3-hydroxy-4,4-dimethylpentynyl,
  3-ethyl-3-hydroxy-4,4-dimethylpentenyl,
  3-ethyl-3-hydroxy-4,4-dimethylpentynyl,
  2-methyl-3-hydroxy-4-dimethylpentyl,
  2-methyl-3-hydroxy-3-ethylpentyl,
  2-ethyl-3-hydroxy-3-ethylpentyl,
  2-ethyl-3-hydroxy-4-dimethylpentyl, or 1-hydroxy-2-methyl-1-(methylethyl)propyl;
then ($L_{P1}$) and ($L_{P2}$) combine as a bond;

$Z_{TB}$ is selected from
—O—($C_1$-$C_5$ alkyl),
—O—($C_2$-$C_5$ alkenyl),
—O—($C_3$-$C_5$ cycloalkyl),
—O—($C_3$-$C_5$ cycloalkenyl),
—O—($C_1$-$C_5$ hydroxyalkyl),
—O—($C_1$-$C_5$ fluoroalkyl),
—O—($C_1$-$C_5$ alkyl)-phenyl,
—O—($C_1$-$C_5$ alkyl)-(O)—($C_1$-$C_5$ alkyl),
—O—($C_1$-$C_5$ alkyl)-$NH_2$,
—O—($C_1$-$C_5$ alkyl)-NH—($C_1$-$C_5$ alkyl)$_2$,
—O—($C_1$-$C_5$ alkyl)-C(O)—$NH_2$,
—O—($C_1$-$C_5$ alkyl)-C(O)—NH—($C_1$-$C_5$ alkyl),
—O—($C_1$-$C_5$ alkyl)-C(O)—N—($C_1$-$C_5$ alkyl)$_2$,
—O—($C_1$-$C_5$ alkyl)-C(O)—OH,
—O—($C_1$-$C_5$ alkyl)-C(O)—NH-5-tetrazolyl,
—O—($C_1$-$C_5$ alkyl)-C(O)—($C_1$-$C_5$ alkyl),
—O—($C_1$-$C_5$ alkyl)-C(O)—(O—$C_1$-$C_5$ alkyl),
—O—($C_1$-$C_5$ alkyl)-$NH_2$,
—O—($C_1$-$C_5$ alkyl)-NH—($C_1$-$C_5$ alkyl),
—O—($C_1$-$C_5$ alkyl)-N—($C_1$-$C_5$ alkyl)$_2$,
—O—($C_1$-$C_5$ alkyl)-NH—$SO_2$—($C_1$-$C_5$ alkyl),
—O—($C_1$-$C_5$ alkyl)-N-pyrrolidin-2-one,
—O—($C_1$-$C_5$ alkyl)-N-pyrrolidine,
—O—($C_1$-$C_5$ alkyl)-(1-methylpyrrolidin-2-one-3-yl),
—O—($C_1$-$C_5$ alkyl)-$SO_2$—($C_1$-$C_5$ alkyl,)
—O—($C_1$-$C_5$ alkyl)-$SO_2$—$NH_2$,
—O—($C_1$-$C_5$ alkyl)-$SO_2$—NH—($C_1$-$C_5$ alkyl),
—O—($C_1$-$C_5$ alkyl)-$SO_2$—N—($C_1$-$C_5$ alkyl)$_2$,
—O—($C_1$-$C_5$ alkyl)-$SO_2$—($C_1$-$C_5$ alkyl),
—O—($C_1$-$C_5$ alkyl)-S(O)—($C_1$-$C_5$ alkyl,)
—O—($C_1$-$C_5$ alkyl)-S(O)—$NH_2$,
—O—($C_1$-$C_5$ alkyl)-S(O)—NH—($C_1$-$C_5$ alkyl),
—O—($C_1$-$C_5$ alkyl)-S(O)—N—($C_1$-$C_5$ alkyl)$_2$,
—O—($C_1$-$C_5$ alkyl)-S(O)—($C_1$-$C_5$ alkyl),
—O—($C_1$-$C_5$ alkyl)-P(O)—(O—$C_1$-$C_5$ alkyl)$_2$,
—O—($C_1$-$C_5$ alkyl)-5-tetrazolyl,
—O—$CH_2$—$CO_2H$,
—O—$CH_2$-5-tetrazolyl,
—O—($C_1$-$C_5$ alkyl),
—O—C(O)—$NH_2$,
—O—C(O)—N—$(CH_3)_2$,
—O—C(S)—N—$(CH_3)_2$,
—O—C(O)—O—($C_1$-$C_5$ alkyl),
—O—(5-tetrazolyl),
—O—$SO_2$—($C_1$-$C_5$ alkyl,)
—O—$SO_2$—$NH_2$,
—O—$SO_2$—NH—($C_1$-$C_5$ alkyl),
—O—$SO_2$—N—($C_1$-$C_5$ alkyl)$_2$,
—O—S(O)—($C_1$-$C_5$ alkyl,)
—O—S(O)—$NH_2$,
—O—S(O)—NH—($C_1$-$C_5$ alkyl),
—O—S(O)—N—($C_1$-$C_5$ alkyl)$_2$,
—S—($C_1$-$C_5$ alkyl),
—S—($C_2$-$C_5$ alkenyl),
—S—($C_3$-$C_5$ cycloalkyl),
—S—($C_3$-$C_5$ cycloalkenyl),
—S—($C_1$-$C_5$ fluoroalkyl),
—S—($C_1$-$C_5$ hydroxyalkyl),
—S—($C_1$-$C_5$ alkyl)-phenyl,
—S—($C_1$-$C_5$ alkyl)-O—($C_1$-$C_5$ alkyl),
—S—($C_1$-$C_5$ alkyl)-C(O)—OH,
—S—($C_1$-$C_5$ alkyl)-C(O)—($C_1$-$C_5$ alkyl),
—S—($C_1$-$C_5$ alkyl)-C(O)—O—($C_1$-$C_5$ alkyl),
—S—($C_1$-$C_5$ alkyl)-C(O)—$NH_2$,
—S—($C_1$-$C_5$ alkyl)-C(O)—NH—($C_1$-$C_5$ alkyl),
—S—($C_1$-$C_5$ alkyl)-C(O)—N—($C_1$-$C_5$ alkyl)$_2$,
—S—($C_1$-$C_5$ alkyl)-$NH_2$,
—S—($C_1$-$C_5$ alkyl)-NH—($C_1$-$C_5$ alkyl),
—S—($C_1$-$C_5$ alkyl)-N—($C_1$-$C_5$ alkyl)$_2$,
—S—($C_1$-$C_5$ alkyl)-NH—$SO_2$—($C_1$-$C_5$ alkyl),
—S—($C_1$-$C_5$ alkyl)-N-pyrrolidin-2-one,
—S—($C_1$-$C_5$ alkyl)-N-pyrrolidine,
—S—($C_1$-$C_5$ alkyl)-(1-methylpyrrolidin-2-one-3-yl),
—S—($C_1$-$C_5$ alkyl)-$SO_2$—($C_1$-C5 alkyl),
—S—($C_1$-$C_5$ alkyl)-$SO_2$—$NH_2$,
—S—($C_1$-$C_5$ alkyl)-$SO_2$—NH—($C_1$-$C_5$ alkyl),
—S—($C_1$-$C_5$ alkyl)-$SO_2$—N—($C_1$-$C_5$ alkyl)$_2$,
—S—($C_1$-$C_5$ alkyl)-$SO_2$—($C_1$-$C_5$ alkyl),
—S—($C_1$-$C_5$ alkyl)-P(O)—(O—$C_1$-$C_5$ alkyl)$_2$,
—S—($C_1$-$C_5$ alkyl)-5-tetrazolyl,
—S—($C_1$-$C_5$ alkyl)-S(O)—($C_1$-C5 alkyl),
—S—($C_1$-$C_5$ alkyl)-S(O)—$NH_2$,
—S—($C_1$-$C_5$ alkyl)-S(O)—NH—($C_1$-$C_5$ alkyl),
—S—($C_1$-$C_5$ alkyl)-S(O)—N—($C_1$-$C_5$ alkyl)$_2$,
—S—($C_1$-$C_5$ alkyl)-S(O)—($C_1$-$C_5$ alkyl),
—$SO_2$—($C_1$-$C_5$ alkyl),
—$SO_2$—($C_2$-$C_5$ alkenyl),
—$SO_2$—($C_3$-$C_5$ cycloalkyl),
—$SO_2$—($C_3$-$C_5$ cycloalkenyl),
—$SO_2$—($C_1$-$C_5$ hydroxyalkyl),
—$SO_2$—($C_1$-$C_5$ fluoroalkyl),
—$SO_2$—($C_1$-$C_5$)-phenyl,
—$SO_2$—$NH_2$,
—$SO_2$—NH—($C_1$-$C_5$ alkyl),
—$SO_2$—NH—$CH_2$—C(O)OH,
—$SO_2$—NH—$CH_2$—C(O)(O—$C_1$-$C_5$ alkyl),
—$SO_2$—NH—($C_1$-$C_5$ alkyl)-C(O)OH,
—$SO_2$—NH—($C_1$-$C_5$ alkyl)-C(O)(O—$C_1$-$C_5$ alkyl),
—$SO_2$—NHC(O)—($C_3$-$C_6$ cycloalkyl),
—$SO_2$—NH—C(O)—($C_1$-$C_5$ alkyl),
—$SO_2$—N—($C_1$-$C_5$ alkyl)$_2$,
—$SO_2$—($C_1$-$C_5$ alkyl)-O—($C_1$-$C_5$ alkyl),
—$SO_2$—($C_1$-$C_5$ alkyl)-C(O)—($C_1$-$C_5$ alkyl),
—$SO_2$—($C_1$-$C_5$ alkyl)$NH_2$,
—$SO_2$—($C_1$-$C_5$ alkyl)-NH—($C_1$-$C_5$ alkyl),
—$SO_2$—($C_1$-$C_5$ alkyl)-N—($C_1$-$C_5$ alkyl)$_2$,
—$SO_2$—($C_1$-$C_5$ alkyl)-C(O)—$NH_2$,
—$SO_2$—($C_1$-$C_5$ alkyl)-C(O)—NH—($C_1$-$C_5$ alkyl),
—$SO_2$—($C_1$-$C_5$ alkyl)-C(O)—N—($C_1$-$C_5$ alkyl)$_2$,
—$SO_2$—($C_1$-$C_5$ alkyl)-NH—$SO_2$—($C_1$-$C_5$ alkyl),
—$SO_2$—($C_1$-$C_5$ alkyl)-N-pyrrolidin-2-one,
—$SO_2$—($C_1$-$C_5$ alkyl)-N-pyrrolidine,
—$SO_2$—($C_1$-$C_5$ alkyl)-(1-methylpyrrolidin-2-one-3-yl),
—$SO_2$—($C_1$-$C_5$ alkyl)-C(O)—O—($C_1$-$C_5$ alkyl),
—$SO_2$—($C_1$-$C_5$ alkyl)-C(O)—OH,
—$SO_2$—($C_1$-$C_5$ alkyl)-5-tetrazolyl,
—$SO_2$—($C_1$-$C_5$ alkyl)-$SO_2$—($C_1$-$C_5$ alkyl),
—$SO_2$—($C_1$-$C_5$ alkyl)-$SO_2$—$NH_2$,
—$SO_2$—($C_1$-$C_5$ alkyl)-$SO_2$—NH—($C_1$-$C_5$ alkyl),
—$SO_2$—($C_1$-$C_5$ alkyl)-$SO_2$—N—($C_1$-C5 alkyl)$_2$,
—$SO_2$—($C_1$-$C_5$ alkyl)-$SO_2$—($C_1$-$C_5$ alkyl),
—$SO_2$—($C_1$-$C_5$ alkyl)-P(O)—(O—$C_1$-$C_5$ alkyl)$_2$,
—$SO_2$—($C_1$-$C_5$ alkyl),
—$SO_2$—($C_2$-$C_5$ alkenyl),
—$SO_2$—($C_3$-$C_5$ cycloalkyl),
—$SO_2$—($C_3$-$C_5$ cycloalkenyl),
—$SO_2$—($C_1$-$C_5$ hydroxyalkyl),
—$SO_2$—($C_1$-$C_5$ fluoroalkyl),
—$SO_2$—($C_1$-$C_5$)-phenyl,
—$SO_2$—N=CHN($C_1$-$C_5$ alkyl)$_2$, —S(O)—NH$_2$,
—S(O)—NH—(C$_1$-C$_5$ alkyl),
—S(O)—NH—CH$_2$—C(O)OH
—S(O)—NH—(C$_1$-C$_5$ alkyl)-C(O)OH,
—S(O)—NH—CH$_2$—C(O)(O—C$_1$-C$_5$ alkyl),
—S(O)—NH—(C$_1$-C$_5$ alkyl)-C(O)(O—C$_1$-C$_5$ alkyl),
—S(O)HC(O)—(C$_3$-C$_6$ cycloalkyl),
—S(O)—NH—C(O)—(C$_1$-C$_5$ alkyl),
—S(O)—N—(C$_1$-C$_5$ alkyl)$_2$,
—S(O)—(C$_1$-C$_5$ alkyl)-O—(C$_1$-C$_5$ alkyl),
—S(O)—(C$_1$-C$_5$ alkyl)-C(O)—(C$_1$-C$_5$ alkyl),
—S(O)—(C$_1$-C$_5$ alkyl)-C(O)—(O—C$_1$-C$_5$ alkyl),
—S(O)—(C$_1$-C$_5$ alkyl)-NH—(C$_1$-C$_5$ alkyl),
—S(O)—(C$_1$-C$_5$ alkyl)-N—(C$_1$-C$_5$ alkyl)$_2$,
—S(O)—(C$_1$-C$_5$ alkyl)-C(O)—NH$_2$,
—S(O)—(C$_1$-C$_5$ alkyl)-C(O)—NH—(C$_1$-C$_5$ alkyl),
—S(O)—(C$_1$-C$_5$ alkyl)-C(O)—N—(C$_1$-C$_5$ alkyl)$_2$,
—S(O)—(C$_1$-C$_5$ alkyl)-NH—SO$_2$—(C$_1$-C$_5$ alkyl),
—S(O)—(C$_1$-C$_5$ alkyl)-NH—S(O)—(C$_1$-C$_5$ alkyl),
—S(O)—(C$_1$-C$_5$ alkyl)-N-pyrrolidin-2-one,
—S(O)—(C$_1$-C$_5$ alkyl)-N-pyrrolidine,
—S(O)—(C$_1$-C$_5$ alkyl)-(1-methylpyrrolidin-2-one-3-yl),
—S(O)—(C$_1$-C$_5$ alkyl)-C(O)—(O—C$_1$-C$_5$ alkyl),
—S(O)—(C$_1$-C$_5$ alkyl)-C(O)—OH,
—S(O)—(C$_1$-C$_5$ alkyl)-5-tetrazolyl,
—S(O)—(C$_1$-C$_5$ alkyl)-SO$_2$—(C$_1$-C$_5$ alkyl),
—S(O)—(C$_1$-C$_5$ alkyl)-S(O)—(C$_1$-C$_5$ alkyl),
—S(O)—(C$_1$-C$_5$ alkyl)-SO$_2$—NH$_2$,
—S(O)—(C$_1$-C$_5$ alkyl)-S(O)—NH$_2$,
—S(O)—(C$_1$-C$_5$ alkyl)-SO$_2$—NH—(C$_1$-C$_5$ alkyl),
—S(O)—(C$_1$-C$_5$ alkyl)-S(O)—NH—(C$_1$-C$_5$ alkyl),
—S(O)—(C$_1$-C$_5$ alkyl)-SO$_2$—N—(C$_1$-C$_5$ alkyl)$_2$,
—S(O)—(C$_1$-C$_5$ alkyl)-S(O)—N—(C$_1$-C$_5$ alkyl)$_2$,
—S(O)—(C$_1$-C$_5$ alkyl)-SO$_2$—(C$_1$-C$_5$ alkyl),
—S(O)—(C$_1$-C$_5$ alkyl)-S(O)—(C$_1$-C$_5$ alkyl),
—S(O)—(C$_1$-C$_5$ alkyl)-P(O)—(O—C$_1$-C$_5$ alkyl)$_2$,
—S(O)—N═CHN(C$_1$-C$_5$ alkyl)$_2$,
—NHC(S)NH$_2$,
—NHC(S)NH—(C$_1$-C$_5$ alkyl),
—NHC(S)N—(C$_1$-C$_5$ alkyl)$_2$,
—NHC(S)NH—(C$_2$-C$_5$ alkenyl),
—NHC(S)NH—(C$_3$-C$_5$ cycloalkyl),
—NHC(S)NH—(C$_3$-C$_5$ cycloalkenyl),
—NHC(S)NH—(C$_1$-C$_5$ fluoroalkyl),
—NHC(S)NH—(C$_1$-C$_5$ hydroxyalkyl,
—NHC(S)NH—(C$_1$-C$_5$ fluoroalkyl)
—NHC(S)NH-phenyl,
—NHC(S)NH—(C$_1$-C$_5$ alkyl)-C(O)—OH,
—NHC(S)NH—(C$_1$-C$_5$ alkyl)-O—(C$_1$-C$_5$ alkyl),
—NHC(S)NH—(C$_1$-C$_5$ alkyl)-C(O)—(C$_1$-C$_5$ alkyl),
—NHC(S)NH—(C$_1$-C$_5$ alkyl)-C(O)—(O—C$_1$-C$_5$ alkyl),
—NHC(S)NH—(C$_1$-C$_5$ alkyl)-NH$_2$,
—NHC(S)NH—(C$_1$-C$_5$ alkyl)-NH—(C$_1$-C$_5$ alkyl),
—NHC(S)NH—(C$_1$-C$_5$ alkyl)-N—(C$_1$-C$_5$ alkyl)$_2$,
—NHC(S)NH—(C$_1$-C$_5$ alkyl)-C(O)—NH$_2$,
—NHC(S)NH—(C$_1$-C$_5$ alkyl)-C(O)—NH—(C$_1$-C$_5$ alkyl),
—NHC(S)NH—(C$_1$-C$_5$ alkyl)-C(O)—N—(C$_1$-C$_5$ alkyl)$_2$,
—NHC(S)NH—(C$_1$-C$_5$ alkyl)-NH—SO$_2$—(C$_1$-C$_5$ alkyl),
—NHC(S)NH—(C$_1$-C$_5$ alkyl)-NH—S(O)—(C$_1$-C$_5$ alkyl),
—NHC(S)NH—(C$_1$-C$_5$ alkyl)-N-pyrrolidin-2-one,
—NHC(S)NH—(C$_1$-C$_5$ alkyl)-N-pyrrolidine,
—NHC(S)NH—(C$_1$-C$_5$ alkyl)-(1-methylpyrrolidin-2-one-3-yl),
—NHC(S)NH—(C$_1$-C$_5$ alkyl)-5-tetrazolyl,
—NHC(S)NH—(C$_1$-C$_5$ alkyl)-SO$_2$—(C$_1$-C$_5$ alkyl),
—NHC(S)NH—(C$_1$-C$_5$ alkyl)-SO$_2$—NH$_2$,
—NHC(S)NH—(C$_1$-C$_5$ alkyl)-SO$_2$—NH—(C$_1$-C$_5$ alkyl),
—NHC(S)NH—(C$_1$-C$_5$ alkyl)-SO$_2$—N—(C$_1$-C$_5$ alkyl)$_2$,
—NHC(S)NH—(C$_1$-C$_5$ alkyl)-S(O)—(C$_1$-C$_5$ alkyl),
—NHC(S)NH—(C$_1$-C$_5$ alkyl)-S(O)—NH$_2$,
—NHC(S)NH—(C$_1$-C$_5$ alkyl)-S(O)—NH—(C$_1$-C$_5$ alkyl),
—NHC(S)NH—(C$_1$-C$_5$ alkyl)-S(O)—N—(C$_1$-C$_5$ alkyl)$_2$,
—NHC(S)NH—(C$_1$-C$_5$ alkyl)-P(O)—(O—C$_1$-C$_5$ alkyl)$_2$,
—NHC(O)NH$_2$,
—NHC(O)NH—(C$_1$-C$_5$ alkyl),
—NHC(O)N—(C$_1$-C$_5$ alkyl)$_2$,
—NHC(O)NH—(C$_2$-C$_5$ alkenyl),
—NHC(O)NH—(C$_3$-C$_5$ cycloalkyl),
—NHC(O)NH—(C$_3$-C$_5$ cycloalkenyl),
—NHC(O)NH—(C$_1$-C$_5$ hydroxyalkyl),
—NHC(O)NH—(C$_1$-C$_5$ fluoroalkyl),
—NHC(O)NH-phenyl,
—NHC(O)NH—(C$_1$-C$_5$ alkyl)-NH$_2$,
—NHC(O)NH—(C$_1$-C$_5$ alkyl)-NH—(C$_1$-C$_5$ alkyl),
—NHC(O)NH—(C$_1$-C$_5$ alkyl)-N—(C1-C$_5$ alkyl)$_2$,
—NHC(O)NH—(C$_1$-C$_5$ alkyl)-O—(C$_1$-C$_5$ alkyl),
—NHC(O)NH—(C$_1$-C$_5$ alkyl)-NH$_2$,
—NHC(O)NH—(C$_1$-C$_5$ alkyl)-NH—(C$_1$-C$_5$ alkyl),
—NHC(O)NH—(C$_1$-C$_5$ alkyl)-N—(C$_1$-C$_5$ alkyl)$_2$,
—NHC(O)NH—(C$_1$-C$_5$ alkyl)-C(O)—NH$_2$,
—NHC(O)NH—(C$_1$-C$_5$ alkyl)-C(O)—NH—(C$_1$-C$_5$ alkyl),
—NHC(O)NH—(C$_1$-C$_5$ alkyl)-C(O)—N—(C$_1$-C$_5$ alkyl)$_2$,
—NHC(O)NH—(C$_1$-C$_5$ alkyl)-C(O)—(C$_1$-C$_5$ alkyl),
—NHC(O)NH—(C$_1$-C$_5$ alkyl)-NH—SO$_2$—(C$_1$-C$_5$ alkyl),
—NHC(O)NH—(C$_1$-C$_5$ alkyl)-N-pyrrolidin-2-one,
—NHC(O)NH—(C$_1$-C$_5$ alkyl)-N-pyrrolidine,
—NHC(O)NH—(C$_1$-C$_5$ alkyl)-(1-methylpyrrolidin-2-one-3-yl),
—NHC(O)NH—(C$_1$-C$_5$ alkyl)-C(O)—OH,
—NHC(O)NH—(C$_1$-C$_5$ alkyl)-C(O)—O—(C$_1$-C$_5$ alkyl),
—NHC(O)NH—(C$_1$-C$_5$ alkyl)-5-tetrazolyl,
—NHC(O)NH—(C$_1$-C$_5$ alkyl)-SO$_2$—(C$_1$-C$_5$ alkyl),
—NHC(O)NH—(C$_1$-C5 alkyl)-SO$_2$—NH$_2$,
—NHC(O)NH—(C$_1$-C$_5$ alkyl)-SO$_2$—NH—(C$_1$-C$_5$ alkyl),
—NHC(O)NH—(C$_1$-C$_5$ alkyl)-SO$_2$—N—(C$_1$-C$_5$ alkyl)$_2$,
—NHC(O)NH—(C$_1$-C$_5$ alkyl)-P(O)—O—(C$_1$-C$_5$ alkyl)$_2$,
—NH$_2$,
—NH—(C$_1$-C$_5$ alkyl),
—NH—CH$_2$—C(O)OH,
—N—(C$_1$-C$_5$ alkyl)$_2$,
—NH—C(O)—NH$_2$,
—NH—C(O)—NH—(C$_1$-C$_5$ alkyl),
—NH—C(O)—N—(C$_1$-C$_5$ alkyl)$_2$,
—NH—C(O)—(C$_1$-C$_5$ alkyl),
—NH—SO$_2$—(C$_1$-C$_5$ alkyl),
—NH—S(O)—(C$_1$-C$_5$ alkyl),
—N(CH$_3$)(OCH$_3$),
—N(OH)(CH$_3$),
—N-pyrrolidin-2-one,
—N-pyrrolidine,
-(1-methylpyrrolidin-2-one-3-yl),
—CO$_2$H,
—CO$_2$Me,
—CO$_2$Et,
—C(O)CH$_2$S(O)Me,
—C(O)CH$_2$S(O)Et, —C(O)CH₂S(O)₂Me,
—C(O)CH₂S(O)₂Et,
—C(O)CH₂CH₂S(O)Me,
—C(O)CH₂CH₂S(O)Et,
—C(O)CH₂CH₂S(O)₂Me,
—C(O)CH₂CH₂S(O)₂Et,
—C(O)CH(Me)CH₂CO₂H,
—C(O)CH(Me)CH₂CO₂Me,
—C(O)CH(Me)CH₂CO₂Et,
—C(O)CH(Me)CH₂CO₂iPr,
—C(O)CH(Me)CH₂CO₂tBu,
—C(O)CH(Me)CH(Me)CO₂H,
—C(O)CH(Me)CH(Me)CO₂Me,
—C(O)CH(Me)CH(Me)CO₂Et,
—C(O)CH(Me)CH(Me)CO₂iPr,
—C(O)CH(Me)CH(Me)CO₂tBu,
—C(O)CH(Me)C(Me)₂CO₂H,
—C(O)CH(Me)C(Me)₂CO₂Me,
—C(O)CH(Me)C(Me)₂CO₂Et,
—C(O)CH(Me)C(Me)₂CO₂iPr,
—C(O)CH(Me)C(Me)₂CO₂tBu,
—C(O)CH(Me)CH(Et)CO₂H,
—C(O)CH(Me)CH(Et)CO₂Me,
—C(O)CH(Me)CH(Et)CO₂Et,
—C(O)CH(Me)CH(Et)CO₂iPr,
—C(O)CH(Me)CH(Et)CO₂tBu,
—C(O)C(O)OH,
—C(O)C(O)NH₂,
—C(O)C(O)NHMe,
—C(O)C(O)NMe₂,
—C(O)NH₂,
—C(O)NMe₂,
—C(O)NH—CH₂—C(O)OH,
—C(O)NH—CH₂—C(O)OMe,
—C(O)NH—CH₂—C(O)OEt,
—C(O)NH—CH₂—C(O)OiPr,
—C(O)NH—CH₂—C(O)OtBu,
—C(O)NH—CH(Me)-C(O)OH,
—C(O)NH—CH(Me)-C(O)OMe,
—C(O)NH—CH(Me)-C(O)OEt,
—C(O)NH—CH(Me)-C(O)iPr,
—C(O)NH—CH(Me)-C(O)tBu,
—C(O)NH—CH(Et)-C(O)OH,
—C(O)NH—C(Me)₂-C(O)OH,
—C(O)NH—C(Me)₂-C(O)OMe,
—C(O)NH—C(Me)₂-C(O)OEt,
—C(O)NH—C(Me)₂-C(O)iPr,
—C(O)NH—C(Me)₂-C(O)tBu,
—C(O)NH—CMe(Et)-C(O)OH,
—C(O)NH—CH(F)—C(O)OH,
—C(O)NH—CH(CF₃)—C(O)OH,
—C(O)NH—CH(OH)—C(O)OH,
—C(O)NH—CH(cyclopropyl)-C(O)OH,
—C(O)NH—C(Me)₂-C(O)OH,
—C(O)NH—C(Me)₂-C(O))OH,
—C(O)NH—CF(Me)-C(O)OH,
—C(O)NH—C(Me)(CF₃)—C(O)OH,
—C(O)NH—C(Me)(OH)—C(O)OH,
—C(O)NH—C(Me)(cyclopropyl)CO₂H
—C(O)NMe-CH₂—C(O)OH,
—C(O)NMe-CH₂—C(O)OMe,
—C(O)NMe-CH₂—C(O)OEt,
—C(O)NMe-CH₂—C(O)OiPr,
—C(O)NMe-CH₂—C(O)OtBu,
—C(O)NMe-CH₂—C(O)OH,
—C(O)NMe-CH(Me)-C(O)OH,
—C(O)NMe-CH(F)—C(O)OH, —C(O)NMe-CH(CF₃)—C(O)OH,
—C(O)NMe-CH(OH)—C(O)OH,
—C(O)NMe-CH(cyclopropyl)-C(O)OH,
—C(O)NMe-C(Me)₂-C(O)OH,
—C(O)NMe-CF(Me)-C(O)OH,
—C(O)NMe-C(Me)(CF₃)—C(O)OH,
—C(O)NMe-C(Me)(OH)—C(O)OH,
—C(O)NMe-C(Me)(cyclopropyl)-C(O)OH,
—C(O)NHS(O)Me,
—C(O)NHSO₂Me,
—C(O)—NH-5-tetrazolyl,
—C(O)NHS(O)Me,
—C(O)NHS(O)Et,
—C(O)NHSO₂Me,
—C(O)NHSO₂Et,
—C(O)NHS(O)iPr,
—C(O)NHSO₂iPr,
—C(O)NHS(O)tBu,
—C(O)NHSO₂tBu,
—C(O)NHCH₂S(O)Me,
—C(O)NHCH₂S(O)Et,
—C(O)NHCH₂SO₂Me,
—C(O)NHCH₂SO₂Et,
—C(O)NHCH₂CH₂S(O)Me,
—C(O)NHCH₂CH₂S(O)Et,
—C(O)NHCH₂CH₂SO₂Me,
—C(O)NHCH₂CH₂SO₂Et,
—C(O)N(Me)S(O)Me,
—C(O)N(Me)SO₂Me,
—C(O)—N(Me)-5-tetrazolyl,
—C(O)N(Me)S(O)Me,
—C(O)N(Me)S(O)Et,
—C(O)N(Me)SO₂Me,
—C(O)N(Me)SO₂Et,
—C(O)N(Me)S(O)iPr,
—C(O)N(Me))SO₂iPr,
—C(O)N(Me)S(O)tBu,
—C(O)N(Me)SO₂tBu,
—C(O)N(Me)CH₂S(O)Me,
—C(O)N(Me)CH₂S(O)Et,
—C(O)N(Me)CH₂SO₂Me,
—C(O)N(Me)CH₂SO₂Et,
—C(O)N(Me)CH₂CH₂S(O)Me,
—C(O)N(Me)CH₂CH₂S(O)Et,
—C(O)N(Me)CH₂CH₂SO₂Me,
—C(O)N(Me)CH₂CH₂SO₂Et,
—CH₂CO₂H,
—CH₂-5-tetrazolyl,
—CH₂CO₂Me,
—CH₂CO₂Et,
—CH₂NHS(O)Me,
—CH₂NHS(O)Et,
—CH₂NHSO₂Me,
—CH₂NHSO₂Et,
—CH₂NHS(O)iPr,
—CH₂NHSO₂iPr,
—CH₂NHS(O)tBu,
—CH₂NHSO₂tBu,
—CH₂NHCH₂CH₂SO₂CH₃,
—CH₂NH(CH₂CO₂H),
—CH₂N(C(O)Me)(CH₂CO₂H),
—CH₂—N-pyrrolidin-2-one,
—CH₂-(1-methylpyrrolidin-2-one-3-yl),
—CH₂S(O)Me,
—CH₂S(O)Et,
—CH₂S(O)₂Me,
—CH₂S(O)₂Et, —CH₂S(O)iPr,
—CH₂S(O)₂iPr,
—CH₂S(O)tBu,
—CH₂S(O)₂tBu,
—CH₂CO₂H, CH₂C(O)NH₂,
—CH₂C(O)NMe₂,
—CH₂C(O)NHMe,
—CH₂C(O)—N-pyrrolidine,
—CH₂S(O)₂Me, CH₂S(O)Me,
—CH(OH)CO₂H,
—CH(OH)C(O)NH₂,
—CH(OH)C(O)NHMe,
—CH(OH)C(O)NMe₂,
—CH(OH)C(O)NEt₂,
—CH₂CH₂CO₂H,
—CH₂CH₂CO₂Me,
—CH₂CH₂CO₂Et,
—CH₂CH₂C(O)NH₂,
—CH₂CH₂C(O)NHMe,
—CH₂CH₂C(O)NMe₂,
—CH₂CH₂-5-tetrazolyl,
—CH₂CH₂S(O)₂Me,
—CH₂CH₂S(O)Me,
—CH₂CH₂S(O)₂Et,
—CH₂CH₂S(O)Et,
—CH₂CH₂S(O)iPr,
—CH₂CH₂S(O)₂iPr,
—CH₂CH₂S(O)tBu,
—CH₂CH₂S(O)₂tBu,
—CH₂CH₂S(O)NH₂,
—CH₂CH₂S(O)NHMe,
—CH₂CH₂S(O)NMe₂,
—CH₂CH₂S(O)₂NH₂,
—CH₂CH₂S(O)₂NHMe
—CH₂CH₂S(O)₂NMe₂,
—CH₂CH₂CH₂S(O)Me,
—CH₂CH₂CH₂S(O)Et,
—CH₂CH₂CH₂S(O)₂Me,
—CH₂CH₂CH₂S(O)₂Et,
—CH(Me)CH₂C(O)OH,
—C(Me)₂CH₂C(O)OH,
 -5-tetrazolyl,

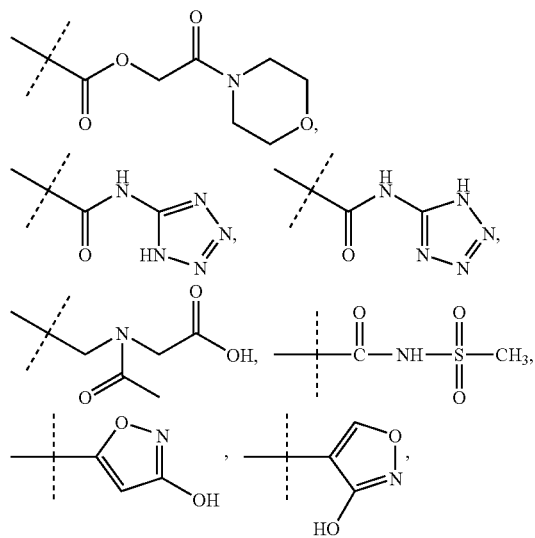

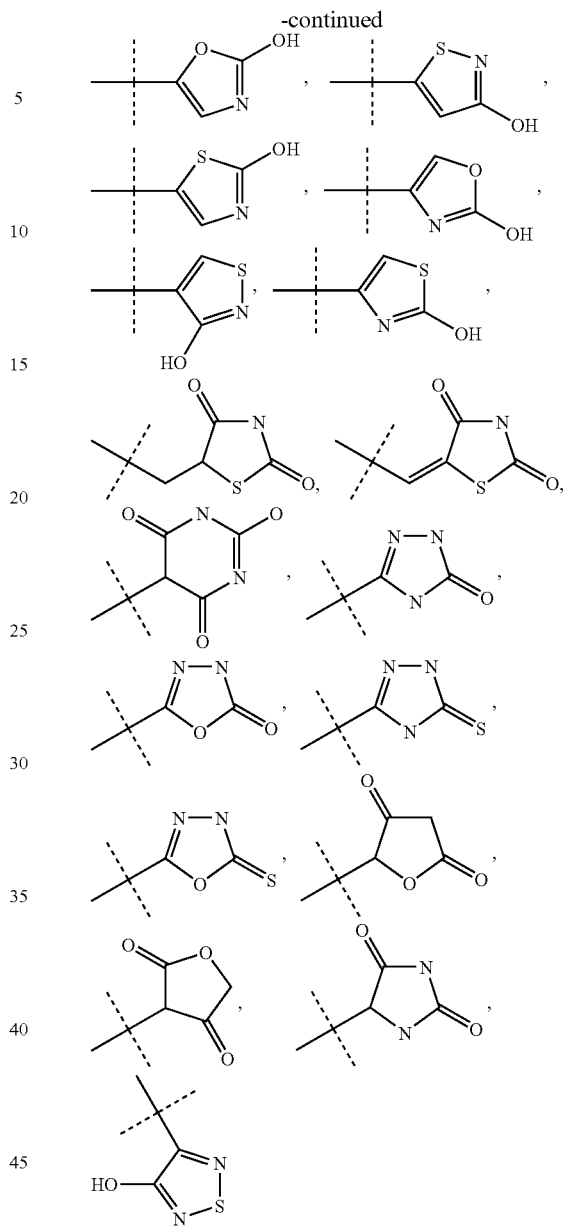

-1,3,4-oxadiazolin-2-one-5-yl,
-imidazolidine-2,4-dione-5-yl,
-isoxazol-3-ol-yl, or
-1,3,4-oxadiazolin-2-thione-5-yl;
provided that RB is substituted at either the 6 or 7 position of the benzothiophene ring, except that RB is substituted only at the 7 position of the benzothiophene ring when $Z_{TB}$ is at the 6 position.; and
provided that -($L_{TB}$)-$Z_{TB}$ is substituted at either the 5 or 6 position of the benzothiophene ring; and
provided that RB is substituted at either the 6 or 7 position of the benzothiophene ring, except that RB is substituted only at the 7 position of the benzothiophene ring when the group -($L_{TB}$)-$Z_{TB}$ is at the 6 position.; and
provided that RB' is substituted at either the 4 or 5 position of the benzothiophene ring, except that RB' is substituted only at the 5 position of the benzothiophene ring when the group -($L_{TB}$)-$Z_{TB}$ is at the 6 position of the phenyl ring; and provided that RP is substituted at either the 2, or 5 or 6 position of the phenyl ring.

The compounds of the invention with vitamin receptor modulating (VDRM) activity are represented by formula (IB) or a pharmaceutically acceptable salt or a prodrug derivative thereof:

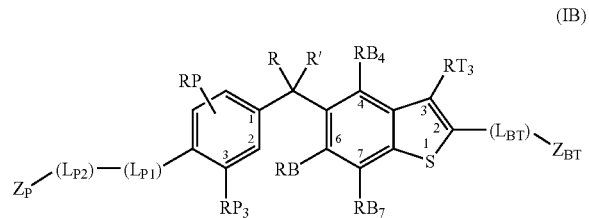

(IB)

wherein the variables R, R', RP, $RP_3$, $Z_P$, $RB_7$, RB, $RB_4$, $RT_3$, and $Z_{BT}$ are as hereinafter defined.

wherein

R and R' are independently $C_1$-$C_5$ alkyl, $C_1$-$C_5$ fluoroalkyl, or together R and R' form a substituted or unsubstituted, saturated or unsaturated carbocyclic ring having from 3 to 8 carbon atoms;

RP, $RB_4$, $RT_3$ and RB are independently selected from the group consisting of hydrogen, halo, $C_1$-$C_5$ alkyl, $C_1$-$C_5$ fluoroalkyl, —O—$C_1$-$C_5$ alkyl, —S—$C_1$-$C_5$ alkyl, —O—$C_1$-$C_5$ fluoroalkyl, —CN, —$NO_2$, acetyl, —S—$C_1$-$C_5$ fluoroalkyl, $C_2$-$C_5$ alkenyl, $C_3$-$C_5$ cycloalkyl, and $C_3$-$C_5$ cycloalkenyl;

$RP_3$ and $RB_7$ are independently selected from hydrogen, halo, $C_1$-$C_5$ alkyl, $C_1$-$C_5$ fluoroalkyl, —O—$C_1$-$C_5$ alkyl, —S—$C_1$-$C_5$ alkyl, —O—$C_1$-$C_5$ fluoroalkyl, —CN, —$NO_2$, acetyl, —S—$C_1$-$C_5$ fluoroalkyl, $C_2$-$C_5$ alkenyl, $C_3$-$C_5$ cycloalkyl, or $C_3$-$C_5$ cycloalkenyl;

($L_{P1}$), ($L_{P2}$), and ($L_{BT}$) are divalent linking groups independently selected from the group consisting of

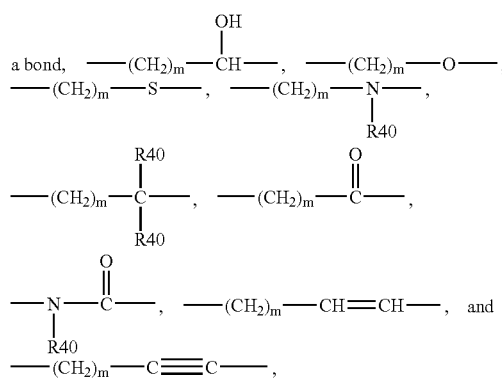

where m is 0, 1, or 2, and each R40 is independently hydrogen, $C_1$-$C_5$ alkyl, or $C_1$-$C_5$ fluoroalkyl;

$Z_P$ is branched $C_3$-$C_5$ alkyl,
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
1-hydroxy-2-methyl-1-(methylethyl)propyl,
2-methyl-3-hydroxy-4-dimethylpentyl,
2-methyl-3-hydroxy-3-ethylpentyl,
2-ethyl-3-hydroxy-3-ethylpentyl,
2-ethyl-3-hydroxy-4-dimethylpentyl,
3-methyl-3-hydroxy-4,4-dimethylpentyl,
3-methyl-3-hydroxy-4,4-dimethylpentenyl,
3-methyl-3-hydroxy-4,4-dimethylpentyl,
3-ethyl-3-hydroxy-4,4-dimethylpentynyl,
3-ethyl-3-hydroxy-4,4-dimethylpentenyl,
3-ethyl-3-hydroxy-4,4-dimethylpentynyl,
1-hydroxycycyclopentenyl,
1-hydroxycyclohexenyl,
1-hydroxycycloheptenyl,
1-hydroxycyclooctenyl,
1-hydroxycyclopropyl,
1-hydroxycyclobutyl,
1-hydroxycyclopentyl,
1-hydroxycyclohexyl,
2-oxocyclohexyloxy,
2-oxocyclohexylmethyl,
3-methyl-2-oxocyclohexyloxy,
3-methyl-2-oxocyclohexylmethyl,
3,3-dimethyl-2-oxocyclohexyloxy,
3,3-dimethyl-2-oxocyclohexylmethyl,
2-hydroxycyclohexyloxy,
2-hydroxycyclohexylmethyl,
3-methyl-2-hydroxycyclohexyloxy,
3-methyl-2-hydroxycyclohexylmethyl,
3,3-dimethyl-2-hydroxycyclohexyloxy,
3,3-dimethyl-2-hydroxycyclohexylmethyl,
1-hydroxycycloheptyl, or
1-hydroxycyclooctyl;

provided, however, that when $Z_P$ is 3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
3-methyl-3-hydroxy-4,4-dimethylpentyl,
3-methyl-3-hydroxy-4,4-dimethylpentenyl,
3-methyl-3-hydroxy-4,4-dimethylpentyl,
3-ethyl-3-hydroxy-4,4-dimethylpentynyl,
3-ethyl-3-hydroxy-4,4-dimethylpentenyl,
3-ethyl-3-hydroxy-4,4-dimethylpentynyl,
2-methyl-3-hydroxy-4-dimethylpentyl,
2-methyl-3-hydroxy-3-ethylpentyl,
2-ethyl-3-hydroxy-3-ethylpentyl,
2-ethyl-3-hydroxy-4-dimethylpentyl, or
1-hydroxy-2-methyl-1-(methylethyl)propyl;
then ($L_{P1}$) and ($L_{P2}$) combine as a bond;

$Z_{BT}$ is selected from
—O—($C_1$-$C_5$ alkyl),
—O—($C_2$-$C_5$ alkenyl),
—O—($C_3$-$C_5$ cycloalkyl),
—O—($C_3$-$C_5$ cycloalkenyl),
—O—($C_1$-$C_5$ hydroxyalkyl),
—O—($C_1$-$C_5$ fluoroalkyl),
—O—($C_1$-$C_5$ alkyl)-phenyl,
—O—($C_1$-$C_5$ alkyl)-(O)—($C_1$-$C_5$ alkyl),
—O—($C_1$-$C_5$ alkyl) $NH_2$,
—O—($C_1$-$C_5$ alkyl)-NH—($C_1$-$C_5$ alkyl)$_2$,
—O—($C_1$-$C_5$ alkyl)-C(O)—$NH_2$,
—O—($C_1$-$C_5$ alkyl)-C(O)—NH—($C_1$-$C_5$ alkyl),
—O—($C_1$-$C_5$ alkyl)-C(O)—N—($C_1$-$C_5$ alkyl)$_2$,
—O—($C_1$-$C_5$ alkyl)-C(O)—OH,
—O—($C_1$-$C_5$ alkyl)-C(O)—NH-5-tetrazolyl,
—O—($C_1$-$C_5$ alkyl)-C(O)—($C_1$-$C_5$ alkyl),
—O—($C_1$-$C_5$ alkyl)-C(O)—(O—$C_1$-$C_5$ alkyl),
—O—($C_1$-$C_5$ alkyl)-$NH_2$,
—O—($C_1$-$C_5$ alkyl)-NH—($C_1$-$C_5$ alkyl),
—O—($C_1$-$C_5$ alkyl)-N—($C_1$-$C_5$ alkyl)$_2$,
—O—($C_1$-$C_5$ alkyl)-NH—$SO_2$—($C_1$-$C_5$ alkyl),
—O—($C_1$-$C_5$ alkyl)-N-pyrrolidin-2-one,
—O—($C_1$-$C_5$ alkyl)-N-pyrrolidine,
—O—($C_1$-$C_5$ alkyl)-(1-methylpyrrolidin-2-one-3-yl),
—O—($C_1$-$C_5$ alkyl)-$SO_2$-($C_1$-$C_5$ alkyl,)
—O—($C_1$-$C_5$ alkyl)-$SO_2$—$NH_2$,
—O—($C_1$-$C_5$ alkyl)-$SO_2$—NH—($C_1$-$C_5$ alkyl),
—O—($C_1$-$C_5$ alkyl)-$SO_2$—N—($C_1$-$C_5$ alkyl)$_2$,
—O—($C_1$-$C_5$ alkyl)-$SO_2$—($C_1$-$C_5$ alkyl),
—O—($C_1$-$C_5$ alkyl)-S(O)—($C_1$-$C_5$ alkyl,)
—O—($C_1$-$C_5$ alkyl)-S(O)—$NH_2$,
—O—($C_1$-$C_5$ alkyl)-S(O)—NH—($C_1$-$C_5$ alkyl),
—O—($C_1$-$C_5$ alkyl)-S(O)—N—($C_1$-$C_5$ alkyl)$_2$,
—O—($C_1$-$C_5$ alkyl)-S(O)—($C_1$-$C_5$ alkyl),
—O—($C_1$-$C_5$ alkyl)-P(O)—(O—$C_1$-$C_5$ alkyl)$_2$,
—O—($C_1$-$C_5$ alkyl)-5-tetrazolyl,
—O—$CH_2$—$CO_2H$,
—O—$CH_2$-5-tetrazolyl,
—O—($C_1$-$C_5$ alkyl),
—O—C(O)—$NH_2$,
—O—C(O)—N—$(CH_3)_2$,
—O—C(S)—N—$(CH_3)_2$,
—O—C(O)—O—($C_1$-$C_5$ alkyl),
—O—(5-tetrazolyl),
—O—$SO_2$—($C_1$-$C_5$ alkyl,)
—O—$SO_2$—$NH_2$,
—O—$SO_2$—NH—($C_1$-$C_5$ alkyl),
—O—$SO_2$—N—($C_1$-$C_5$ alkyl)$_2$,
—O—S(O)—($C_1$-$C_5$ alkyl,)
—O—S(O)—$NH_2$,
—O—S(O)—NH—($C_1$-$C_5$ alkyl),
—O—S(O)—N—($C_1$-$C_5$ alkyl)$_2$,
—S—($C_1$-$C_5$ alkyl),
—S—($C_2$-$C_5$ alkenyl),
—S—($C_3$-$C_5$ cycloalkyl),
—S—($C_3$-$C_5$ cycloalkenyl),
—S—($C_1$-$C_5$ fluoroalkyl),
—S—($C_1$-$C_5$ hydroxyalkyl),
—S—($C_1$-$C_5$ alkyl)-phenyl,
—S—($C_1$-$C_5$ alkyl)-O—($C_1$-$C_5$ alkyl),
—S—($C_1$-$C_5$ alkyl)-C(O)—OH,
—S—($C_1$-$C_5$ alkyl)-C(O)—($C_1$-$C_5$ alkyl),
—S—($C_1$-$C_5$ alkyl)-C(O)—O—($C_1$-$C_5$ alkyl),
—S—($C_1$-$C_5$ alkyl)-C(O)—$NH_2$,
—S—($C_1$-$C_5$ alkyl)-C(O)—NH—($C_1$-$C_5$ alkyl),
—S—($C_1$-$C_5$ alkyl)-C(O)—N—($C_1$-$C_5$ alkyl)$_2$,
—S—($C_1$-$C_5$ alkyl) $NH_2$,
—S—($C_1$-$C_5$ alkyl)-NH—($C_1$-$C_5$ alkyl),
—S—($C_1$-$C_5$ alkyl)-N—($C_1$-$C_5$ alkyl)$_2$,
—S—($C_1$-$C_5$ alkyl)-NH—$SO_2$—($C_1$-$C_5$ alkyl),
—S—($C_1$-$C_5$ alkyl)-N-pyrrolidin-2-one,
—S—($C_1$-$C_5$ alkyl)-N-pyrrolidine,
—S—($C_1$-$C_5$ alkyl)-(1-methylpyrrolidin-2-one-3-yl),
—S—($C_1$-$C_5$ alkyl)-$SO_2$—($C_1$-$C_5$ alkyl),
—S—($C_1$-$C_5$ alkyl)-$SO_2$—$NH_2$,
—S—($C_1$-$C_5$ alkyl)-$SO_2$—NH—($C_1$-$C_5$ alkyl),
—S—($C_1$-$C_5$ alkyl)-$SO_2$—N—($C_1$-$C_5$ alkyl)$_2$,
—S—($C_1$-$C_5$ alkyl)-$SO_2$—($C_1$-$C_5$ alkyl),
—S—($C_1$-$C_5$ alkyl)-P(O)—(O—$C_1$-$C_5$ alkyl)$_2$,
—S—($C_1$-$C_5$ alkyl)-5-tetrazolyl,
—S—($C_1$-$C_5$ alkyl)-S(O)—($C_1$-$C_5$ alkyl),
—S—($C_1$-$C_5$ alkyl)-S(O)—$NH_2$,
—S—($C_1$-$C_5$ alkyl)-S(O)—NH—($C_1$-$C_5$ alkyl),
—S—($C_1$-$C_5$ alkyl)-S(O)—N—($C_1$-$C_5$ alkyl)$_2$,
—S—($C_1$-$C_5$ alkyl)-S(O)—($C_1$-$C_5$ alkyl),
—$SO_2$—($C_1$-$C_5$ alkyl),
—$SO_2$—($C_2$-$C_5$ alkenyl),
—$SO_2$—($C_3$-$C_5$ cycloalkyl),
—$SO_2$—($C_3$-$C_5$ cycloalkenyl),
—$SO_2$—($C_1$-$C_5$ hydroxyalkyl),
—$SO_2$—($C_1$-$C_5$ fluoroalkyl),
—$SO_2$—($C_1$-$C_5$)-phenyl,
—$SO_2$—$NH_2$,
—$SO_2$—NH—($C_1$-$C_5$ alkyl),
—$SO_2$—NH—$CH_2$—C(O)OH,
—$SO_2$—NH—$CH_2$—C(O)(O—$C_1$-$C_5$ alkyl),
—$SO_2$—NH—($C_1$-$C_5$ alkyl)-C(O)OH,
—$SO_2$—NH—($C_1$-$C_5$ alkyl)-C(O)(O—$C_1$-$C_5$ alkyl),
—$SO_2$—NHC(O)—($C_3$-$C_6$ cycloalkyl),
—$SO_2$—NH—C(O)—($C_1$-$C_5$ alkyl),
—$SO_2$—N—($C_1$-$C_5$ alkyl)$_2$,
—$SO_2$—($C_1$-$C_5$ alkyl)-O—($C_1$-$C_5$ alkyl),
—$SO_2$—($C_1$-$C_5$ alkyl)-C(O)—($C_1$-$C_5$ alkyl),
—$SO_2$—($C_1$-$C_5$ alkyl) $NH_2$,
—$SO_2$—($C_1$-$C_5$ alkyl)-NH—($C_1$-$C_5$ alkyl),
—$SO_2$—($C_1$-$C_5$ alkyl)-N—($C_1$-$C_5$ alkyl)$_2$,
—$SO_2$—($C_1$-$C_5$ alkyl)-C(O)—$NH_2$,
—$SO_2$—($C_1$-$C_5$ alkyl)-C(O)—NH—($C_1$-$C_5$ alkyl),
—$SO_2$—($C_1$-$C_5$ alkyl)-C(O)—N—($C_1$-$C_5$ alkyl)$_2$,
—$SO_2$—($C_1$-$C_5$ alkyl)-NH—$SO_2$—($C_1$-$C_5$ alkyl),
—$SO_2$—($C_1$-$C_5$ alkyl)-N-pyrrolidin-2-one,
—$SO_2$—($C_1$-$C_5$ alkyl)-N-pyrrolidine,
—$SO_2$—($C_1$-$C_5$ alkyl)-(1-methylpyrrolidin-2-one-3-yl),
—$SO_2$—($C_1$-$C_5$ alkyl)-C(O)—O—($C_1$-$C_5$ alkyl),
—$SO_2$—($C_1$-$C_5$ alkyl)-C(O)—OH,
—$SO_2$—($C_1$-$C_5$ alkyl)-5-tetrazolyl,
—$SO_2$—($C_1$-$C_5$ alkyl)-$SO_2$—($C_1$-$C_5$ alkyl),
—$SO_2$—($C_1$-$C_5$ alkyl)-$SO_2$—$NH_2$,
—$SO_2$—($C_1$-$C_5$ alkyl)-$SO_2$—NH—($C_1$-$C_5$ alkyl),
—$SO_2$—($C_1$-C5 alkyl)-$SO_2$—N—($C_1$-C5 alkyl)$_2$,
—$SO_2$—($C_1$-$C_5$ alkyl)-$SO_2$—($C_1$-$C_5$ alkyl),
—$SO_2$—($C_1$-$C_5$ alkyl)-P(O)—(O—$C_1$-$C_5$ alkyl)$_2$,
—$SO_2$—($C_1$-$C_5$ alkyl),
—$SO_2$—($C_2$-$C_5$ alkenyl),
—$SO_2$—($C_3$-$C_5$ cycloalkyl),
—$SO_2$—($C_3$-$C_5$ cycloalkenyl),
—$SO_2$—($C_1$-$C_5$ hydroxyalkyl),
—$SO_2$—($C_1$-$C_5$ fluoroalkyl),
—$SO_2$—($C_1$-$C_5$)-phenyl,
—$SO_2$—N=CHN($C_1$-$C_5$ alkyl)$_2$,
—S(O)—$NH_2$,
—S(O)—NH—($C_1$-$C_5$ alkyl),
—S(O)—NH—$CH_2$—C(O)OH —S(O)—NH—(C$_1$-C$_5$ alkyl)-C(O)OH,
—S(O)—NH—CH$_2$—C(O)(O—C$_1$-C$_5$ alkyl),
—S(O)—NH—(C$_1$-C$_5$ alkyl)-C(O)(O—C$_1$-C$_5$ alkyl),
—S(O)HC(O)—(C$_3$-C$_6$ cycloalkyl),
—S(O)—NH—C(O)—(C$_1$-C$_5$ alkyl),
—S(O)—N—(C$_1$-C$_5$ alkyl)$_2$,
—S(O)—(C$_1$-C$_5$ alkyl)-O—(C$_1$-C$_5$ alkyl),
—S(O)—(C$_1$-C$_5$ alkyl)-C(O)—(C$_1$-C$_5$ alkyl),
—S(O)—(C$_1$-C$_5$ alkyl)-C(O)—(O—C$_1$-C$_5$ alkyl),
—S(O)—(C$_1$-C$_5$ alkyl)-NH—(C$_1$-C$_5$ alkyl),
—S(O)—(C$_1$-C$_5$ alkyl)-N—(C$_1$-C$_5$ alkyl)$_2$,
—S(O)—(C$_1$-C$_5$ alkyl)-C(O)—NH$_2$,
—S(O)—(C$_1$-C$_5$ alkyl)-C(O)—NH—(C$_1$-C$_5$ alkyl),
—S(O)—(C$_1$-C$_5$ alkyl)-C(O)—N—(C$_1$-C$_5$ alkyl)$_2$,
—S(O)—(C$_1$-C$_5$ alkyl)-NH—SO$_2$—(C$_1$-C$_5$ alkyl),
—S(O)—(C$_1$-C$_5$ alkyl)-NH—S(O)—(C$_1$-C$_5$ alkyl),
—S(O)—(C$_1$-C$_5$ alkyl)-N-pyrrolidin-2-one,
—S(O)—(C$_1$-C$_5$ alkyl)-N-pyrrolidine,
—S(O)—(C$_1$-C$_5$ alkyl)-(1-methylpyrrolidin-2-one-3-yl),
—S(O)—(C$_1$-C$_5$ alkyl)-C(O)—(O—C$_1$-C$_5$ alkyl),
—S(O)—(C$_1$-C$_5$ alkyl)-C(O)—OH,
—S(O)—(C$_1$-C$_5$ alkyl)-5-tetrazolyl,
—S(O)—(C$_1$-C$_5$ alkyl)-SO$_2$—(C$_1$-C$_5$ alkyl),
—S(O)—(C$_1$-C$_5$ alkyl)-S(O)—(C$_1$-C$_5$ alkyl),
—S(O)—(C$_1$-C$_5$ alkyl)-SO$_2$—NH$_2$,
—S(O)—(C$_1$-C$_5$ alkyl)-S(O)—NH$_2$,
—S(O)—(C$_1$-C$_5$ alkyl)-SO$_2$—NH—(C$_1$-C$_5$ alkyl),
—S(O)—(C$_1$-C$_5$ alkyl)-S(O)—NH—(C$_1$-C$_5$ alkyl),
—S(O)—(C$_1$-C5 alkyl)-SO$_2$—N—(C$_1$-C$_5$ alkyl)$_2$,
—S(O)—(C$_1$-C 5 alkyl)-S(O)—N—(C$_1$-C$_5$ alkyl)$_2$,
—S(O)—(C$_1$-C$_5$ alkyl)-SO$_2$—(C$_1$-C$_5$ alkyl),
—S(O)—(C$_1$-C$_5$ alkyl)-S(O)—(C$_1$-C$_5$ alkyl),
—S(O)—(C$_1$-C$_5$ alkyl)-P(O)—(O—C$_1$-C$_5$ alkyl)$_2$,
—S(O)—N=CHN(C$_1$-C$_5$ alkyl)$_2$,
—NHC(S)NH$_2$,
—NHC(S)NH—(C$_1$-C$_5$ alkyl),
—NHC(S)N—(C$_1$-C$_5$ alkyl)$_2$,
—NHC(S)NH—(C$_2$-C$_5$ alkenyl),
—NHC(S)NH—(C$_3$-C$_5$ cycloalkyl),
—NHC(S)NH—(C$_3$-C$_5$ cycloalkenyl),
—NHC(S)NH—(C$_1$-C$_5$ fluoroalkyl),
—NHC(S)NH—C$_1$-C$_5$ hydroxyalkyl,
—NHC(S)NH—(C$_1$-C$_5$ fluoroalkyl)
—NHC(S)NH-phenyl,
—NHC(S)NH—(C$_1$-C$_5$ alkyl)-C(O)—OH,
—NHC(S)NH—(C$_1$-C$_5$ alkyl)-O—(C$_1$-C$_5$ alkyl),
—NHC(S)NH—(C$_1$-C$_5$ alkyl)-C(O)—(C$_1$-C$_5$ alkyl),
—NHC(S)NH—(C$_1$-C$_5$ alkyl)-C(O)—(O—C$_1$-C$_5$ alkyl),
—NHC(S)NH—(C$_1$-C$_5$ alkyl)-NH$_2$,
—NHC(S)NH—(C$_1$-C$_5$ alkyl)-NH—(C$_1$-C$_5$ alkyl),
—NHC(S)NH—(C$_1$-C$_5$ alkyl)-N—(C$_1$-C$_5$ alkyl)$_2$,
—NHC(S)NH—(C$_1$-C$_5$ alkyl)-C(O)—NH$_2$,
—NHC(S)NH—(C$_1$-C$_5$ alkyl)-C(O)—NH—(C$_1$-C$_5$ alkyl),
—NHC(S)NH—(C$_1$-C$_5$ alkyl)-C(O)—N—(C$_1$-C$_5$ alkyl)$_2$,
—NHC(S)NH—(C$_1$-C$_5$ alkyl)-NH—SO$_2$—(C$_1$-C$_5$ alkyl),
—NHC(S)NH—(C$_1$-C$_5$ alkyl)-NH—S(O)—(C$_1$-C$_5$ alkyl),
—NHC(S)NH—(C$_1$-C$_5$ alkyl)-N-pyrrolidin-2-one,
—NHC(S)NH—(C$_1$-C$_5$ alkyl)-N-pyrrolidine,
—NHC(S)NH—(C$_1$-C$_5$ alkyl)-(1-methylpyrrolidin-2-one-3-yl),
—NHC(S)NH—(C$_1$-C$_5$ alkyl)-5-tetrazolyl,
—NHC(S)NH—(C$_1$-C$_5$ alkyl)-SO$_2$—(C$_1$-C$_5$ alkyl),
—NHC(S)NH—(C$_1$-C$_5$ alkyl)-SO$_2$—NH$_2$,
—NHC(S)NH—(C$_1$-C$_5$ alkyl)-SO$_2$—NH—(C$_1$-C$_5$ alkyl),
—NHC(S)NH—(C$_1$-C$_5$ alkyl)-SO$_2$—N—(C$_1$-C$_5$ alkyl)$_2$,
—NHC(S)NH—(C$_1$-C$_5$ alkyl)-S(O)—(C$_1$-C$_5$ alkyl),
—NHC(S)NH—(C$_1$-C$_5$ alkyl)-S(O)—NH$_2$,
—NHC(S)NH—(C$_1$-C$_5$ alkyl)-S(O)—NH—(C$_1$-C$_5$ alkyl),
—NHC(S)NH—(C$_1$-C$_5$ alkyl)-S(O)—N—(C$_1$-C$_5$ alkyl)$_2$,
—NHC(S)NH—(C$_1$-C$_5$ alkyl)-P(O)—(O—C$_1$-C$_5$ alkyl)$_2$,
—NHC(O)NH$_2$,
—NHC(O)NH—(C$_1$-C$_5$ alkyl),
—NHC(O)N—(C$_1$-C$_5$ alkyl)$_2$,
—NHC(O)NH—(C$_2$-C$_5$ alkenyl),
—NHC(O)NH—(C$_3$-C$_5$ cycloalkyl),
—NHC(O)NH—(C$_3$-C$_5$ cycloalkenyl),
—NHC(O)NH—(C$_1$-C$_5$ hydroxyalkyl),
—NHC(O)NH—(C$_1$-C$_5$ fluoroalkyl),
—NHC(O)NH-phenyl,
—NHC(O)NH—(C$_1$-C$_5$ alkyl)-NH$_2$,
—NHC(O)NH—(C$_1$-C$_5$ alkyl)-NH—(C$_1$-C$_5$ alkyl),
—NHC(O)NH—(C$_1$-C$_5$ alkyl)-N—(C$_1$-C$_5$ alkyl)$_2$,
—NHC(O)NH—(C$_1$-C$_5$ alkyl)-O—(C$_1$-C$_5$ alkyl),
—NHC(O)NH—(C$_1$-C$_5$ alkyl)-NH$_2$,
—NHC(O)NH—(C$_1$-C$_5$ alkyl)-NH—(C$_1$-C$_5$ alkyl),
—NHC(O)NH—(C$_1$-C$_5$ alkyl)-N—(C$_1$-C$_5$ alkyl)$_2$,
—NHC(O)NH—(C$_1$-C$_5$ alkyl)-C(O)—NH$_2$,
—NHC(O)NH—(C$_1$-C$_5$ alkyl)-C(O)—NH—(C$_1$-C$_5$ alkyl),
—NHC(O)NH—(C$_1$-C$_5$ alkyl)-C(O)—N—(C$_1$-C$_5$ alkyl)$_2$,
—NHC(O)NH—(C$_1$-C$_5$ alkyl)-C(O)—(C$_1$-C$_5$ alkyl),
—NHC(O)NH—(C$_1$-C$_5$ alkyl)-NH—SO$_2$—(C$_1$-C$_5$ alkyl),
—NHC(O)NH—(C$_1$-C$_5$ alkyl)-N-pyrrolidin-2-one,
—NHC(O)NH—(C$_1$-C$_5$ alkyl)-N-pyrrolidine,
—NHC(O)NH—(C$_1$-C$_5$ alkyl)-(1-methylpyrrolidin-2-one-3-yl),
—NHC(O)NH—(C$_1$-C$_5$ alkyl)-C(O)—OH,
—NHC(O)NH—(C$_1$-C$_5$ alkyl)-C(O)—O—(C$_1$-C$_5$ alkyl),
—NHC(O)NH—(C$_1$-C$_5$ alkyl)-5-tetrazolyl,
—NHC(O)NH—(C$_1$-C$_5$ alkyl)-SO$_2$—(C$_1$-C$_5$ alkyl),
—NHC(O)NH—(C$_1$-C$_5$ alkyl)-SO$_2$—NH$_2$,
—NHC(O)NH—(C$_1$-C$_5$ alkyl)-SO$_2$—NH—(C$_1$-C$_5$ alkyl),
—NHC(O)NH—(C$_1$-C$_5$ alkyl)-SO$_2$—N—(C$_1$-C$_5$ alkyl)$_2$,
—NHC(O)NH—(C$_1$-C$_5$ alkyl)-P(O)—O—(C$_1$-C$_5$ alkyl)$_2$,
—NH$_2$,
—NH—(C$_1$-C$_5$ alkyl),
—NH—CH$_2$—C(O)OH,
—N—(C$_1$-C$_5$ alkyl)$_2$,
—NH—C(O)—NH$_2$,
—NH—C(O)—NH—(C$_1$-C$_5$ alkyl),
—NH—C(O)—N—(C$_1$-C$_5$ alkyl)$_2$,
—NH—C(O)—(C$_1$-C$_5$ alkyl),
—NH—SO$_2$—(C$_1$-C$_5$ alkyl),
—NH—S(O)—(C$_1$-C$_5$ alkyl),
—N(CH$_3$)(OCH$_3$),
—N(OH)(CH$_3$),
—N-pyrrolidin-2-one,
—N-pyrrolidine,
-(1-methylpyrrolidin-2-one-3-yl),
—CO$_2$H,
—CO$_2$Me,
—CO$_2$Et,
—C(O)CH$_2$S(O)Me,
—C(O)CH$_2$S(O)Et,
—C(O)CH$_2$S(O)$_2$Me,
—C(O)CH$_2$S(O)$_2$Et,
—C(O)CH$_2$CH$_2$S(O)Me, —C(O)CH₂CH₂S(O)Et,
—C(O)CH₂CH₂S(O)₂Me,
—C(O)CH₂CH₂S(O)₂Et,
—C(O)CH(Me)CH₂CO₂H,
—C(O)CH(Me)CH₂CO₂Me,
—C(O)CH(Me)CH2CO₂Et,
—C(O)CH(Me)CH₂CO₂iPr,
—C(O)CH(Me)CH₂CO2tBu,
—C(O)CH(Me)CH(Me)CO₂H,
—C(O)CH(Me)CH(Me)CO₂Me,
—C(O)CH(Me)CH(Me)CO₂Et,
—C(O)CH(Me)CH(Me)CO₂iPr,
—C(O)CH(Me)CH(Me)Co₂tBu,
—C(O)CH(Me)C(Me)₂CO₂H,
—C(O)CH(Me)C(Me)₂CO₂Me,
—C(O)CH(Me)C(Me)₂CO₂Et,
—C(O)CH(Me)C(Me)₂CO₂iPr,
—C(O)CH(Me)C(Me)₂CO₂tBu,
—C(O)CH(Me)CH(Et)CO₂H,
—C(O)CH(Me)CH(Et)CO₂Me,
—C(O)CH(Me)CH(Et)CO₂Et,
—C(O)CH(Me)CH(Et)CO₂iPr,
—C(O)CH(Me)CH(Et)CO₂tBu,
—C(O)C(O)OH,
—C(O)C(O)NH₂,
—C(O)C(O)NHMe,
—C(O)C(O)NMe₂,
—C(O)NH₂,
—C(O)NMe₂,
—C(O)NH—CH₂—C(O)OH,
—C(O)NH—CH₂—C(O)OMe,
—C(O)NH—CH₂—C(O)OEt,
—C(O)NH—CH₂—C(O)OiPr,
—C(O)NH—CH₂—C(O)OtBu,
—C(O)NH—CH(Me)-C(O)OH,
—C(O)NH—CH(Me)-C(O)OMe,
—C(O)NH—CH(Me)-C(O)OEt,
—C(O)NH—CH(Me)-C(O)iPr,
—C(O)NH—CH(Me)-C(O)tBu,
—C(O)NH—CH(Et)-C(O)OH,
—C(O)NH—C(Me)₂-C(O)OH,
—C(O)NH—C(Me)₂-C(O)OMe,
—C(O)NH—C(Me)₂-C(O)OEt,
—C(O)NH—C(Me)₂-C(O)iPr,
—C(O)NH—C(Me)₂-C(O)tBu,
—C(O)NH—CMe(Et)-C(O)OH,
—C(O)NH—CH(F)—C(O)OH,
—C(O)NH—CH(CF₃)—C(O)OH,
—C(O)NH—CH(OH)—C(O)OH,
—C(O)NH—CH(cyclopropyl)-C(O)OH,
—C(O)NH—C(Me)₂-C(O)OH,
—C(O)NH—C(Me)₂-C(O)OH,
—C(O)NH—CF(Me)-C(O)OH,
—C(O)NH—C(Me)(CF₃)—C(O)OH,
—C(O)NH—C(Me)(OH)—C(O)OH,
—C(O)NH—C(Me)(cyclopropyl)CO₂H
—C(O)NMe-CH₂—C(O)OH,
—C(O)NMe-CH₂—C(O)OMe,
—C(O)NMe-CH₂—C(O)OEt,
—C(O)NMe-CH₂—C(O)OiPr,
—C(O)NMe-CH₂—C(O)tBu,
—C(O)NMe-CH₂—C(O)OH,
—C(O)NMe-CH(Me)-C(O)OH,
—C(O)NMe-CH(F)—C(O)OH,
—C(O)NMe-CH(CF₃)—C(O)OH,
—C(O)NMe-CH(OH)—C(O)OH,
—C(O)NMe-CH(cyclopropyl)-C(O)OH,
—C(O)NMe-C(Me)₂-C(O)OH,
—C(O)NMe-CF(Me)-C(O)OH,
—C(O)NMe-C(Me)(CF₃)—C(O)OH,
—C(O)NMe-C(Me)(OH)—C(O)OH,
—C(O)NMe-C(Me)(cyclopropyl)-C(O)OH,
—C(O)NHS(O)Me,
—C(O)NHSO₂Me,
—C(O)—NH-5-tetrazolyl,
—C(O)NHS(O)Me,
—C(O)NHS(O)Et,
—C(O)NHSO₂Me,
—C(O)NHSO₂Et,
—C(O)NHS(O)iPr,
—C(O)NHSO₂iPr,
—C(O)NHS(O)tBu,
—C(O)NHSO₂tBu,
—C(O)NHCH₂S(O)Me,
—C(O)NHCH₂S(O)Et,
—C(O)NHCH₂SO₂Me,
—C(O)NHCH₂SO₂Et,
—C(O)NHCH₂CH₂S(O)Me,
—C(O)NHCH₂CH₂S(O)Et,
—C(O)NHCH₂CH₂SO₂Me,
—C(O)NHCH₂CH₂SO₂Et,
—C(O)N(Me)S(O)Me,
—C(O)N(Me)SO₂Me,
—C(O)—N(Me)-5-tetrazolyl,
—C(O)N(Me)S(O)Me,
—C(O)N(Me)S(O)Et,
—C(O)N(Me)SO₂Me,
—C(O)N(Me)SO₂Et,
—C(O)N(Me)S(O)iPr,
—C(O)N(Me))SO₂iPr,
—C(O)N(Me)S(O)tBu,
—C(O)N(Me)SO₂tBu,
—C(O)N(Me)CH₂S(O)Me,
—C(O)N(Me)CH₂S(O)Et,
—C(O)N(Me)CH₂SO₂Me,
—C(O)N(Me)CH₂SO₂Et,
—C(O)N(Me)CH₂CH₂S(O)Me,
—C(O)N(Me)CH₂CH₂S(O)Et,
—C(O)N(Me)CH₂CH₂SO₂Me,
—C(O)N(Me)CH₂CH₂SO₂Et,
—CH₂CO₂H,
—CH₂-5-tetrazolyl,
—CH₂CO₂Me,
—CH₂CO₂Et,
—CH₂NHS(O)Me,
—CH₂NHS(O)Et,
—CH₂NHSO₂Me,
—CH₂NHSO₂Et,
—CH₂NHS(O)iPr,
—CH₂NHSO₂iPr,
—CH₂NHS(O)tBu,
—CH₂NHSO₂tBu,
—CH₂NHCH₂CH₂SO₂CH₃,
—CH₂NH(CH₂CO₂H),
—CH₂N(C(O)Me)(CH₂CO₂H),
—CH₂—N-pyrrolidin-2-one,
—CH₂-(1-methylpyrrolidin-2-one-3-yl),
—CH₂S(O)Me,
—CH₂S(O)Et,
—CH₂S(O)₂Me,
—CH₂S(O)₂Et,
—CH₂S(O)iPr,
—CH₂S(O)₂iPr,
—CH₂S(O)tBu, —CH₂S(O)₂tBu,
—CH₂CO₂H, CH₂C(O)NH₂,
—CH₂C(O)NMe₂,
—CH₂C(O)NHMe,
—CH₂C(O)—N-pyrrolidine,
—CH₂S(O)₂Me, CH₂S(O)Me,
—CH(OH)CO₂H,
—CH(OH)C(O)NH₂,
—CH(OH)C(O)NHMe,
—CH(OH)C(O)NMe₂,
—CH(OH)C(O)NEt₂,
—CH₂CH₂CO₂H,
—CH₂CH₂CO₂Me,
—CH₂CH₂CO₂Et,
—CH₂CH₂C(O)NH₂,
—CH₂CH₂C(O)NHMe,
—CH₂CH₂C(O)NMe₂,
—CH₂CH₂-5-tetrazolyl,
—CH₂CH₂S(O)₂Me,
—CH₂CH₂S(O)Me,
—CH₂CH₂S(O)₂Et,
—CH₂CH₂S(O)Et,
—CH₂CH₂S(O)iPr,
—CH₂CH₂S(O)₂iPr,
—CH₂CH₂S(O)tBu,
—CH₂CH₂S(O)₂tBu,
—CH₂CH₂S(O)NH₂,
—CH₂CH₂S(O)NHMe,
—CH₂CH₂S(O)NMe₂,
—CH₂CH₂S(O)₂NH₂,
—CH₂CH₂S(O)₂NHMe,
—CH₂CH₂S(O)₂NMe₂,
—CH₂CH₂CH₂S(O)Me,
—CH₂CH₂CH₂S(O)Et,
—CH₂CH₂CH₂S(O)₂Me,
—CH₂CH₂CH₂S(O)₂Et,
—CH(Me)CH₂C(O)OH,
—C(Me)₂CH₂C(O)OH,
-5-tetrazolyl,

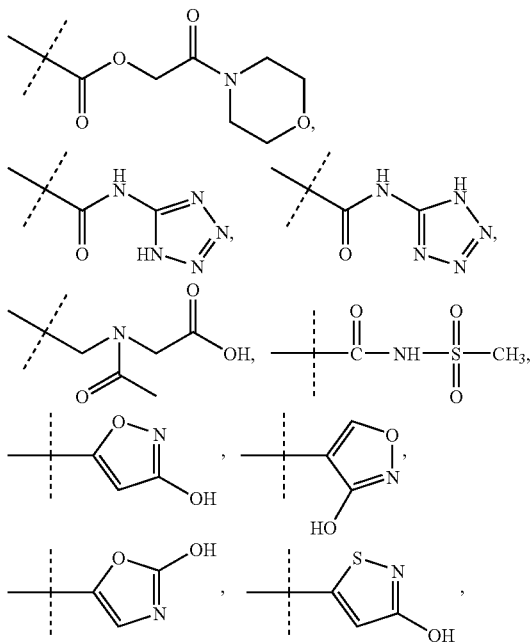

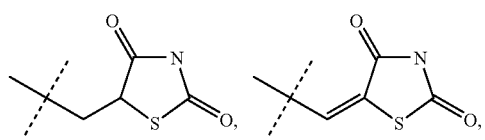

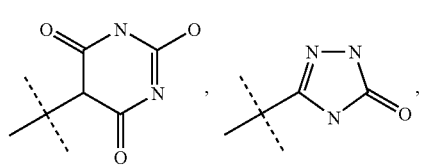

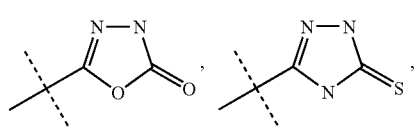

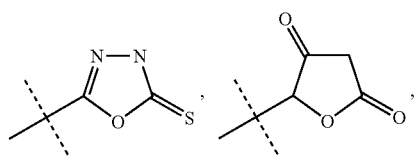

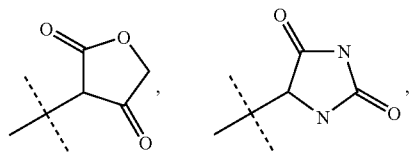

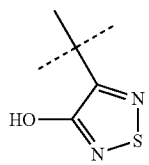

-1,3,4-oxadiazolin-2-one-5-yl,
-imidazolidine-2,4-dione-5-yl,
-isoxazol-3-ol-yl, or
-1,3,4-oxadiazolin-2-thione-5-yl;

provided that RP is substituted at either the 2, 5, or 6 position of the phenyl ring.

The compounds of the invention with vitamin receptor modulating (VDRM) activity are represented by formula (IC) or a pharmaceutically acceptable salt or a prodrug derivative thereof:

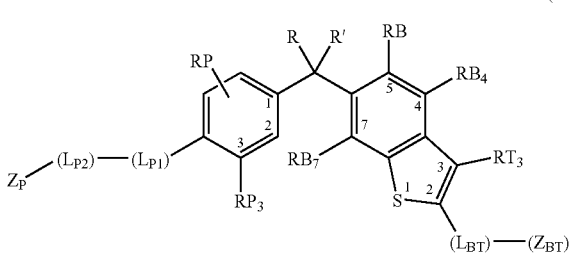

(IC)

wherein

R and R' are independently $C_1$-$C_5$ alkyl, $C_1$-$C_5$ fluoroalkyl, or together R and R' form a substituted or unsubstituted, saturated or unsaturated carbocyclic ring having from 3 to 8 carbon atoms;

RP, $RB_4$, $RT_3$ and RB are independently selected from the group consisting of hydrogen, halo, $C_1$-$C_5$ alkyl, $C_1$-$C_5$ fluoroalkyl, —O—$C_1$-$C_5$ alkyl, —S—$C_1$-$C_5$ alkyl, —O—$C_1$-$C_5$ fluoroalkyl, —CN, —$NO_2$, acetyl, —S—$C_1$-$C_5$ fluoroalkyl, $C_2$-$C_5$ alkenyl, $C_3$-$C_5$ cycloalkyl, and $C_3$-$C_5$ cycloalkenyl;

$RP_3$ and $RB_7$ are independently selected from hydrogen, halo, $C_1$-$C_5$ alkyl, $C_1$-$C_5$ fluoroalkyl, —O—$C_1$-$C_5$ alkyl, —S—$C_1$-$C_5$ alkyl, —O—$C_1$-$C_5$ fluoroalkyl, —CN, —$NO_2$, acetyl, —S—$C_1$-$C_5$ fluoroalkyl, $C_2$-$C_5$ alkenyl, $C_3$-$C_5$ cycloalkyl, or $C_3$-$C_5$ cycloalkenyl;

$(L_{P1})$, $(L_{P2})$, and $(L_{BT})$ are divalent linking groups independently selected from the group consisting of

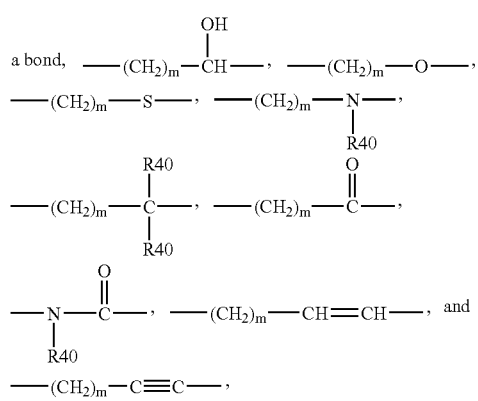

where m is 0, 1, or 2, and each R40 is independently hydrogen, $C_1$-$C_5$ alkyl, or $C_1$-$C_5$ fluoroalkyl;

$Z_P$ is
branched $C_3$-$C_5$ alkyl,
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
1-hydroxy-2-methyl-1-(methylethyl)propyl,
2-methyl-3-hydroxy-4-dimethylpentyl,
2-methyl-3-hydroxy-3-ethylpentyl,
2-ethyl-3-hydroxy-3-ethylpentyl,
2-ethyl-3-hydroxy-4-dimethylpentyl,
3-methyl-3-hydroxy-4,4-dimethylpentyl,
3-methyl-3-hydroxy-4,4-dimethylpentenyl,
3-methyl-3-hydroxy-4,4-dimethylpentyl,
3-ethyl-3-hydroxy-4,4-dimethylpentynyl,
3-ethyl-3-hydroxy-4,4-dimethylpentenyl,
3-ethyl-3-hydroxy-4,4-dimethylpentynyl,
1-hydroxycycyclopentenyl,
1-hydroxycyclohexenyl,
1-hydroxycycloheptenyl,
1-hydroxycyclooctenyl,
1-hydroxycyclopropyl,
1-hydroxycyclobutyl,
1-hydroxycyclopentyl,
1-hydroxycyclohexyl,
2-oxocyclohexyloxy,
2-oxocyclohexylmethyl,
3-methyl-2-oxocyclohexyloxy,
3-methyl-2-oxocyclohexylmethyl,
3,3-dimethyl-2-oxocyclohexyloxy,
3,3-dimethyl-2-oxocyclohexylmethyl,
2-hydroxycyclohexyloxy,
2-hydroxycyclohexylmethyl,
3-methyl-2-hydroxycyclohexyloxy,
3-methyl-2-hydroxycyclohexylmethyl,
3,3-dimethyl-2-hydroxycyclohexyloxy,
3,3-dimethyl-2-hydroxycyclohexylmethyl,
1-hydroxycycloheptyl, or
1-hydroxycyclooctyl;

provided, however, that when
$Z_P$ is
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
3-methyl-3-hydroxy-4,4-dimethylpentyl,
3-methyl-3-hydroxy-4,4-dimethylpentenyl,
3-methyl-3-hydroxy-4,4-dimethylpentyl,
3-ethyl-3-hydroxy-4,4-dimethylpentynyl,
3-ethyl-3-hydroxy-4,4-dimethylpentenyl,
3-ethyl-3-hydroxy-4,4-dimethylpentynyl,
2-methyl-3-hydroxy-4-dimethylpentyl,
2-methyl-3-hydroxy-3-ethylpentyl,
2-ethyl-3-hydroxy-3-ethylpentyl,
2-ethyl-3-hydroxy-4-dimethylpentyl, or
1-hydroxy-2-methyl-1-(methylethyl)propyl;
then $(L_{P1})$ and $(L_{P2})$ combine as a bond;

$Z_{BT}$ is selected from
—O—($C_1$-$C_5$ alkyl),
—O—($C_2$-$C_5$ alkenyl),
—O—($C_3$-$C_5$ cycloalkyl),
—O—($C_3$-$C_5$ cycloalkenyl),
—O—($C_1$-$C_5$ hydroxyalkyl),
—O—($C_1$-$C_5$ fluoroalkyl), —O—($C_1$-$C_5$ alkyl)-phenyl,
—O—($C_1$-$C_5$ alkyl)-(O)—($C_1$-$C_5$ alkyl),
—O—($C_1$-$C_5$ alkyl) $NH_2$,
—O—($C_1$-$C_5$ alkyl)-NH—($C_1$-$C_5$ alkyl)$_2$,
—O—($C_1$-$C_5$ alkyl)-C(O)—$NH_2$,
—O—($C_1$-$C_5$ alkyl)-C(O)—NH—($C_1$-$C_5$ alkyl),
—O—($C_1$-$C_5$ alkyl)-C(O)—N—($C_1$-$C_5$ alkyl)$_2$,
—O—($C_1$-$C_5$ alkyl)-C(O)—OH,
—O—($C_1$-$C_5$ alkyl)-C(O)—NH-5-tetrazolyl,
—O—($C_1$-$C_5$ alkyl)-C(O)—($C_1$-$C_5$ alkyl),
—O—($C_1$-$C_5$ alkyl)-C(O)—(O—$C_1C_5$ alkyl),
—O—($C_1$-$C_5$ alkyl)-$NH_2$,
—O—($C_1$-$C_5$ alkyl)-NH—($C_1$-$C_5$ alkyl),
—O—($C_1$-$C_5$ alkyl)-N—($C_1$-$C_5$ alkyl)$_2$,
—O—($C_1$-$C_5$ alkyl)-NH—$SO_2$—($C_1$-$C_5$ alkyl),
—O—($C_1$-$C_5$ alkyl)-N-pyrrolidin-2-one,
—O—($C_1$-$C_5$ alkyl)-N-pyrrolidine,
—O—($C_1$-$C_5$ alkyl)-(1-methylpyrrolidin-2-one-3-yl),
—O—($C_1$-$C_5$ alkyl)-$SO_2$—($C_1$-$C_5$ alkyl,)
—O—($C_1$-$C_5$ alkyl)-$SO_2$—$NH_2$,
—O—($C_1$-$C_5$ alkyl)-$SO_2$—NH—($C_1$-$C_5$ alkyl),
—O—($C_1$-$C_5$ alkyl)-$SO_2$—N—($C_1$-$C_5$ alkyl)$_2$,
—O—($C_1$-$C_5$ alkyl)-$SO_2$—($C_1$-$C_5$ alkyl),
—O—($C_1$-$C_5$ alkyl)-S(O)—($C_1$-$C_5$ alkyl,)
—O—($C_1$-$C_5$ alkyl)-S(O)—$NH_2$,
—O—($C_1$-$C_5$ alkyl)-S(O)—NH—($C_1$-$C_5$ alkyl),
—O—($C_1$-$C_5$ alkyl)-S(O)—N—($C_1$-$C_5$ alkyl)$_2$,
—O—($C_1$-$C_5$ alkyl)-S(O)—($C_1$-$C_5$ alkyl),
—O—($C_1$-$C_5$ alkyl)-P(O)—(O—$C_1$-$C_5$ alkyl)$_2$,
—O—($C_1$-$C_5$ alkyl)-5-tetrazolyl,
—O—$CH_2$—$CO_2H$,
—O—$CH_2$-5-tetrazolyl,
—O—($C_1$-$C_5$ alkyl),
—O—C(O)—$NH_2$,
—O—C(O)—N—$(CH_3)_2$,
—O—C(S)—N—$(CH_3)_2$,
—O—C(O)—O—($C_1$-$C_5$ alkyl),
—O-(5-tetrazolyl),
—O—$SO_2$—($C_1$-$C_5$ alkyl,)
—O—$SO_2$—$NH_2$,
—O—$SO_2$—NH—($C_1$-$C_5$ alkyl),
—O—$SO_2$—N—($C_1$-$C_5$ alkyl)$_2$,
—O—S(O)—($C_1$-$C_5$ alkyl,)
—O—S(O)—$NH_2$,
—O—S(O)—NH—($C_1$-$C_5$ alkyl),
—O—S(O)—N—($C_1$-$C_5$ alkyl)$_2$,
—S—($C_1$-$C_5$ alkyl),
—S—($C_2$-$C_5$ alkenyl),
—S—($C_3$-$C_5$ cycloalkyl),
—S—($C_3$-$C_5$ cycloalkenyl),
—S—($C_1$-$C_5$ fluoroalkyl),
—S—($C_1$-$C_5$ hydroxyalkyl),
—S—($C_1$-$C_5$ alkyl)-phenyl,
—S—($C_1$-$C_5$ alkyl)-O—($C_1$-$C_5$ alkyl),
—S—($C_1$-$C_5$ alkyl)-C(O)—OH,
—S—($C_1$-$C_5$ alkyl)-C(O)—($C_1$-$C_5$ alkyl),
—S—($C_1$-$C_5$ alkyl)-C(O)—O—($C_1$-$C_5$ alkyl),
—S—($C_1$-$C_5$ alkyl)-C(O)—$NH_2$,
—S—($C_1$-$C_5$ alkyl)-C(O)—NH—($C_1$-$C_5$ alkyl),
—S—($C_1$-$C_5$ alkyl)-C(O)—N—($C_1$-$C_5$ alkyl)$_2$,
—S—($C_1$-$C_5$ alkyl) $NH_2$,
—S—($C_1$-$C_5$ alkyl)-NH—($C_1$-$C_5$ alkyl),
—S—($C_1$-$C_5$ alkyl)-N—($C_1$-$C_5$ alkyl)$_2$,
—S—($C_1$-$C_5$ alkyl)-NH—$SO_2$—($C_1$-$C_5$ alkyl),
—S—($C_1$-$C_5$ alkyl)-N-pyrrolidin-2-one,
—S—($C_1$-$C_5$ alkyl)-N-pyrrolidine,
—S—($C_1$-$C_5$ alkyl)-(1-methylpyrrolidin-2-one-3-yl),
—S—($C_1$-$C_5$ alkyl)-$SO_2$—($C_1$-C5 alkyl),
—S—($C_1$-$C_5$ alkyl)-$SO_2$—$NH_2$,
—S—($C_1$-$C_5$ alkyl)-$SO_2$—NH—($C_1$-$C_5$ alkyl),
—S—($C_1$-$C_5$ alkyl)-$SO_2$—N—($C_1$-$C_5$ alkyl)$_2$,
—S—($C_1$-$C_5$ alkyl)-$SO_2$—($C_1$-$C_5$ alkyl),
—S—($C_1$-$C_5$ alkyl)-P(O)—(O—$C_1$-$C_5$ alkyl)$_2$,
—S—($C_1$-$C_5$ alkyl)-5-tetrazolyl,
—S—($C_1$-$C_5$ alkyl)-S(O)—($C_1$-$C_5$ alkyl),
—S—($C_1$-$C_5$ alkyl)-S(O)—$NH_2$,
—S—($C_1$-$C_5$ alkyl)-S(O)—NH—($C_1$-$C_5$ alkyl),
—S—($C_1$-$C_5$ alkyl)-S(O)—N—($C_1$-$C_5$ alkyl)$_2$,
—S—($C_1$-$C_5$ alkyl)-S(O)—($C_1$-$C_5$ alkyl),
—$SO_2$—($C_1$-$C_5$ alkyl),
—$SO_2$—($C_2$-$C_5$ alkenyl),
—$SO_2$—($C_3$-$C_5$ cycloalkyl),
—$SO_2$—($C_3$-$C_5$ cycloalkenyl),
—$SO_2$—($C_1$-$C_5$ hydroxyalkyl),
—$SO_2$—($C_1$-$C_5$ fluoroalkyl),
—$SO_2$—($C_1$-$C_5$)-phenyl,
—$SO_2$—$NH_2$,
—$SO_2$—NH—($C_1$-$C_5$ alkyl),
—$SO_2$—NH—$CH_2$—C(O)OH,
—$SO_2$—NH—$CH_2$—C(O)(O—$C_1$-$C_5$ alkyl),
—$SO_2$—NH—($C_1$-$C_5$ alkyl)-C(O)OH,
—$SO_2$—NH—($C_1$-$C_5$ alkyl)-C(O)(O—$C_1$-$C_5$ alkyl),
—$SO_2$—NHC(O)—($C_3$-$C_6$ cycloalkyl),
—$SO_2$—NH—C(O)—($C_1$-$C_5$ alkyl),
—$SO_2$—N—($C_1$-$C_5$ alkyl)$_2$,
—$SO_2$—($C_1$-$C_5$ alkyl)-O—($C_1$-$C_5$ alkyl),
—$SO_2$—($C_1$-$C_5$ alkyl)-C(O)—($C_1$-$C_5$ alkyl),
—$SO_2$—($C_1$-$C_5$ alkyl) $NH_2$,
—$SO_2$—($C_1$-$C_5$ alkyl)-NH—($C_1$-$C_5$ alkyl),
—$SO_2$—($C_1$-$C_5$ alkyl)-N—($C_1$-$C_5$ alkyl)$_2$,
—$SO_2$—($C_1$-$C_5$ alkyl)-C(O)—$NH_2$,
—$SO_2$—($C_1$-$C_5$ alkyl)-C(O)—NH—($C_1$-$C_5$ alkyl),
—$SO_2$—($C_1$-$C_5$ alkyl)-C(O)—N—($C_1$-$C_5$ alkyl)$_2$,
—$SO_2$—($C_1$-$C_5$ alkyl)-NH—$SO_2$—($C_1$-$C_5$ alkyl),
—$SO_2$—($C_1$-$C_5$ alkyl)-N-pyrrolidin-2-one,
—$SO_2$—($C_1$-$C_5$ alkyl)-N-pyrrolidine,
—$SO_2$—($C_1$-$C_5$ alkyl)-(1-methylpyrrolidin-2-one-3-yl),
—$SO_2$—($C_1$-$C_5$ alkyl)-C(O)—O—($C_1$-$C_5$ alkyl),
—$SO_2$—($C_1$-$C_5$ alkyl)-C(O)—OH,
—$SO_2$—($C_1$-$C_5$ alkyl)-5-tetrazolyl,
—$SO_2$—($C_1$-$C_5$ alkyl)-$SO_2$—($C_1$-$C_5$ alkyl),
—$SO_2$—($C_1$-$C_5$ alkyl)-$SO_2$—$NH_2$,
—$SO_2$—($C_1$-$C_5$ alkyl)-$SO_2$—NH—($C_1$-$C_5$ alkyl),
—$SO_2$—($C_1$-C5 alkyl)-$SO_2$—N—($C_1$-C5 alkyl)$_2$,
—$SO_2$—($C_1$-$C_5$ alkyl)-$SO_2$—($C_1$-$C_5$ alkyl),
—$SO_2$—($C_1$-$C_5$ alkyl)-P(O)—(O—$C_1C_5$ alkyl)$_2$,
—$SO_2$—($C_1$-$C_5$ alkyl),
—$SO_2$—($C_2$-$C_5$ alkenyl),
—$SO_2$—($C_3$-$C_5$ cycloalkyl),
—$SO_2$—($C_3$-$C_5$ cycloalkenyl),
—$SO_2$—($C_1$-$C_5$ hydroxyalkyl),
—$SO_2$—($C_1$-$C_5$ fluoroalkyl),
—$SO_2$—($C_1$-$C_5$)-phenyl,
—$SO_2$—N=CHN($C_1$-$C_5$ alkyl)$_2$,
—S(O)—$NH_2$,
—S(O)—NH—($C_1$-$C_5$ alkyl),
—S(O)—NH—$CH_2$—C(O)OH
—S(O)—NH—($C_1$-$C_5$ alkyl)-C(O)OH,
—S(O)—NH—$CH_2$—C(O)(O—$C_1$-$C_5$ alkyl),
—S(O)—NH—($C_1$-$C_5$ alkyl)-C(O)(O—$C_1$-$C_5$ alkyl),
—S(O)HC(O)—($C_3$-$C_6$ cycloalkyl),
—S(O)—NH—C(O)—($C_1$-$C_5$ alkyl),
—S(O)—N—($C_1$-$C_5$ alkyl)$_2$,
—S(O)—($C_1$-$C_5$ alkyl)-O—($C_1$-$C_5$ alkyl), —S(O)—(C₁-C₅ alkyl)-C(O)—(C₁-C₅ alkyl),
—S(O)—(C₁-C₅ alkyl)-C(O)—(O—C₁-C₅ alkyl),
—S(O)—(C₁-C₅ alkyl)-NH—(C₁-C₅ alkyl),
—S(O)—(C₁-C₅ alkyl)-N—(C₁-C₅ alkyl)₂,
—S(O)—(C₁-C₅ alkyl)-C(O)—NH₂,
—S(O)—(C₁-C₅ alkyl)-C(O)—NH—(C₁-C₅ alkyl),
—S(O)—(C₁-C₅ alkyl)-C(O)—N—(C₁-C₅ alkyl)₂,
—S(O)—(C₁-C₅ alkyl)-NH—SO₂—(C₁-C₅ alkyl),
—S(O)—(C₁-C₅ alkyl)-NH—S(O)—(C₁-C₅ alkyl),
—S(O)—(C₁-C₅ alkyl)-N-pyrrolidin-2-one,
—S(O)—(C₁-C₅ alkyl)-N-pyrrolidine,
—S(O)—(C₁-C₅ alkyl)-(1-methylpyrrolidin-2-one-3-yl),
—S(O)—(C₁-C₅ alkyl)-C(O)—(O—C₁-C₅ alkyl),
—S(O)—(C₁-C₅ alkyl)-C(O)—OH,
—S(O)—(C₁-C₅ alkyl)-5-tetrazolyl,
—S(O)—(C₁-C₅ alkyl)-SO₂—(C₁-C₅ alkyl),
—S(O)—(C-₁-C₅ alkyl)-S(O)—(C₁-C₅ alkyl),
—S(O)—(C₁-C₅ alkyl)-SO₂—NH₂,
—S(O)—(C₁-C₅ alkyl)-S(O)—NH₂,
—S(O)—(C₁-C₅ alkyl)-SO₂—NH—(C₁-C₅ alkyl),
—S(O)—(C₁-C₅ alkyl)-S(O)—NH—(C₁-C₅ alkyl),
—S(O)—(C₁-C₅ alkyl)-SO₂—N—(C₁-C₅ alkyl)₂,
—S(O)—(C₁-C₅ alkyl)-S(O)—N—(C₁-C₅ alkyl)₂,
—S(O)—(C₁-C₅ alkyl)-SO₂—(C₁-C₅ alkyl),
—S(O)—(C₁-C₅ alkyl)-S(O)—(C₁-C₅ alkyl),
—S(O)—(C₁-C₅ alkyl)-P(O)—(O—C₁-C₅ alkyl)₂,
—S(O)—N═CHN(C₁-C₅ alkyl)₂,
—NHC(S)NH₂,
—NHC(S)NH—(C₁-C₅ alkyl),
—NHC(S)N—(C₁-C₅ alkyl)₂,
—NHC(S)NH—(C₂-C₅ alkenyl),
—NHC(S)NH—(C₃-C₅ cycloalkyl),
—NHC(S)NH—(C₃-C₅ cycloalkenyl),
—NHC(S)NH—(C₁-C₅ fluoroalkyl),
—NHC(S)NH—C₁-C₅ hydroxyalkyl,
—NHC(S)NH—C₁-C₅ fluoroalkyl
—NHC(S)NH-phenyl,
—NHC(S)NH—(C₁-C₅ alkyl)-C(O)—OH,
—NHC(S)NH—(C₁-C₅ alkyl)-O—(C₁-C₅ alkyl),
—NHC(S)NH—(C₁-C₅ alkyl)-C(O)—(C₁-C₅ alkyl),
—NHC(S)NH—(C₁-C₅ alkyl)-C(O)—(O—C₁-C₅ alkyl),
—NHC(S)NH—(C₁-C₅ alkyl)-NH₂,
—NHC(S)NH—(C₁-C₅ alkyl)-NH—(C₁-C₅ alkyl),
—NHC(S)NH—(C₁-C₅ alkyl)-N—(C₁-C₅ alkyl)₂,
—NHC(S)NH—(C₁-C₅ alkyl)-C(O)—NH₂,
—NHC(S)NH—(C₁-C₅ alkyl)-C(O)—NH—(C₁-C₅ alkyl),
—NHC(S)NH—(C₁-C₅ alkyl)-C(O)—N—(C₁-C₅ alkyl)₂,
—NHC(S)NH—(C₁-C₅ alkyl)-NH—SO₂—(C₁-C₅ alkyl),
—NHC(S)NH—(C₁-C₅ alkyl)-NH—S(O)—(C₁-C₅ alkyl),
—NHC(S)NH—(C₁-C₅ alkyl)-N-pyrrolidin-2-one,
—NHC(S)NH—(C₁-C₅ alkyl)-N-pyrrolidine,
—NHC(S)NH—(C₁-C₅ alkyl)-(1-methylpyrrolidin-2-one-3-yl),
—NHC(S)NH—(C₁-C₅ alkyl)-5-tetrazolyl,
—NHC(S)NH—(C₁-C₅ alkyl)-SO₂—(C₁-C₅ alkyl),
—NHC(S)NH—(C₁-C₅ alkyl)-SO₂—NH₂,
—NHC(S)NH—(C₁-C₅ alkyl)-SO₂—NH—(C₁-C₅ alkyl),
—NHC(S)NH—(C₁-C₅ alkyl)-SO₂—N—(C₁-C₅ alkyl)₂,
—NHC(S)NH—(C₁-C₅ alkyl)-S(O)—(C₁-C₅ alkyl),
—NHC(S)NH—(C₁-C₅ alkyl)-S(O)—NH₂,
—NHC(S)NH—(C₁-C₅ alkyl)-S(O)—NH—(C₁-C₅ alkyl),
—NHC(S)NH—(C₁-C₅ alkyl)-S(O)—N—(C₁-C₅ alkyl)₂,
—NHC(S)NH—(C₁-C₅ alkyl)-P(O)—(O—C₁C₅ alkyl)₂,
—NHC(O)NH₂,
—NHC(O)NH—(C₁-C₅ alkyl),
—NHC(O)N—(C₁-C₅ alkyl)₂,
—NHC(O)NH—(C₂-C₅ alkenyl),
—NHC(O)NH—(C₃-C₅ cycloalkyl),
—NHC(O)NH—(C₃-C₅ cycloalkenyl),
—NHC(O)NH—(C₁-C₅ hydroxyalkyl),
—NHC(O)NH—(C₁-C₅ fluoroalkyl),
—NHC(O)NH-phenyl,
—NHC(O)NH—(C₁-C₅ alkyl)-NH₂,
—NHC(O)NH—(C₁-C₅ alkyl)-NH—(C₁-C₅ alkyl),
—NHC(O)NH—(C₁-C₅ alkyl)-N—(C₁-C₅ alkyl)₂,
—NHC(O)NH—(C₁-C₅ alkyl)-O—(C₁-C₅ alkyl),
—NHC(O)NH—(C₁-C₅ alkyl)-NH₂,
—NHC(O)NH—(C₁-C₅ alkyl)-NH—(C₁-C₅ alkyl),
—NHC(O)NH—(C₁-C₅ alkyl)-N—(C₁-C₅ alkyl)₂,
—NHC(O)NH—(C₁-C₅ alkyl)-C(O)—NH₂,
—NHC(O)NH—(C₁-C₅ alkyl)-C(O)—NH—(C₁-C₅ alkyl),
—NHC(O)NH—(C₁-C₅ alkyl)-C(O)—N—(C₁-C₅ alkyl)₂,
—NHC(O)NH—(C₁-C₅ alkyl)-C(O)—(C₁-C₅ alkyl),
—NHC(O)NH—(C₁-C₅ alkyl)-NH—SO₂—(C₁-C₅ alkyl),
—NHC(O)NH—(C₁-C₅ alkyl)-N-pyrrolidin-2-one,
—NHC(O)NH—(C₁-C₅ alkyl)-N-pyrrolidine,
—NHC(O)NH—(C₁-C₅ alkyl)-(1-methylpyrrolidin-2-one-3-yl),
—NHC(O)NH—(C₁-C₅ alkyl)-C(O)—OH,
—NHC(O)NH—(C₁-C₅ alkyl)-C(O)—O—(C₁-C₅ alkyl),
—NHC(O)NH—(C₁-C₅ alkyl)-5-tetrazolyl,
—NHC(O)NH—(C₁-C₅ alkyl)-SO₂—(C₁-C₅ alkyl),
—NHC(O)NH—(C₁-C₅ alkyl)-SO₂—NH₂,
—NHC(O)NH—(C₁-C₅ alkyl)-SO₂—NH—(C₁-C₅ alkyl),
—NHC(O)NH—(C₁-C₅ alkyl)-SO₂—N—(C₁-C₅ alkyl)₂,
—NHC(O)NH—(C₁-C₅ alkyl)-P(O)—O—(C₁-C₅ alkyl)₂,
—NH₂,
—NH—(C₁-C₅ alkyl),
—NH—CH₂—C(O)OH,
—N—(C₁-C₅ alkyl)₂,
—NH—C(O)—NH₂,
—NH—C(O)—NH—(C₁-C₅ alkyl),
—NH—C(O)—N—(C₁-C₅ alkyl)₂,
—NH—C(O)—(C₁-C₅ alkyl),
—NH—SO₂—(C₁-C₅ alkyl),
—NH—S(O)—(C₁-C₅ alkyl),
—N(CH₃)(OCH₃),
—N(OH)(CH₃),
—N-pyrrolidin-2-one,
—N-pyrrolidine,
-(1-methylpyrrolidin-2-one-3-yl),
—CO₂H,
—CO₂Me,
—CO₂Et,
—C(O)CH₂S(O)Me,
—C(O)CH₂S(O)Et,
—C(O)CH₂S(O)₂Me,
—C(O)CH₂S(O)₂Et,
—C(O)CH₂CH₂S(O)Me,
—C(O)CH₂CH₂S(O)Et,
—C(O)CH₂CH₂S(O)₂Me,
—C(O)CH₂CH₂S(O)₂Et,
—C(O)CH(Me)CH₂CO₂H,
—C(O)CH(Me)CH₂CO₂Me,
—C(O)CH(Me)CH₂CO₂Et,
—C(O)CH(Me)CH₂CO₂iPr, —C(O)CH(Me)CH₂CO₂tBu,
—C(O)CH(Me)CH(Me)CO₂H,
—C(O)CH(Me)CH(Me)CO₂Me,
—C(O)CH(Me)CH(Me)CO₂Et,
—C(O)CH(Me)CH(Me)CO₂iPr,
—C(O)CH(Me)CH(Me)CO₂tBu,
—C(O)CH(Me)C(Me)₂CO₂H,
—C(O)CH(Me)C(Me)₂CO₂Me,
—C(O)CH(Me)C(Me)₂CO₂Et,
—C(O)CH(Me)C(Me)₂CO₂iPr,
—C(O)CH(Me)C(Me)₂CO₂tBu,
—C(O)CH(Me)CH(Et)CO₂H,
—C(O)CH(Me)CH(Et)CO₂Me,
—C(O)CH(Me)CH(Et)CO₂Et,
—C(O)CH(Me)CH(Et)CO₂iPr,
—C(O)CH(Me)CH(Et)CO₂tBu,
—C(O)C(O)OH,
—C(O)C(O)NH₂,
—C(O)C(O)NHMe,
—C(O)C(O)NMe₂,
—C(O)NH₂,
—C(O)NMe₂,
—C(O)NH—CH₂—C(O)OH,
—C(O)NH—CH₂—C(O)OMe,
—C(O)NH—CH₂—C(O)OEt,
—C(O)NH—CH₂—C(O)OiPr,
—C(O)NH—CH₂—C(O)OtBu,
—C(O)NH—CH(Me)-C(O)OH,
—C(O)NH—CH(Me)-C(O)OMe,
—C(O)NH—CH(Me)-C(O)OEt,
—C(O)NH—CH(Me)-C(O)iPr,
—C(O)NH—CH(Me)-C(O)tBu,
—C(O)NH—CH(Et)-C(O)OH,
—C(O)NH—C(Me)₂-C(O)OH,
—C(O)NH—C(Me)₂-C(O)OMe,
—C(O)NH—C(Me)₂-C(O)OEt,
—C(O)NH—C(Me)₂-C(O)iPr,
—C(O)NH—C(Me)₂-C(O)tBu,
—C(O)NH—CMe(Et)-C(O)OH,
—C(O)NH—CH(F)—C(O)OH,
—C(O)NH—CH(CF₃)—C(O)OH,
—C(O)NH—CH(OH)—C(O)OH,
—C(O)NH—CH(cyclopropyl)-C(O)OH,
—C(O)NH—C(Me)₂-C(O)OH,
—C(O)NH—C(Me)₂-C(O)OH,
—C(O)NH—CF(Me)-C(O)OH,
—C(O)NH—C(Me)(CF₃)—C(O)OH,
—C(O)NH—C(Me)(OH)—C(O)OH,
—C(O)NH—C(Me)(cyclopropyl)CO₂H
—C(O)NMe-CH₂—C(O)OH,
—C(O)NMe-CH₂—C(O)OMe,
—C(O)NMe-CH₂—C(O)OEt,
—C(O)NMe-CH₂—C(O)OiPr,
—C(O)NMe-CH₂—C(O)tBu,
—C(O)NMe-CH₂—C(O)OH,
—C(O)NMe-CH(Me)-C(O)OH,
—C(O)NMe-CH(F)—C(O)OH,
—C(O)NMe-CH(CF₃)—C(O)OH,
—C(O)NMe-CH(OH)—C(O)OH,
—C(O)NMe-CH(cyclopropyl)-C(O)OH,
—C(O)NMe-C(Me)₂-C(O)OH,
—C(O)NMe-CF(Me)-C(O)OH,
—C(O)NMe-C(Me)(CF₃)—C(O)OH,
—C(O)NMe-C(Me)(OH)—C(O)OH,
—C(O)NMe-C(Me)(cyclopropyl)-C(O)OH,
—C(O)NHS(O)Me,
—C(O)NHSO₂Me,
—C(O)—NH-5-tetrazolyl,
—C(O)NHS(O)Me,
—C(O)NHS(O)Et,
—C(O)NHSO₂Me,
—C(O)NHSO₂Et,
—C(O)NHS(O)iPr,
—C(O)NHSO₂iPr,
—C(O)NHS(O)tBu,
—C(O)NHSO₂tBu,
—C(O)NHCH₂S(O)Me,
—C(O)NHCH₂S(O)Et,
—C(O)NHCH₂SO₂Me;
—C(O)NHCH₂SO₂Et,
—C(O)NHCH₂CH₂S(O)Me,
—C(O)NHCH₂CH₂S(O)Et,
—C(O)NHCH₂CH₂SO₂Me,
—C(O)NHCH₂CH₂SO₂Et,
—C(O)N(Me)S(O)Me,
—C(O)N(Me)SO₂Me,
—C(O)—N(Me)-5-tetrazolyl,
—C(O)N(Me)S(O)Me,
—C(O)N(Me)S(O)Et,
—C(O)N(Me)SO₂Me,
—C(O)N(Me)SO₂Et,
—C(O)N(Me)S(O)iPr,
—C(O)N(Me))SO₂iPr,
—C(O)N(Me))S(O)tBu,
—C(O)N(Me)SO₂tBu,
—C(O)N(Me)CH₂S(O)Me,
—C(O)N(Me)CH₂S(O)Et,
—C(O)N(Me)CH₂SO₂Me,
—C(O)N(Me)CH₂SO₂Et,
—C(O)N(Me)CH₂CH₂S(O)Me,
—C(O)N(Me)CH₂CH₂S(O)Et,
—C(O)N(Me)CH₂CH₂SO₂Me,
—C(O)N(Me)CH₂CH₂SO₂Et,
—CH₂CO₂H,
—CH₂-5-tetrazolyl,
—CH₂CO₂Me,
—CH₂CO₂Et,
—CH₂NHS(O)Me,
—CH₂NHS(O)Et,
—CH₂NHSO₂Me,
—CH₂NHSO₂Et,
—CH₂NHS(O)iPr,
—CH₂NHSO₂iPr,
—CH₂NHS(O)tBu,
—CH₂NHSO₂tBu,
—CH₂NHCH₂CH₂SO₂CH₃,
—CH₂NH(CH₂CO₂H),
—CH₂N(C(O)Me)(CH₂CO₂H),
—CH₂-N-pyrrolidin-2-one,
—CH₂-(1-methylpyrrolidin-2-one-3-yl),
—CH₂S(O)Me,
—CH₂S(O)Et,
—CH₂S(O)₂Me,
—CH₂S(O)₂Et,
—CH₂S(O)iPr,
—CH₂S(O)₂iPr,
—CH₂S(O)tBu,
—CH₂S(O)₂tBu,
—CH₂CO₂H, CH₂C(O)NH₂,
—CH₂C(O)NMe₂,
—CH₂C(O)NHMe,
—CH₂C(O)-N-pyrrolidine,
—CH₂S(O)₂Me, CH₂S(O)Me,
—CH(OH)CO₂H, —CH(OH)C(O)NH₂,
—CH(OH)C(O)NHMe,
—CH(OH)C(O)NMe₂,
—CH(OH)C(O)NEt₂,
—CH₂CH₂CO₂H,
—CH₂CH₂CO₂Me,
—CH₂CH₂CO₂Et,
—CH₂CH₂C(O)NH₂,
—CH₂CH₂C(O)NHMe,
—CH₂CH₂C(O)NMe₂,
—CH₂CH₂-5-tetrazolyl,
—CH₂CH₂S(O)₂Me,
—CH₂CH₂S(O)Me,
—CH₂CH₂S(O)₂Et,
—CH₂CH₂S(O)Et,
—CH₂CH₂S(O)iPr,
—CH₂CH₂S(O)₂iPr,
—CH₂CH₂S(O)tBu,
—CH₂CH₂S(O)₂tBu,
—CH₂CH₂S(O)NH₂,
—CH₂CH₂S(O)NHMe,
—CH₂CH₂S(O)NMe₂,
—CH₂CH₂S(O)₂NH₂,
—CH₂CH₂S(O)₂NHMe,
—CH₂CH₂S(O)₂NMe₂,
—CH₂CH₂CH₂S(O)Me,
—CH₂CH₂CH₂S(O)Et,
—CH₂CH₂CH₂S(O)₂Me,
—CH₂CH₂CH₂S(O)₂Et,
CH(Me)CH₂C(O)OH,
—C(Me)₂CH₂C(O)OH,
-5-tetrazolyl,

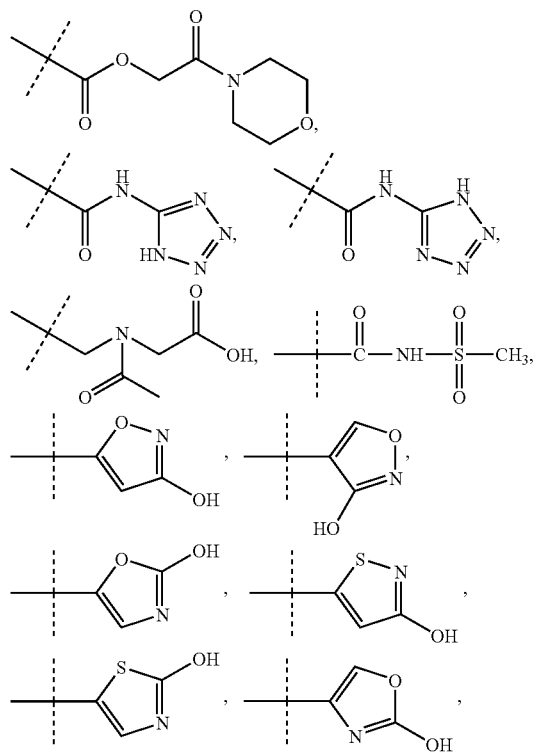

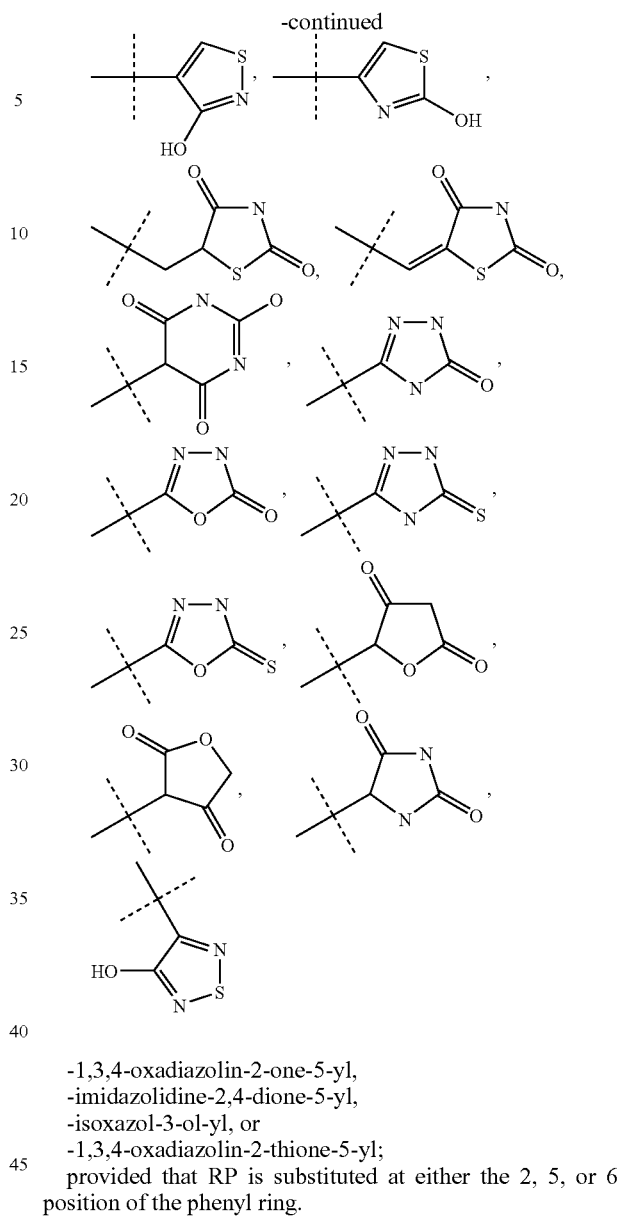

-1,3,4-oxadiazolin-2-one-5-yl,
-imidazolidine-2,4-dione-5-yl,
-isoxazol-3-ol-yl, or
-1,3,4-oxadiazolin-2-thione-5-yl;
provided that RP is substituted at either the 2, 5, or 6 position of the phenyl ring.

Preferred Embodiments of the Invention:
The compound of Formula IA having as preferred substituents;
R and R' are independently methy or ethyl;
RP and RT₃ are independently, hydrogen or methyl;
RP₃ and RB are independently hydrogen, methyl, ethyl, —O-methyl, or cyclopropyl;
($L_{P1}$) and ($L_{TB}$) divalent linking groups are both bonds;
($L_{P2}$) is a bond, —CH₂—, —CH(OH)—, or —C(Me)OH—;
$Z_P$ is 1,1-dimethylethyl; 1-hydroxycyclopentyl, 1-hydroxycyclohexyl, 3-ethyl-3-hydroxypentyl, 3-ethyl-3-hydroxypentenyl, 3-ethyl-3-hydroxypentynyl;
$Z_{TB}$ is
—CO₂H,
—CO₂Me,
—CO₂Et,
—C(O)CH₂S(O)Me,
—C(O)CH₂S(O)Et,
—C(O)CH₂S(O)₂Me, —C(O)CH₂S(O)₂Et,
—C(O)CH₂CH₂S(O)Me,
—C(O)CH₂CH₂S(O)Et,
—C(O)CH₂CH₂S(O)₂Me,
—C(O)CH₂CH₂S(O)₂Et,
—C(O)CH(Me)CH₂CO₂H,
—C(O)CH(Me)CH₂CO₂Me,
—C(O)CH(Me)CH₂CO₂Et,
—C(O)CH(Me)CH₂CO₂iPr,
—C(O)CH(Me)CH₂CO₂tBu,
—C(O)CH(Me)CH(Me)CO₂H,
—C(O)CH(Me)CH(Me)CO₂Me,
—C(O)CH(Me)CH(Me)CO₂Et,
—C(O)CH(Me)CH(Me)CO₂iPr,
—C(O)CH(Me)CH(Me)CO₂tBu,
—C(O)CH(Me)C(Me)₂CO₂H
—C(O)CH(Me)C(Me)₂CO₂Me,
—C(O)CH(Me)C(Me)₂CO₂Et,
—C(O)CH(Me)C(Me)₂CO₂iPr,
—C(O)CH(Me)C(Me)₂CO₂tBu,
—C(O)CH(Me)CH(Et)CO₂H,
—C(O)CH(Me)CH(Et)CO₂Me,
—C(O)CH(Me)CH(Et)CO₂Et,
—C(O)CH(Me)CH(Et)CO₂iPr,
—C(O)CH(Me)CH(Et)CO₂tBu,
—C(O)C(O)OH,
—C(O)C(O)NH₂,
—C(O)C(O)NHMe,
—C(O)C(O)NMe₂,
—C(O)NH₂,
—C(O)NMe₂,
—C(O)NH—CH₂—C(O)OH,
—C(O)NH—CH₂—C(O)OMe,
—C(O)NH—CH₂—C(O)OEt,
—C(O)NH—CH₂—C(O)OiPr,
—C(O)NH—CH₂—C(O)OtBu,
—C(O)NH—CH₂—C(O)OH,
—C(O)NH—CH(Me)-C(O)OMe,
—C(O)NH—CH(Me)-C(O)OEt,
—C(O)NH—CH(Me)-C(O)iPr,
—C(O)NH—CH(Me)-C(O)tBu,
—C(O)NH—CH(Et)-C(O)OH,
—C(O)NH—C(Me)₂-C(O)OH,
—C(O)NH—C(Me)₂-C(O)OMe,
—C(O)NH—C(Me)₂-C(O)OEt,
—C(O)NH—C(Me)₂-C(O)iPr,
—C(O)NH—C(Me)₂-C(O)tBu,
—C(O)NH—CMe(Et)-C(O)OH,
—C(O)NH—CH(F)—C(O)OH,
—C(O)NH—CH(CF₃)—C(O)OH,
—C(O)NH—CH(OH)—C(O)OH,
—C(O)NH—CH(cyclopropyl)-C(O)OH,
—C(O)NH—C(Me)₂-C(O)OH,
—C(O)NH—C(Me)₂-C(O)OH,
—C(O)NH—CF(Me)-C(O)OH,
—C(O)NH—C(Me)(CF₃)—C(O)OH,
—C(O)NH—C(Me)(OH)—C(O)OH,
—C(O)NH—C(Me)(cyclopropyl)CO₂H
—C(O)NMe-CH₂—C(O)OH,
—C(O)NMe-CH₂—C(O)OMe,
—C(O)NMe-CH₂—C(O)OEt,
—C(O)NMe-CH₂—C(O)OiPr,
—C(O)NMe-CH₂—C(O)tBu,
—C(O)NMe-CH₂—C(O)OH,
—C(O)NMe-CH(Me)-C(O)(OH),
—C(O)NMe-CH(F)—C(O)OH,
—C(O)NMe-CH(CF₃)—C(O)OH,
—C(O)NMe-CH(OH)—C(O)OH,
—C(O)NMe-CH(cyclopropyl)-C(O)OH,
—C(O)NMe-C(Me)₂-C(O)OH,
—C(O)NMe-CF(Me)-C(O)OH,
—C(O)NMe-C(Me)(CF₃)—C(O)OH,
—C(O)NMe-C(Me)(OH)—C(O)OH,
—C(O)NMe-C(Me)(cyclopropyl)-C(O)OH,
—C(O)NHS(O)Me,
—C(O)NHSO₂Me,
—C(O)—NH-5-tetrazolyl,
—C(O)NHS(O)Me,
—C(O)NHS(O)Et,
—C(O)NHSO₂Me,
—C(O)NHSO₂Et,
—C(O)NHS(O)iPr,
—C(O)NHSO₂iPr,
—C(O)NHS(O)tBu,
—C(O)NHSO₂tBu,
—C(O)NHCH₂S(O)Me,
—C(O)NHCH₂S(O)Et,
—C(O)NHCH₂SO₂Me,
—C(O)NHCH₂SO₂Et,
—C(O)NHCH₂CH₂S(O)Me,
—C(O)NHCH₂CH₂S(O)Et,
—C(O)NHCH₂CH₂SO₂Me,
—C(O)NHCH₂CH₂SO₂Et,
—C(O)N(Me)S(O)Me,
—C(O)N(Me)SO₂Me,
—C(O)—N(Me)-5-tetrazolyl,
—C(O)N(Me)S(O)Me,
—C(O)N(Me)S(O)Et,
—C(O)N(Me)SO₂Me,
—C(O)N(Me)SO₂Et,
—C(O)N(Me)S(O)iPr,
—C(O)N(Me))SO₂iPr,
—C(O)N(Me)S(O)tBu,
—C(O)N(Me)SO₂tBu,
—C(O)N(Me)CH₂S(O)Me,
—C(O)N(Me)CH₂S(O)Et,
—C(O)N(Me)CH₂SO₂Me,
—C(O)N(Me)CH₂SO₂Et,
—C(O)N(Me)CH₂CH₂S(O)Me,
—C(O)N(Me)CH₂CH₂S(O)Et,
—C(O)N(Me)CH₂CH₂SO₂Me,
—C(O)N(Me)CH₂CH₂SO₂Et,
—CH₂CO₂H,
—CH₂-5-tetrazolyl,
—CH₂CO₂Me,
—CH₂CO₂Et,
—CH₂NHS(O)Me,
—CH₂NHS(O)Et,
—CH₂NHSO₂Me,
—CH₂NHSO₂Et,
—CH₂NHS(O)iPr,
—CH₂NHSO₂iPr,
—CH₂NHS(O)tBu,
—CH₂NHSO₂tBu,
—CH₂NHCH₂CH₂SO₂CH₃,
—CH₂NH(CH₂CO₂H),
—CH₂N(C(O)Me)(CH₂CO₂H),
—CH₂—N-pyrrolidin-2-one,
—CH₂-(1-methylpyrrolidin-2-one-3-yl),
—CH₂S(O)Me,
—CH₂S(O)Et,
—CH₂S(O)₂Me,
—CH₂S(O)₂Et,
—CH₂S(O)iPr, —CH$_2$S(O)$_2$iPr,
—CH$_2$S(O)tBu,
—CH$_2$S(O)$_2$tBu,
—CH$_2$CO$_2$H, CH$_2$C(O)NH$_2$,
—CH$_2$C(O)NMe$_2$,
—CH$_2$C(O)NHMe,
—CH$_2$C(O)—N-pyrrolidine,
—CH$_2$S(O)$_2$Me, CH$_2$S(O)Me,
—CH(OH)CO$_2$H,
—CH(OH)C(O)NH$_2$,
—CH(OH)C(O)NHMe,
—CH(OH)C(O)NMe$_2$,
—CH(OH)C(O)NEt$_2$,
—CH$_2$CH$_2$CO$_2$H,
—CH$_2$CH$_2$CO$_2$Me,
—CH$_2$CH$_2$CO$_2$Et,
—CH$_2$CH$_2$C(O)NH$_2$,
—CH$_2$CH$_2$C(O)NHMe,
—CH$_2$CH$_2$C(O)NMe$_2$,
—CH$_2$CH$_2$-5-tetrazolyl,
—CH$_2$CH$_2$S(O)$_2$Me,
—CH$_2$CH$_2$S(O)Me,
—CH$_2$CH$_2$S(O)$_2$Et,
—CH$_2$CH$_2$S(O)Et,
—CH$_2$CH$_2$S(O)iPr,
—CH$_2$CH$_2$S(O)$_2$iPr,
—CH$_2$CH$_2$S(O)tBu,
—CH$_2$CH$_2$S(O)$_2$tBu,
—CH$_2$CH$_2$S(O)NH$_2$,
—CH$_2$CH$_2$S(O)NHMe,
—CH$_2$CH$_2$S(O)NMe$_2$,
—CH$_2$CH$_2$S(O)$_2$NH$_2$,
—CH$_2$CH$_2$S(O)$_2$NHMe
—CH$_2$CH$_2$S(O)$_2$NMe$_2$,
—CH$_2$CH$_2$CH$_2$S(O)Me,
—CH$_2$CH$_2$CH$_2$S(O)Et,
—CH$_2$CH$_2$CH$_2$S(O)$_2$Me, or
—CH$_2$CH$_2$CH$_2$S(O)$_2$Et.

The compound of formula IB having as preferred substituents;
R and R' are independently methy or ethyl;
RP, RB, RB$_4$, and RT$_3$ are independently, hydrogen or methyl;
RP$_3$ and RB$_7$ are independently hydrogen, methyl, ethyl, —O-methyl, or cyclopropyl;
(L$_{P1}$) and (L$_{BT}$) divalent linking groups are both bonds;
(L$_{P2}$) is a bond, —CH$_2$—, —CH(OH)—, or —C(Me)OH—;
Z$_P$ is 1,1-dimethylethyl; 1-hydroxycyclopentyl, 1-hydroxycyclohexyl, 3-ethyl-3-hydroxypentyl, 3-ethyl-3-hydroxypentenyl, 3-ethyl-3-hydroxypentynyl;
Z$_{BT}$ is
—CO$_2$H,
—CO$_2$Me,
—CO$_2$Et,
—C(O)CH$_2$S(O)Me,
—C(O)CH$_2$S(O)Et,
—C(O)CH$_2$S(O)$_2$Me,
—C(O)CH$_2$S(O)$_2$Et,
—C(O)CH$_2$CH$_2$S(O)Me,
—C(O)CH$_2$CH$_2$S(O)Et,
—C(O)CH$_2$CH$_2$S(O)$_2$Me,
—C(O)CH$_2$CH$_2$S(O)$_2$Et,
—C(O)CH(Me)CH$_2$CO$_2$H,
—C(O)CH(Me)CH$_2$CO$_2$Me,
—C(O)CH(Me)CH$_2$CO$_2$Et,
—C(O)CH(Me)CH$_2$CO$_2$iPr,
—C(O)CH(Me)CH$_2$CO$_2$tBu,
—C(O)CH(Me)CH(Me)CO$_2$H,
—C(O)CH(Me)CH(Me)CO$_2$Me,
—C(O)CH(Me)CH(Me)CO$_2$Et,
—C(O)CH(Me)CH(Me)CO$_2$iPr,
—C(O)CH(Me)CH(Me)CO$_2$tBu,
—C(O)CH(Me)C(Me)$_2$CO$_2$H,
—C(O)CH(Me)C(Me)$_2$CO$_2$Me,
—C(O)CH(Me)C(Me)$_2$CO$_2$Et,
—C(O)CH(Me)C(Me)$_2$CO$_2$iPr,
—C(O)CH(Me)C(Me)$_2$CO$_2$tBu,
—C(O)CH(Me)CH(Et)CO$_2$H,
—C(O)CH(Me)CH(Et)CO$_2$Me,
—C(O)CH(Me)CH(Et)CO$_2$Et,
—C(O)CH(Me)CH(Et)CO$_2$iPr,
—C(O)CH(Me)CH(Et)CO$_2$tBu,
—C(O)C(O)OH,
—C(O)C(O)NH$_2$,
—C(O)C(O)NHMe,
—C(O)C(O)NMe$_2$,
—C(O)NH$_2$,
—C(O)NMe$_2$,
—C(O)NH—CH$_2$—C(O)OH,
—C(O)NH—CH$_2$—C(O)OMe,
—C(O)NH—CH$_2$—C(O)OEt,
—C(O)NH—CH$_2$—C(O)OiPr,
—C(O)NH—CH$_2$—C(O)OtBu,
—C(O)NH—CH(Me)-C(O)OH,
—C(O)NH—CH(Me)-C(O)OMe,
—C(O)NH—CH(Me)-C(O)OEt,
—C(O)NH—CH(Me)-C(O)iPr,
—C(O)NH—CH(Me)-C(O)tBu,
—C(O)NH—CH(Et)-C(O)OH,
—C(O)NH—C(Me)$_2$-C(O)OH,
—C(O)NH—C(Me)$_2$-C(O)OMe,
—C(O)NH—C(Me)$_2$-C(O)OEt,
—C(O)NH—C(Me)$_2$-C(O)iPr,
—C(O)NH—C(Me)$_2$-C(O)tBu,
—C(O)NH—CMe(Et)-C(O)OH,
—C(O)NH—CH(F)—C(O)OH,
—C(O)NH—CH(CF$_3$)—C(O)OH,
—C(O)NH—CH(OH)—C(O)OH,
—C(O)NH—CH(cyclopropyl)-C(O)OH,
—C(O)NH—C(Me)$_2$-C(O)OH,
—C(O)NH—C(Me)$_2$-C(O)OH,
—C(O)NH—CF(Me)-C(O)OH,
—C(O)NH—C(Me)(CF$_3$)—C(O)OH,
—C(O)NH—C(Me)(OH)—C(O)OH,
—C(O)NH—C(Me)(cyclopropyl)CO$_2$H
—C(O)NMe-CH$_2$—C(O)OH,
—C(O)NMe-CH$_2$—C(O)OMe,
—C(O)NMe-CH$_2$—C(O)OEt,
—C(O)NMe-CH$_2$—C(O)OiPr,
—C(O)NMe-CH$_2$—C(O)tBu,
—C(O)NMe-CH$_2$—C(O)OH,
—C(O)NMe-CH(Me)-C(O)OH,
—C(O)NMe-CH(F)—C(O)OH,
—C(O)NMe-CH(CF$_3$)—C(O)OH,
—C(O)NMe-CH(OH)—C(O)OH,
—C(O)NMe-CH(cyclopropyl)-C(O)OH,
—C(O)NMe-C(Me)$_2$-C(O)OH,
—C(O)NMe-CF(Me)-C(O)OH,
—C(O)NMe-C(Me)(CF$_3$)—C(O)OH,
—C(O)NMe-C(Me)(OH)—C(O)OH,
—C(O)NMe-C(Me)(cyclopropyl)-C(O)OH,
—C(O)NHS(O)Me, —C(O)NHSO₂Me,
—C(O)—NH-5-tetrazolyl,
—C(O)NHS(O)Me,
—C(O)NHS(O)Et,
—C(O)NHSO₂Me,
—C(O)NHSO₂Et,
—C(O)NHS(O)iPr,
—C(O)NHSO₂iPr,
—C(O)NHS(O)tBu,
—C(O)NHSO₂tBu,
—C(O)NHCH₂S(O)Me,
—C(O)NHCH₂S(O)Et,
—C(O)NHCH₂SO₂Me,
—C(O)NHCH₂SO₂Et,
—C(O)NHCH₂CH₂S(O)Me,
—C(O)NHCH₂CH₂S(O)Et,
—C(O)NHCH₂CH₂SO₂Me,
—C(O)NHCH₂CH₂SO₂Et,
—C(O)N(Me)S(O)Me,
—C(O)N(Me)SO₂Me,
—C(O)—N(Me)-5-tetrazolyl,
—C(O)N(Me)S(O)Me,
—C(O)N(Me)S(O)Et,
—C(O)N(Me)SO₂Me,
—C(O)N(Me)SO₂Et,
—C(O)N(Me)S(O)iPr,
—C(O)N(Me))SO₂iPr,
—C(O)N(Me))S(O)tBu,
—C(O)N(Me)SO₂tBu,
—C(O)N(Me)CH₂S(O)Me,
—C(O)N(Me)CH₂S(O)Et,
—C(O)N(Me)CH₂SO₂Me,
—C(O)N(Me)CH₂SO₂Et,
—C(O)N(Me)CH₂CH₂S(O)Me,
—C(O)N(Me)CH₂CH₂S(O)Et,
—C(O)N(Me)CH₂CH₂SO₂Me,
—C(O)N(Me)CH₂CH₂SO₂Et,
—CH₂CO₂H,
—CH₂-5-tetrazolyl,
—CH₂CO₂Me,
—CH₂CO₂Et,
—CH₂NHS(O)Me,
—CH₂NHS(O)Et,
—CH₂NHSO₂Me,
—CH₂NHSO₂Et,
—CH₂NHS(O)iPr,
—CH₂NHSO₂iPr,
—CH₂NHS(O)tBu,
—CH₂NHSO₂tBu,
—CH₂NHCH₂CH₂SO₂CH₃,
—CH₂NH(CH₂CO₂H),
—CH₂N(C(O)Me)(CH₂CO₂H),
—CH₂-N-pyrrolidin-2-one,
—CH₂-(1-methylpyrrolidin-2-one-3-yl),
—CH₂S(O)Me,
—CH₂S(O)Et,
—CH₂S(O)₂Me,
—CH₂S(O)₂Et,
—CH₂S(O)iPr,
—CH₂S(O)₂iPr,
—CH₂S(O)tBu,
—CH₂S(O)₂tBu,
—CH₂CO₂H, CH₂C(O)NH₂,
—CH₂C(O)NMe₂,
—CH₂C(O)NHMe,
—CH₂C(O)—N-pyrrolidine,
—CH₂S(O)₂Me, CH₂S(O)Me,
—CH(OH)CO₂H,
—CH(OH)C(O)NH₂,
—CH(OH)C(O)NHMe,
—CH(OH)C(O)NMe₂,
—CH(OH)C(O)NEt₂,
—CH₂CH₂CO₂H,
—CH₂CH₂CO₂Me,
—CH₂CH₂CO₂Et,
—CH₂CH₂C(O)NH₂,
—CH₂CH₂C(O)NHMe,
—CH₂CH₂C(O)NMe₂,
—CH₂CH₂-5-tetrazolyl,
—CH₂CH₂S(O)₂Me,
—CH₂CH₂S(O)Me,
—CH₂CH₂S(O)₂Et,
—CH₂CH₂S(O)Et,
—CH₂CH₂S(O)iPr,
—CH₂CH₂S(O)₂iPr,
—CH₂CH₂S(O)tBu,
—CH₂CH₂S(O)₂tBu,
—CH₂CH₂S(O)NH₂,
—CH₂CH₂S(O)NHMe,
—CH₂CH₂S(O)NMe₂,
—CH₂CH₂S(O)₂NH₂,
—CH₂CH₂S(O)₂NHMe
—CH₂CH₂S(O)₂NMe₂,
—CH₂CH₂CH₂S(O)Me,
—CH₂CH₂CH₂S(O)Et,
—CH₂CH₂CH₂S(O)₂Me, or
—CH₂CH₂CH₂S(O)₂Et.

The compound of formula IC having as preferred substituents;

R and R' are independently methy or ethyl;

RP, RB, RB₄, and RT₃ are independently, hydrogen or methyl;

RP₃ and RB₇ are independently hydrogen, methyl, ethyl, —O-methyl, or cyclopropyl;

($L_{P1}$) and ($L_{BT}$) divalent linking groups are both bonds;

($L_{P2}$) is a bond, —CH₂—, —CH(OH)—, or —C(Me)OH—;

$Z_P$ is 1,1-dimethylethyl; 1-hydroxycyclopentyl, 1-hydroxycyclohexyl, 3-ethyl-3-hydroxypentyl, 3-ethyl-3-hydroxypentenyl, 3-ethyl-3-hydroxypentynyl;

$Z_{BT}$ is
—CO₂H,
—CO₂Me,
—CO₂Et,
—C(O)CH₂S(O)Me,
—C(O)CH₂S(O)Et,
—C(O)CH₂S(O)₂Me,
—C(O)CH₂S(O)₂Et,
—C(O)CH₂CH₂S(O)Me,
—C(O)CH₂CH₂S(O)Et,
—C(O)CH₂CH₂S(O)₂Me,
—C(O)CH₂CH₂S(O)₂Et,
—C(O)CH(Me)CH₂CO₂H,
—C(O)CH(Me)CH₂CO₂Me,
—C(O)CH(Me)CH₂CO₂Et,
—C(O)CH(Me)CH₂CO₂iPr,
—C(O)CH(Me)CH₂CO₂tBu,
—C(O)CH(Me)CH(Me)CO₂H,
—C(O)CH(Me)CH(Me)CO₂Me,
—C(O)CH(Me)CH(Me)CO₂Et,
—C(O)CH(Me)CH(Me)CO₂iPr,
—C(O)CH(Me)CH(Me)CO₂tBu,
—C(O)CH(Me)C(Me)₂CO₂H,
—C(O)CH(Me)C(Me)₂CO₂Me,

—C(O)CH(Me)C(Me)₂CO₂Et,
—C(O)CH(Me)C(Me)₂CO₂iPr,
—C(O)CH(Me)C(Me)₂CO₂tBu,
—C(O)CH(Me)CH(Et)CO₂H,
—C(O)CH(Me)CH(Et)CO₂Me,
—C(O)CH(Me)CH(Et)CO₂Et,
—C(O)CH(Me)CH(Et)CO₂iPr,
—C(O)CH(Me)CH(Et)CO₂tBu,
—C(O)C(O)OH,
—C(O)C(O)NH₂,
—C(O)C(O)NHMe,
—C(O)C(O)NMe₂,
—C(O)NH₂,
—C(O)NMe₂,
—C(O)NH—CH₂—C(O)OH,
—C(O)NH—CH₂—C(O)OMe,
—C(O)NH—CH₂—C(O)OEt,
—C(O)NH—CH₂—C(O)OiPr,
—C(O)NH—CH₂—C(O)OtBu,
—C(O)NH—CH(Me)-C(O)OH,
—C(O)NH—CH(Me)-C(O)OMe,
—C(O)NH—CH(Me)-C(O)OEt,
—C(O)NH—CH(Me)-C(O)iPr,
—C(O)NH—CH(Me)-C(O)tBu,
—C(O)NH—CH(Et)-C(O)OH,
—C(O)NH—C(Me)₂-C(O)OH,
—C(O)NH—C(Me)₂-C(O)OMe,
—C(O)NH—C(Me)₂-C(O)OEt,
—C(O)NH—C(Me)₂-C(O)iPr,
—C(O)NH—C(Me)₂-C(O)tBu,
—C(O)NH—CMe(Et)-C(O)OH,
—C(O)NH—CH(F)—C(O)OH,
—C(O)NH—CH(CF₃)—C(O)OH,
—C(O)NH—CH(OH)—C(O)OH,
—C(O)NH—CH(cyclopropyl)-C(O)OH,
—C(O)NH—C(Me)₂-C(O)OH,
—C(O)NH—C(Me)₂-C(O)OH,
—C(O)NH—CF(Me)-C(O)OH,
—C(O)NH—C(Me)(CF₃)—C(O)OH,
—C(O)NH—C(Me)(OH)—C(O)OH,
—C(O)NH—C(Me)(cyclopropyl)CO₂H
—C(O)NMe-CH₂—C(O)OH,
—C(O)NMe-CH₂—C(O)OMe,
—C(O)NMe-CH₂—C(O)OEt,
—C(O)NMe-CH₂—C(O)OiPr,
—C(O)NMe-CH₂—C(O)tBu,
—C(O)NMe-CH₂—C(O)OH,
—C(O)NMe-CH(Me)-C(O)OH,
—C(O)NMe-CH(F)—C(O)OH,
—C(O)NMe-CH(CF₃)—C(O)OH,
—C(O)NMe-CH(OH)—C(O)OH,
—C(O)NMe-CH(cyclopropyl)-C(O)OH,
—C(O)NMe-C(Me)₂-C(O)OH,
—C(O)NMe-CF(Me)-C(O)OH,
—C(O)NMe-C(Me)(CF₃)—C(O)OH,
—C(O)NMe-C(Me)(OH)—C(O)OH,
—C(O)NMe-C(Me)(cyclopropyl)-C(O)OH,
—C(O)NHS(O)Me,
—C(O)NHSO₂Me,
—C(O)—NH-5-tetrazolyl,
—C(O)NHS(O)Me,
—C(O)NHS(O)Et,
—C(O)NHSO₂Me,
—C(O)NHSO₂Et,
—C(O)NHS(O)iPr,
—C(O)NHSO₂iPr,
—C(O)NHS(O)tBu,
—C(O)NHSO₂tBu,
—C(O)NHCH₂S(O)Me,
—C(O)NHCH₂S(O)Et,
—C(O)NHCH₂SO₂Me,
—C(O)NHCH₂SO₂Et,
—C(O)NHCH₂CH₂S(O)Me,
—C(O)NHCH₂CH₂S(O)Et,
—C(O)NHCH₂CH₂SO₂Me,
—C(O)NHCH₂CH₂SO₂Et,
—C(O)N(Me)S(O)Me,
—C(O)N(Me)SO₂Me,
—C(O)—N(Me)-5-tetrazolyl,
—C(O)N(Me)S(O)Me,
—C(O)N(Me)S(O)Et,
—C(O)N(Me)SO₂Me,
—C(O)N(Me)SO₂Et,
—C(O)N(Me)S(O)iPr,
—C(O)N(Me))SO₂iPr,
—C(O)N(Me))S(O)tBu,
—C(O)N(Me)SO₂tBu,
—C(O)N(Me)CH₂S(O)Me,
—C(O)N(Me)CH₂S(O)Et,
—C(O)N(Me)CH₂SO₂Me,
—C(O)N(Me)CH₂SO₂Et,
—C(O)N(Me)CH₂CH₂S(O)Me,
—C(O)N(Me)CH₂CH₂S(O)Et,
—C(O)N(Me)CH₂CH₂SO₂Me,
—C(O)N(Me)CH₂CH₂SO₂Et,
—CH₂CO₂H,
—CH₂-5-tetrazolyl,
—CH₂CO₂Me,
—CH₂CO₂Et,
—CH₂NHS(O)Me,
—CH₂NHS(O)Et,
—CH₂NHSO₂Me,
—CH₂NHSO₂Et,
—CH₂NHS(O)iPr,
—CH₂NHSO₂iPr,
—CH₂NHS(O)tBu,
—CH₂NHSO₂tBu,
—CH₂NHCH₂CH₂SO₂CH₃,
—CH₂NH(CH₂CO₂H),
—CH₂N(C(O)Me)(CH₂CO₂H),
—CH₂—N-pyrrolidin-2-one,
—CH₂-(1-methylpyrrolidin-2-one-3-yl),
—CH₂S(O)Me,
—CH₂S(O)Et,
—CH₂S(O)₂Me,
—CH₂S(O)₂Et,
—CH₂S(O)iPr,
—CH₂S(O)₂iPr,
—CH₂S(O)tBu,
—CH₂S(O)₂tBu,
—CH₂CO₂H, CH₂C(O)NH₂,
—CH₂C(O)NMe₂,
—CH₂C(O)NHMe,
—CH₂C(O)—N-pyrrolidine,
—CH₂S(O)₂Me, CH₂S(O)Me,
—CH(OH) CO₂H,
—CH(OH)C(O)NH₂,
—CH(OH)C(O)NHMe,
—CH(OH)C(O)NMe₂,
—CH(OH)C(O)NEt₂,
—CH₂CH₂CO₂H,
—CH₂CH₂CO₂Me,
—CH₂CH₂CO₂Et,
—CH₂CH₂C(O)NH₂, —CH₂CH₂C(O)NHMe,
—CH₂CH₂C(O)NMe₂,
—CH₂CH₂-5-tetrazolyl,
—CH₂CH₂S(O)₂Me,
—CH₂CH₂S(O)Me,
—CH₂CH₂S(O)₂Et,
—CH₂CH₂S(O)Et,
—CH₂CH₂S(O)iPr,
—CH₂CH₂S(O)₂iPr,
—CH₂CH₂S(O)tBu,
—CH₂CH₂S(O)₂tBu,
—CH₂CH₂S(O)NH₂,
—CH₂CH₂S(O)NHMe,
—CH₂CH₂S(O)NMe₂,
—CH₂CH₂S(O)₂NH₂,
—CH₂CH₂S(O)₂NHMe
—CH₂CH₂S(O)₂NMe₂,
—CH₂CH₂CH₂S(O)Me,
—CH₂CH₂CH₂S(O)Et,
—CH₂CH₂CH₂S(O)₂Me, or
—CH₂CH₂CH₂S(O)₂Et.

Particularly preferred compounds of the invention and salts and prodrug derivatives are represented by formulae C1 to C22 as follows:

C1)
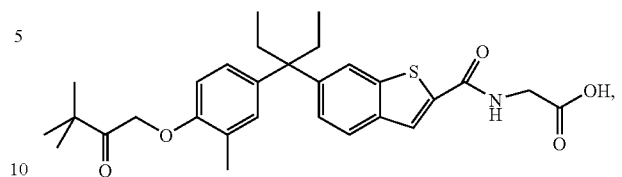

C2)
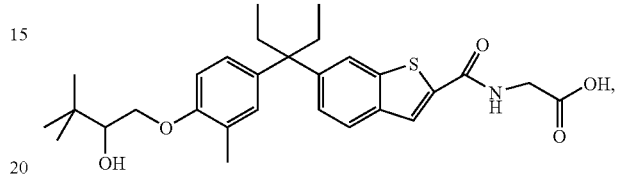

C3)
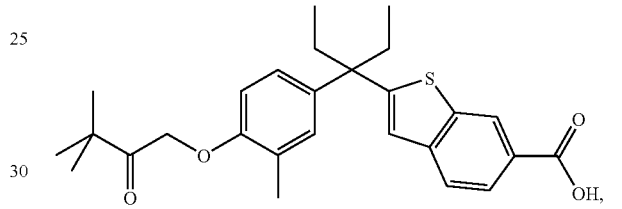

C4)
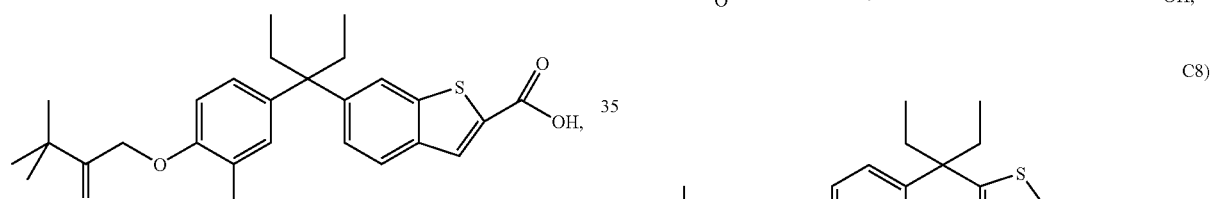

C5)
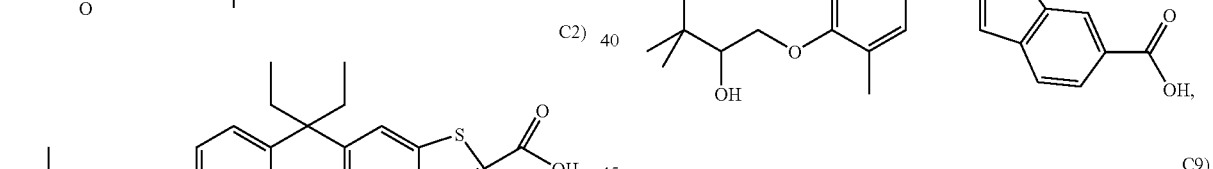

C6)
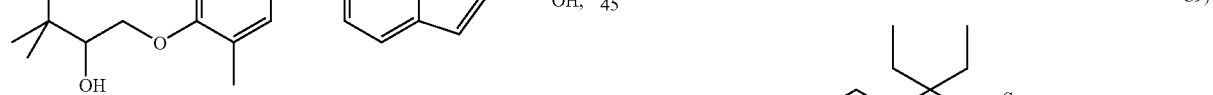

C7)

C8)
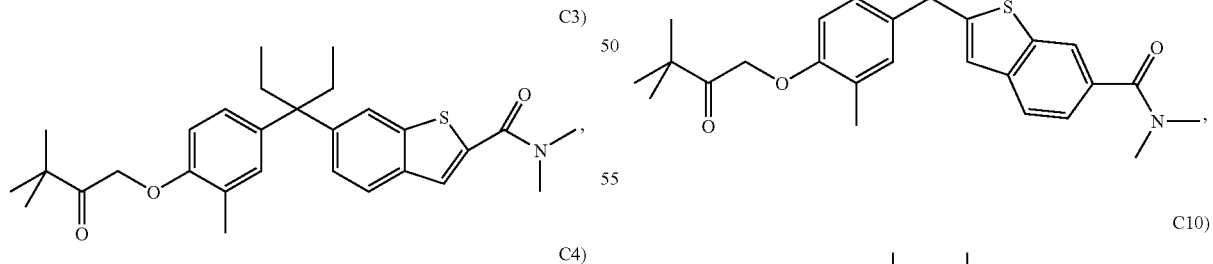

C9)

C10)
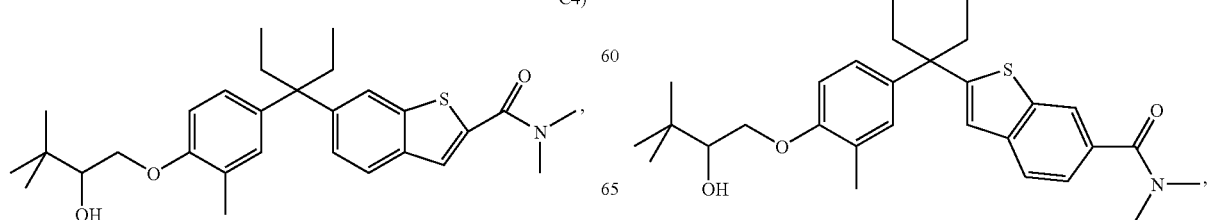

C11) 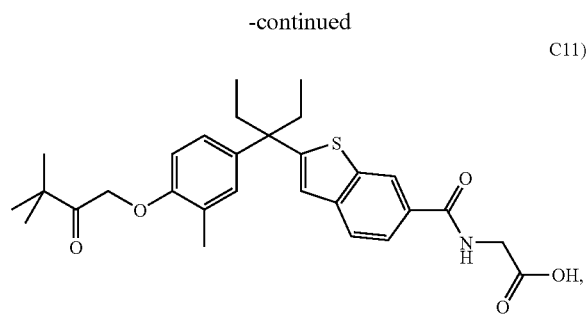
C12) 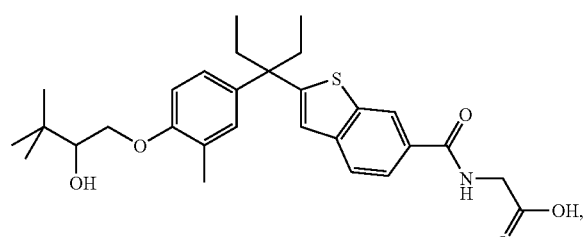
C13) 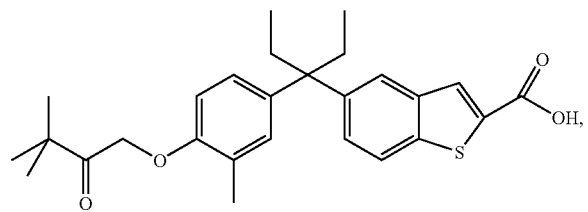
C14) 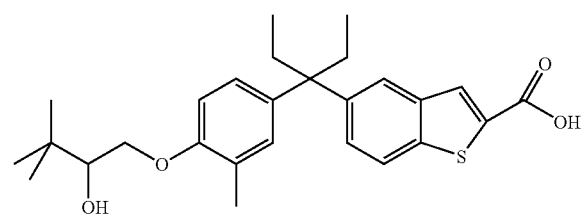
C15) 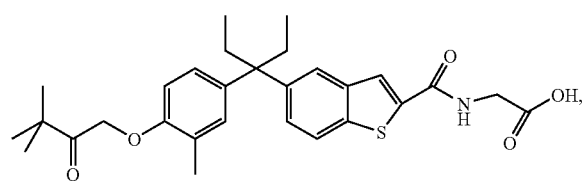
C16) 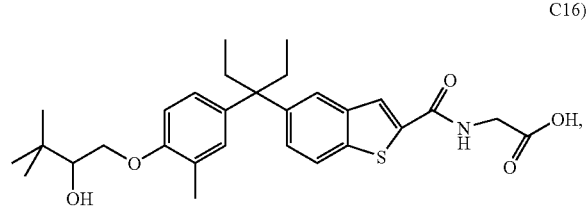
C17) 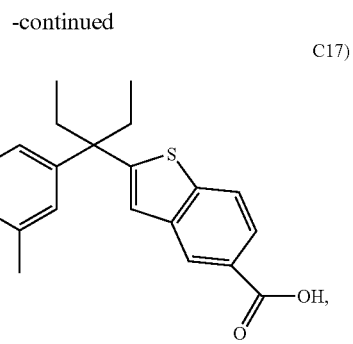
C18) 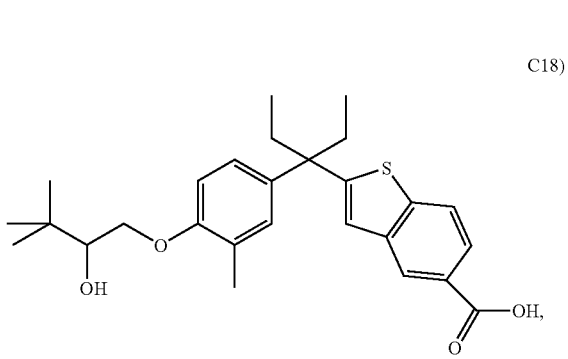
C19) 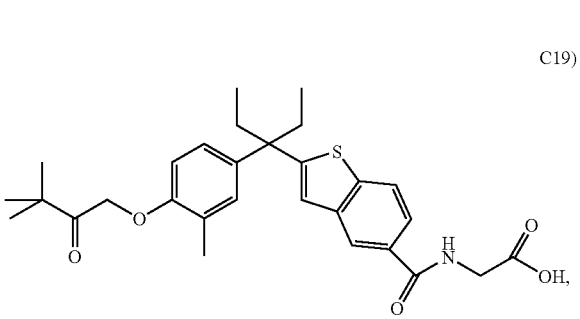
C20) 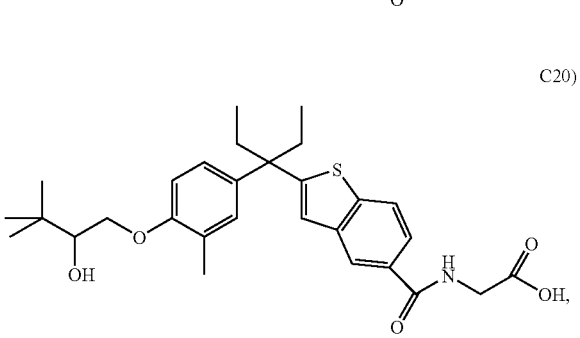
C21) 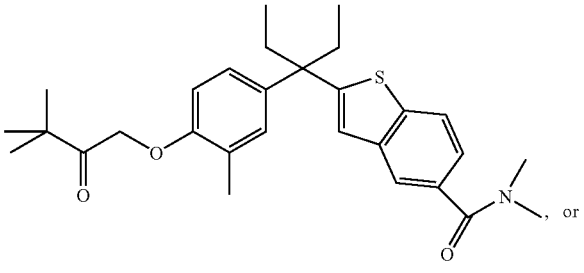

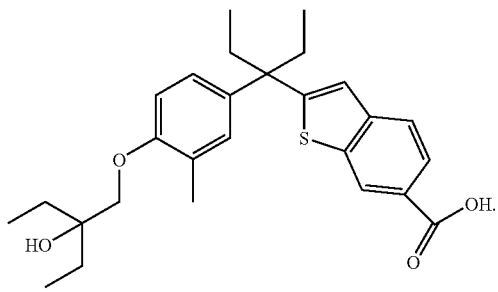

Particularly preferred is the compound represented by the structural formula AA or a pharmaceutically acceptable salt or prodrug thereof:

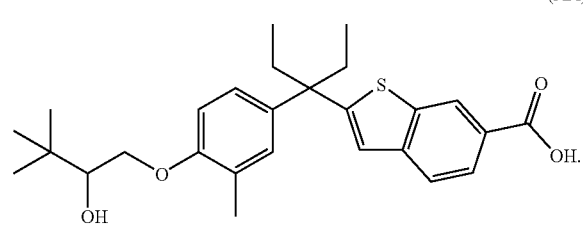

EXAMPLES

General Experimental Conditions:

The starting material/intermediate is the compound from the immediate preceding experimental unless otherwise indicated.

All reactions are performed under nitrogen/argon atmosphere, in a stirred reaction vessel, and at room temperature unless indicated otherwise.

Unless otherwise indicated, the organic layer is $MgSO_4$/$Na_2SO_4$ dried is defined as stirring the solution with a dessicant for 5-15 m and filtering off the dessicant to give an anhydrous filtrate.

For analogous multi-step reaction procedures, the yield is given either for the ultimate step or overall multi-steps as indicated.

Solutions are "concentrated" at a range of 25-75° C. with reduced pressure. in-vacuo −25-75° C.; 0.05 to 1 mm Unless otherwise indicated, "the residue is chromatographed" is defined as silica gel chromatography of residue with moderate nitrogen pressure (flash chromatography) or a medium pressure chromatography systems using a silica gel to crude product ratio of ~10-100.

For HPLC, the conditions listed are for the analytical trace only. For Preparative HPLC, the eluent is similar to analytical HPLC eluent.

Thin layer chromatography is performed with silica gel plates with UV and/or appropriate staining solution.

NMR spectra are obtained with either 300 or 400 mHz spectrometer.

NMR data is listed to denote spectrum is consistent with assigned structure.

"NMR" notation without data denotes spectrum is consistent with assigned structure.

HRMS—high resolution mass spectrum
ES-MS—electrospray mass spectrum
Abbreviations:
Aq—aqueous
d—day
eq—equivalent
h—hour
m—minute
satd—saturated
disp—dispersion
quant—quantitative
rt for retention time (both small caps to minimize confusion with RT)
RT—room temperature
Chemical Definitions:
BF3-OEt2—boron trifluoride etherate
BnBr—benzyl bromide
CH2Cl2—dichloromethane
CH3CN—acetonitrile
CO—carbon monoxide
CsF—cesium fluoride
DMAP—4-(dimethylamino)pyridine
DMF—N,N-dimethylformamide
DMSO—dimethylsulfoxide
DPPB—1,4-bis(diphenylphosphino)butane
DPPF—dichloro[-1,1'-bis(dipeylphosphino)ferrocene
EDCI—3-Ethyl-1-[3-(dimethylamino)propyl]carbodiimide hydrochloride
Et3N—triethylamine
EtMgBr—ethyl magnesium bromide
EtOAc—ethyl acetate
EtOH—ethanol
H2—hydrogen pressure
H2NCH2CO2Me—methyl glycinate
Hept—heptane
Hex—hexanes
HN(OMe)Me—N-methyl-O-methyl hydroxylamine
HNMe2—dimethyl amine
HATU—O-(7-azabenzotriazol-1-yl)-N,N,N',N'-tetramethyluronium hexafluorophosphate
HOAT—7-aza-1-hydroxybenzotriazole
HOBT—1-hydroxybenzotriazole
K2CO3—potassium carbonate
KI—potassium iodine
KOH—potassium hydroxide
LAH—lithium aluminum hydride
LiHMDS—lithium hexamethyldisilazide
Lindlar catalyst—Pd—$CaCO_3$—PbO
LiOH—lithium hydroxide
mCPBA—meta-chloroperbenzoic acid
MeI—methyl iodide
MeOH—methanol
NaBH4—sodium borohydride
MgSO4—magnesium sulfate
NaH—sodium hydride
NaHCO3—sodium bicarbonate
NaI—sodium iodide Na2SO4—sodium sulfate
NH4Cl—ammonium chloride
NMO—4-methylmorpholine N-oxide
NMP—N-methylpyrrolidin-2-one
Na—S—R3—sodium alkylmercaptide
PBr3—phosphorus tribromide
Pd(DPPF)—palladium dichloro[1,1'-bis(diphenylphosphino)ferrocene
Pd(OAc)2—palladium (II) acetate
Pd(TPP)4—palladium tetrakistriphenylphosphine
Pd—C—palladium on carbon
Pd—C/H2—palladium on carbon with hydrogen pressure
pTSA—para-toluenesulfonic acid
Pyr—pyridine
Red-Al—sodium bis(2-methoxyethoxy)aluminum hydride
R2MgBr—alkyl magnesium bromide
R3MgBr—alkyl magnesium bromide
R5MgBr—alkyl magnesium bromide
R3S(O)2Cl—alkylsulfonyl chloride
R2S(O)2NH2—alkylsulfonamide
TBSCl—tert-butyldimethylsilyl chloride
tBuC(O)CH$_2$Br—1-bromopinacolone
Tf2O—triflic anhydride
TFA—trifluoroacetic acid
THF—tetrahydrofuran
Ti(OiPr)4—titanium tetraisopropoxide
TMS-acetylene—trimethylsilyl acetylene
TPAP—tetrapropylammonium perruthenate
Zn(OTf)2—zinc trifluoromethane sulfonate General Procedures

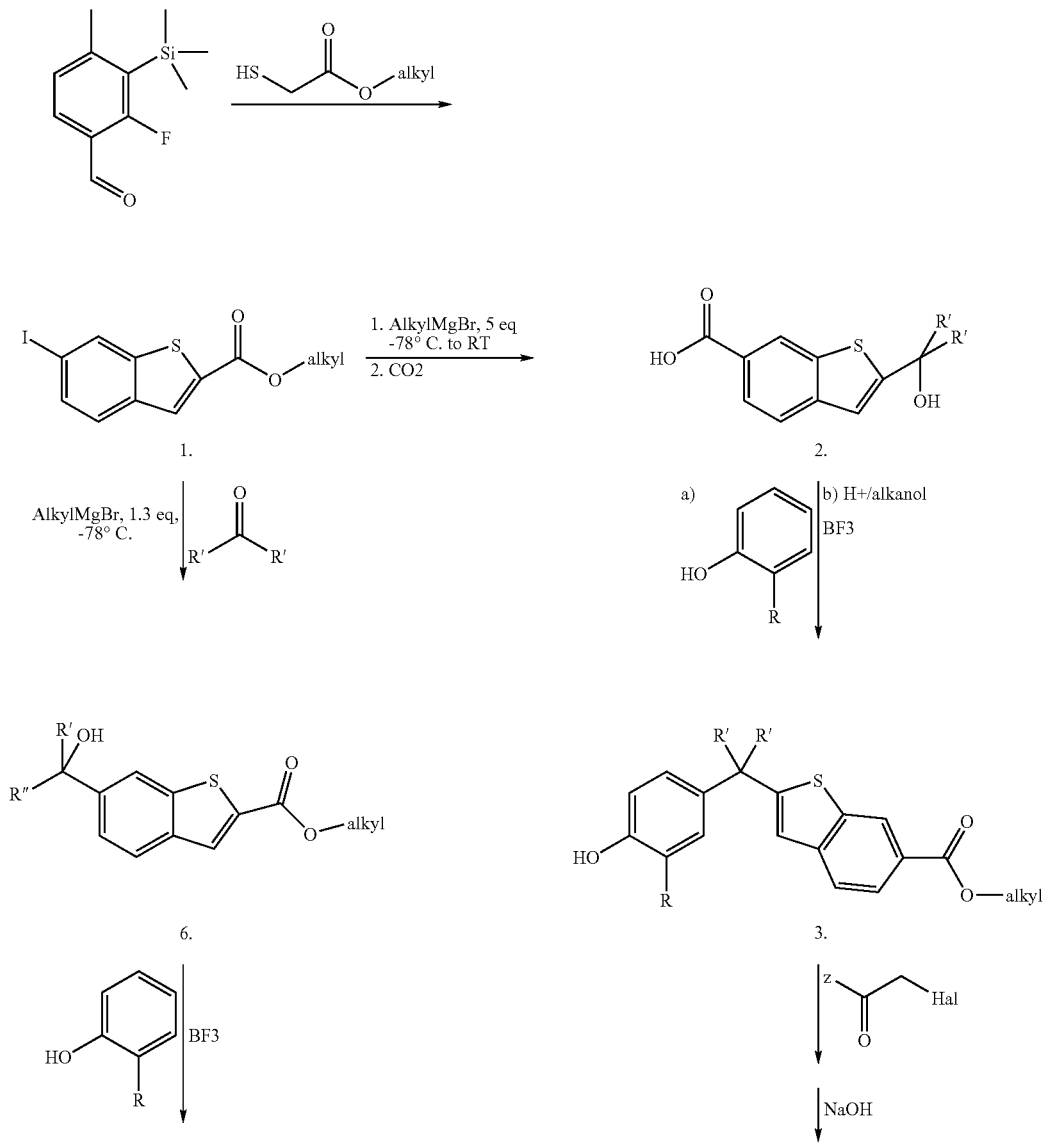

-continued
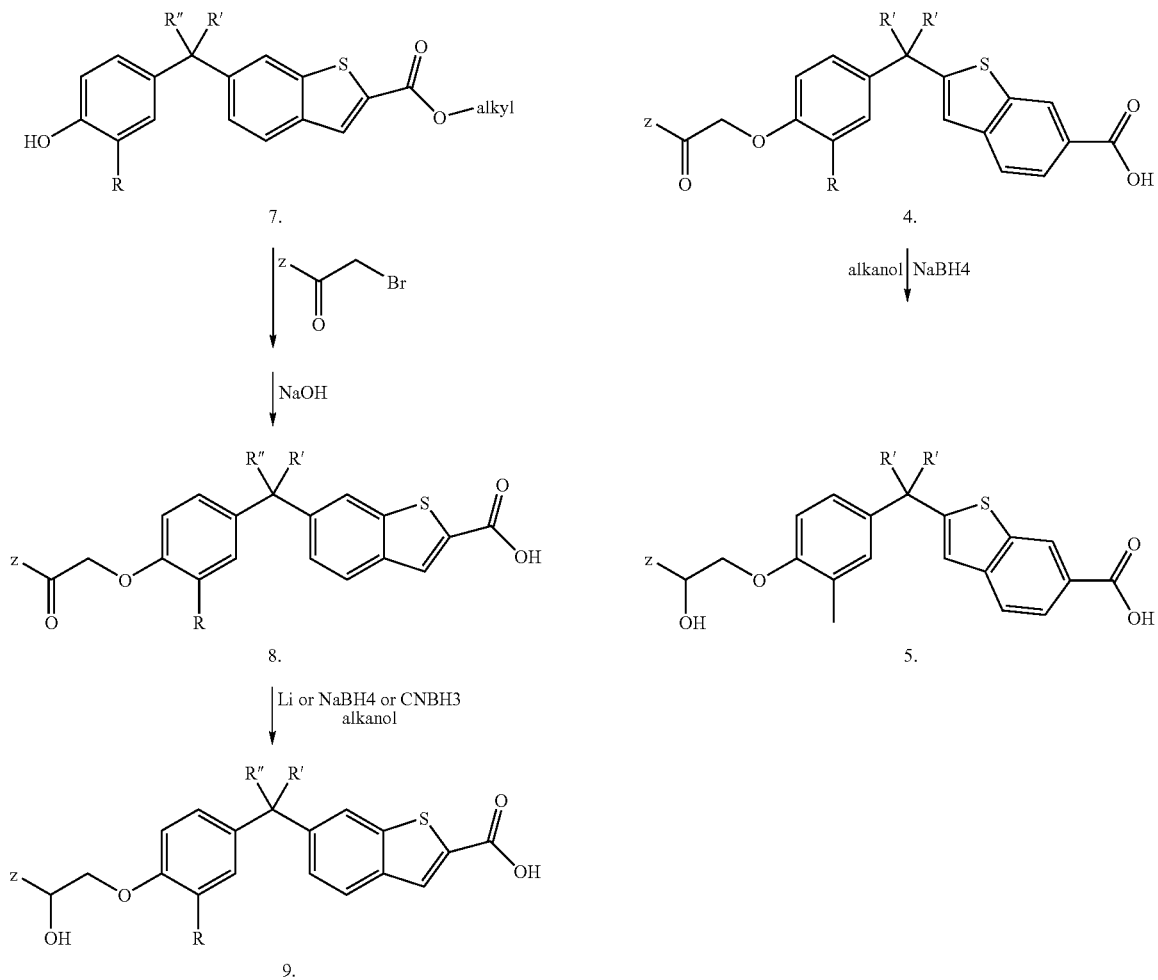
Scheme II.
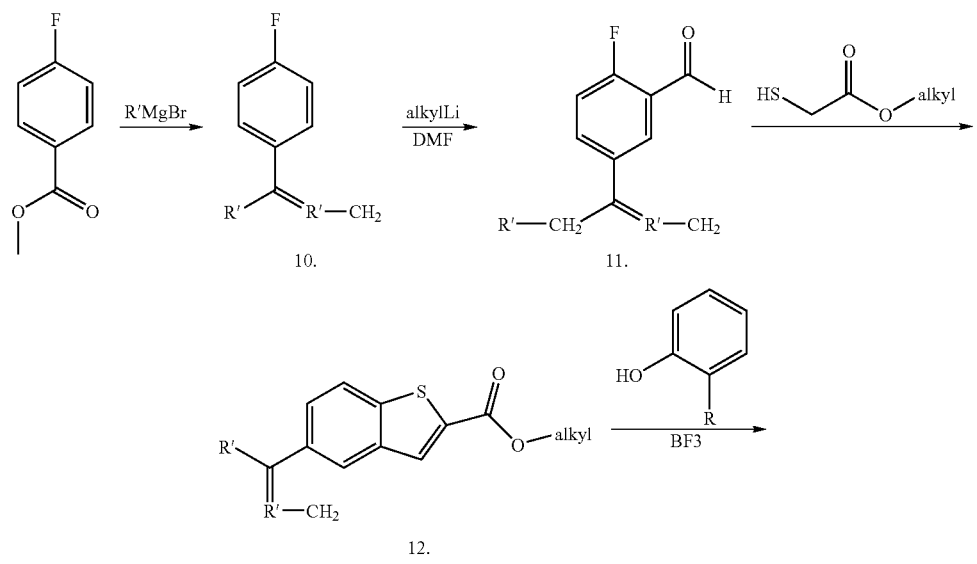

-continued
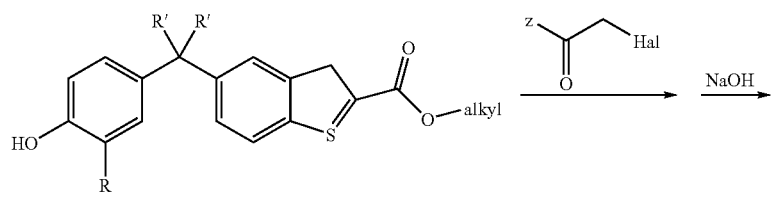
13.
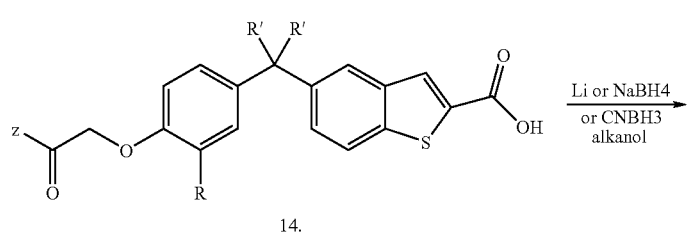
14.
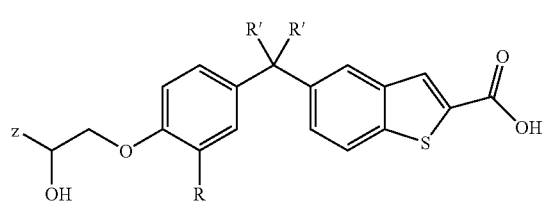
15.
Here, R'——CH₂ means R' minus a methylene group
Scheme III.
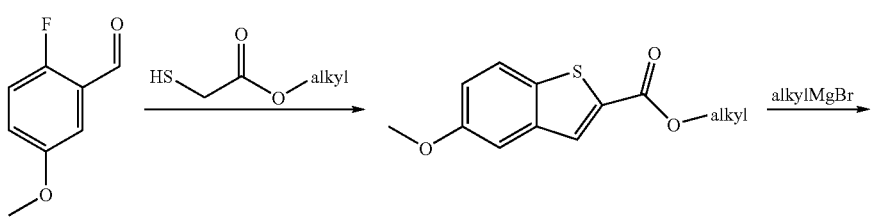
16.
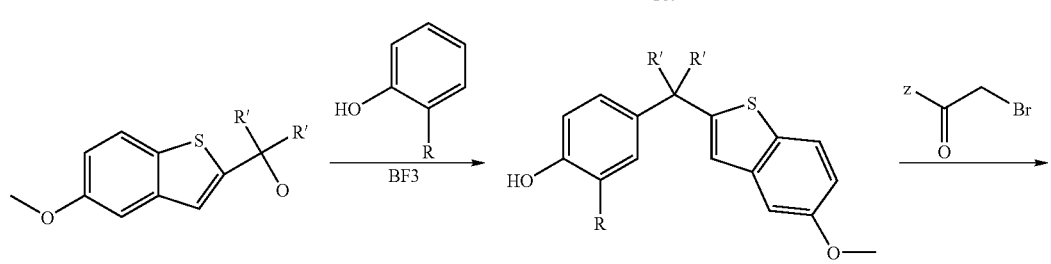
17.    18.
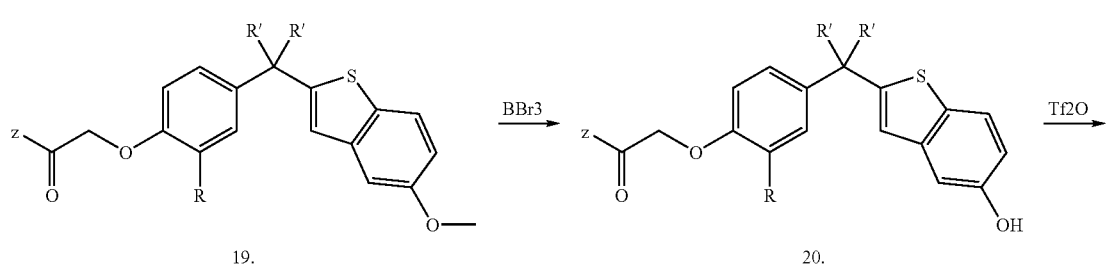
19.    20.

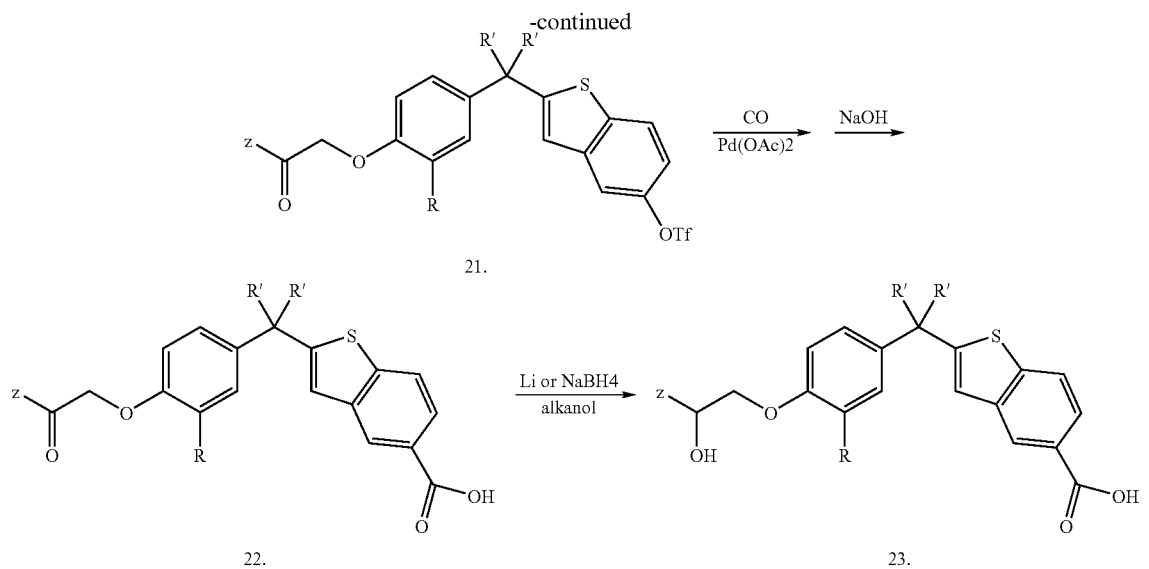
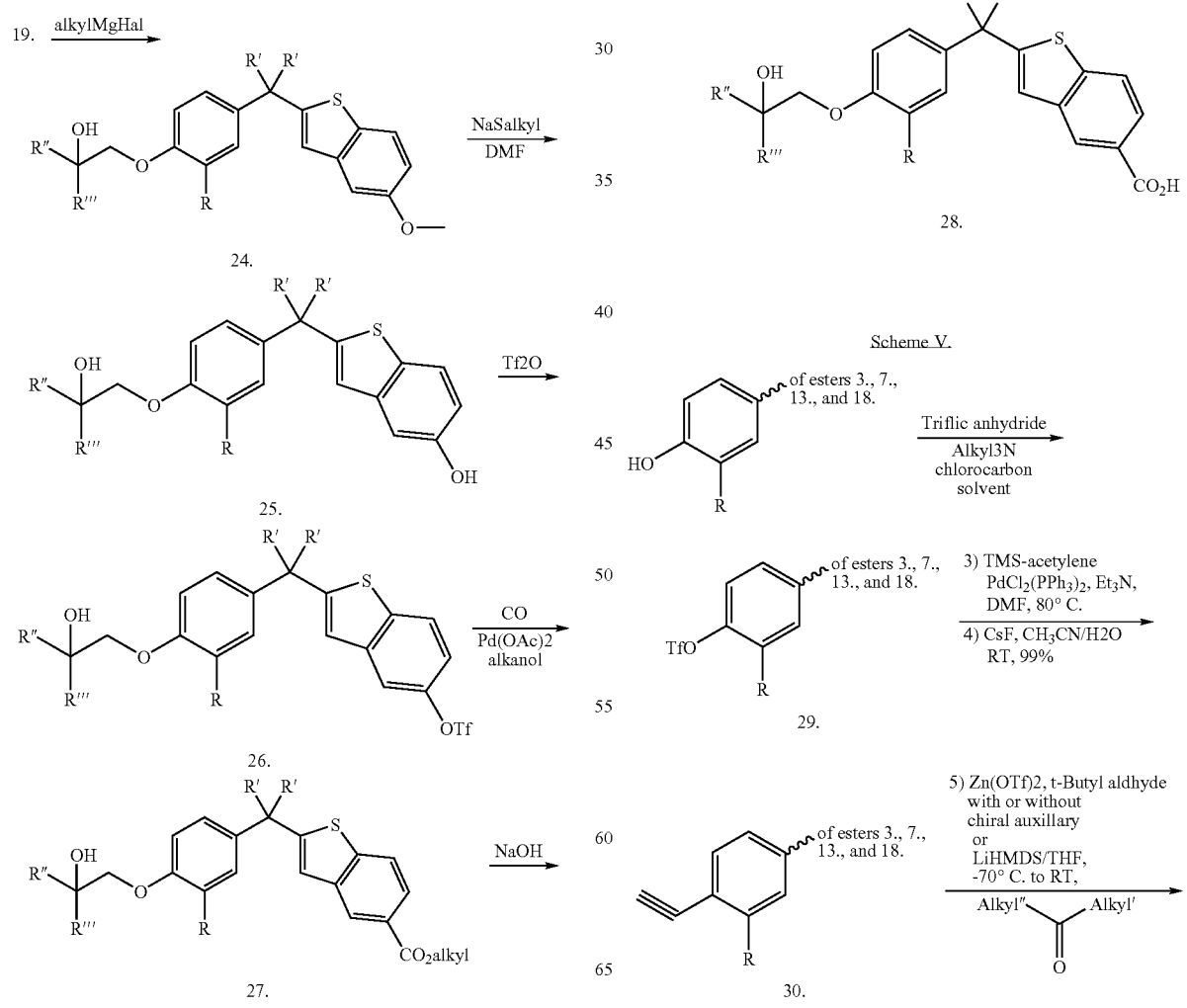

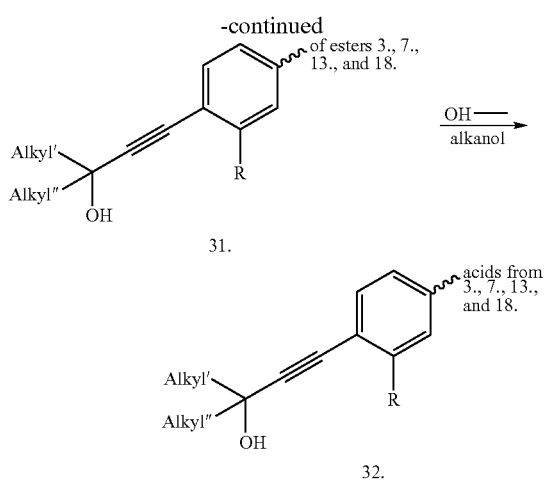

Scheme I. The known 2-fluoro-4-iodo-3-trimethylsilanyl-benzaldehyde is reacted with a mercaptoacetic acid ester to form benzo[b]thiophene ester 1. Benzo[b]thiophene 1. is reacted with an alkyl Grignard reagent (0.9 to 1.3 equivalents) at low temperature in diethylether or THF to undergo magnesium exchange with the iodine of 1. that is subsequently treated with a disubstituted ketone to produce the tert-carbinol 6. tert-Carbinol 6. is reacted with an ortho-substituted phenol in the presence of a Lewis acid, e.g., borontrifluoride etherate from 0° C. to room temperature to give the diarylmethane 7. The free hydroxyl of diarlymethane 7. is alkylated with an alpha-halo ketone in a polar aprotic solvent such as acetone or acetonitrile, with or without catalytic potassium iodide from room temperature to the reflux temperature of the mixture. The alkylated intermediate preceeding is saponified with lithium, potassium, or sodium hydroxide and alkanol from room temperature to the reflux temperature of the mixture to produce the acid 8. The ketone fragment of acid 8. is reduced with lithium, potassium, or sodium borohydride or cyanoborohydride (1 to 4 equivalents) in alkanol to the carbinol 9.

Alternately, benzo[b]thiophene 1. can be used as follows: 1. is reacted with an excess of alkyl Grignard reagent (3-6 equivalents) in THF or ether at higher temperature, e.g., room temperature to not only undergo magnesium exchange with the iodine of 1. but also to produce the tert-carbinol fragment of 2. The mixture is subsequently treated with excess carbon dioxide to produce the acid 2. Reaction of acid 2. with an ortho-substituted phenol in the presence of a Lewis acid (0.01 to 5 equivalents), e.g., boron trifluruoride etherate from 0° C. to room temperature gives a diarylmethane acid 3 that is esterified with acid and alkanol to the ester 3. The free hydroxyl of ester 3. is alkylated with an alpha-halo ketone in polar aprotic solvent to give an intermediate which is subsequently saponified with lithium, potassium, or sodium hydroxide in an alkanol (room temperature to relfux temperature) to give the acid 4. Acid 4. is reduced to the carbinol 5. with lithium, potassium, or sodium borohydride or cyanoborohydride (1 to 4 equivalents) in alkanol (0° C. to room temperature).

Scheme. II. Methyl, p-fluorobenzoate is reacted with excess alkyl Grignard reagent (2 to 5 equivalents) to produce the tert-carinol intermediate, which eliminates water upon workup to give the olefin 10. Ortho metallation with an alkyllithium reagent of olefin 10. in diethylether or THF from 0° C. to room temperature followed by treatment with DMF produces the aldehyde 11. Aldehyde 11. is reacted with a mercaptoacetic acid ester to give the benzo[b]thiophene 12. The benzo[b]thiophene 12. will alkylate an ortho-substituted phenol in the presence of a Lewis acid, e.g., boron trifluoride etherate (0.01 to 5 equivalents) to give the diarylmethane 13. The free hydroxyl of diarylmethane 13. is alkylated with an alpha-halo ketone in a polar aprotic solvent, e.g., acetone or acetonitrile from room temperature to the reflux temperature of the mixture, and the alkylated intermediate is subsequently saponified with lithium, potassium, or sodium hydroxide in an alkanol (room temperature to the reflux temperature of the mixture) to give the acid 14. The acid 14. is reduced to the carbinol 15. with lithium, potassium, or sodium borohydride or cyanoborohydride (1-4 equivalents) in alkanol from 0° C. to room temperature.

Scheme III. Benzo[b]thiophene 16. is prepared by the reaction of a mercaptoacetic acid ester and 2-fluoro-5-methoxy-benzaldehyde in DMF. The benzo[b]thiophene 16. is reacted with excess alkyl Grignard reagent (2 to 5 equivalents) in diethylether or THF (0° C. to room temperature) to give the tert-carbinol 17. The tert-carbinol 17. alkylates an ortho-substituted phenol in the presence of a Lewis acid, e.g., boron trifluoride etherate (0.01 to 5 equivalents) to give the diarylmethane 18. The free hydroxyl of diarylmethane 18. is alkylated with an alpha-halo ketone or ester in a polar aprotic solvent, e.g., acetone or acetonitrile from room temperature to the reflux temperature of the mixture to give the methoxy intermediate 19. The intermediate 19. is demethylated with boron tribromide in halocarbon solvent from 0° to room temperature to give the free hydroxyl intermediate 20. The intermediate 20. is converted to the triflate 21. with triflic anhydride and base, and the triflate 21. is reacted with carbon monoxide (1-100 psi) in the presence of palladium catalysis (0.01 to 0.10 equivalents), e.g., palladium acetate and DPPB, and base to give the ester intermediate which is subsequently saponified with lithium, potassium, or sodium hydroxide in alkanol to give the keto acid 22. The keto acid 22. is reduced to the carbinol 23. with lithium, potassium, or sodium borohydride or cyanoborohydride (1-4 equivalents) in alkanol from 0° C. to room temperature.

Scheme IV. Intermediate 19 is reacted with an alkyl Grignard reagent (1-5 equivalents) in ether or THF to give the methoxy carbinol 24. Methoxy carbinol 24. is demethylated with sodium mercaptoethylate in a polar aprotic solvent, e.g., DMF from room temperature to 150° C. to give the hydroxy carbinol 25. The hydroxy carbinol 25. is converted to the triflate 26. with triflic anhydride and base, and the triflate 26. is reacted with carbon monoxide (1-100 psi) in the presence of palladium catalysis (0.01 to 0.10 equivalents), e.g., palladium acetate and DPPB, and base to give the ester 27. The ester 27. is saponified with lithium, potassium, or sodium hydroxide in alkanol to give the acid 28.

Scheme V. The free hydroxyls of esters 3., 7., 13., and 18., from Schemes I. II. And III. above are converted to the triflates 29. with triflic anhydride and base. Each of these triflates 29. is couple to TMS-acetylene in the presence of a palladium catalyst, e.g., PdCl2(PPh3)2 (0.01 to 10%) in a polar aprotic solvent, e.g., acetonitriel from room temperature to 150 C. to give the TMS protected acetylenes as intermediates, that are deprotected with fluoride ion in THF to give acetylenes 30. Each of the acetylenes 30. are deprotonated with, e.g., LiHMDS and treated with a ketone to produce the carbinols 31. Each of the carbinols 31. are saponified with lithium, potassium, or sodium hydroxide in alkanol to give the acids 32.

Each of the free acids produced in each of the above schemes (3., 4., 5., 8., 9., 14., 15., 22., 23., and 28.) are converted to lower alkanol esters and lower alkyl secondary or tertiary carboxamides using reactions well known to those skilled in the art.

Example 1

Preparation of 6-{1-[4-(3,3-dimethyl-2-oxo-butoxy)-3-methyl-phenyl]-1-ethyl-propyl}-benzo[b]thiophene-2-carboxylic acid

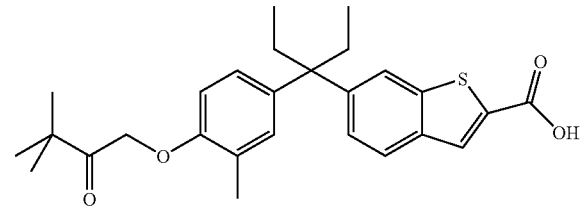

A. 6-Iodo-benzo[b]thiophene-2-carboxylic acid ethyl ester

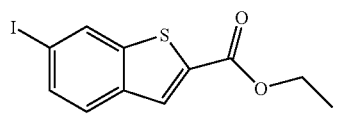

A solution of 2-fluoro-4-iodo-3-trimethylsilanyl-benzaldehyde (14.2 g, 44.1 mmol) (*Tetrahedron Letters* 1992, p7499-7502) in DMF (50 mL) is treated with mercapto-acetic acid ethyl ester (5.80 mL, 52.9 mmol) and $K_2CO_3$ (12.2 g, 88.2 mmol). The resulting suspension is stirred at 75° C. for 60 min and quenched with water (300 mL). The mixture is extracted with EtOAc (3×50 mL,) and the organic layer is dried over $Na_2SO_4$, concentrated, and purified by silica gel column chromatography (5-20% EtOAc/Hex), to give the title compound as an oil (9.40 g, 64%).

H-NMR (ppm, $CDCl_3$), δ: 8.21 (1 H, d, J=1.8 Hz), 7.98 (1 H, s), 7.67 (1 H, dd, J=1.8, 8.8 Hz), 7.58 (1 H, d, J=8.4 Hz), 4.40 (2 H, q, J=7.0 Hz), 1.42 (3 H, t, J=7.0 Hz).

B. 6-(1-Ethyl-1-hydroxy-propyl)-benzo[b]thiophene-2-carboxylic acid ethyl ester

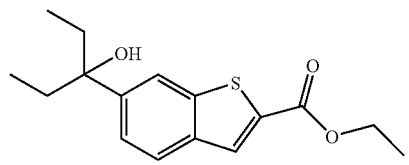

To a stirred solution of 6-iodo-benzo[b]thiophene-2-carboxylic acid ethyl ester (2.95 g, 8.88 mmol) in THF (60 mL) at −78° C. is added ethylmagnesium bromide (4.45 mL, 3.0 M). The reaction mixture is stirred for 15 min, and 3-pentanone (3.0 mL) is added. The mixture is allowed to warm to RT and stirred for 30 min. The reaction is quenched with HCl (15 mL, 1.0 M) and extracted with EtOAc (2×50 mL). The organic layer is dried over $Na_2SO_4$, concentrated, and purified by silica gel column chromatography to give the title compound (0.65 g, 25%).

H-NMR (ppm, $CDCl_3$), d: 8.02 (1 H, s), 7.95 (1 H, s), 7.80 (1 H, d, J=8.8 Hz), 7.35 (1 H, dd, J=1.3, 8.4 Hz), 4.40 (2 H, q, J=7.0 Hz), 1.88 (4 H, q, J=7.5 Hz), 1.42 (3 H, t, J=7.0 Hz), 0.78 (6 H, q, J=7.5 Hz).

C. 6-[1-Ethyl-1-(4-hydroxy-3-methyl-phenyl)-propyl]-benzo[b]thiophene-2-carboxylic acid ethyl ester

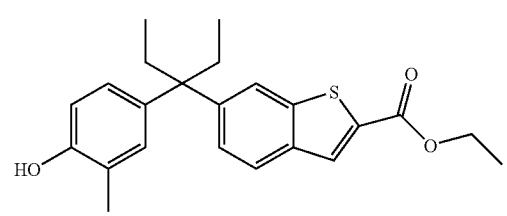

To a mixture of 6-(1-ethyl-1-hydroxy-propyl)-benzo[b]thiophene-2-carboxylic acid ethyl ester (0.650 g, 2.23 mmol and o-cresol (0.480 g, 4.45 mmol) in $CH_2Cl_2$ (20 mL) at −78° C. is added $BF_3$-$Et_2O$ (0.316 g, 2.23 mol). After stirring for 10 min, the reaction mixture is allowed to warm to 0° C. over 30 min. The reaction is quenched with water (15 mL) and extracted with EtOAc (2×50 mL). The organic layer is dried over $Na_2SO_4$, concentrated, and purified by silica gel column chromatography to give the title compound (0.780 g, 92%).

MS (ES) m/e 383.1 (M+1), 381.1 (M−1).

D. 6-{1-[4-(3,3-Dimethyl-2-oxo-butoxy)-3-methyl-phenyl]-1-ethyl-propyl}-benzo[b]thiophene-2-carboxylic acid ethyl ester

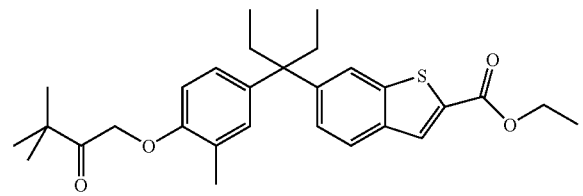

A solution of 6-[1-ethyl-1-(4-hydroxy-3-methyl-phenyl)-propyl]-benzo[b]thiophene-2-carboxylic acid ethyl ester (0.780 g, 2.04 mmol) and 1-bromopinacolone (0.731 g, 4.08 mmol) in acetone (30 mL) is treated with $K_2CO_3$ (0.563 g, 4.08 mmol) and stirred at RT for 4 h. The mixture is filtered, and the filtrate is concentrated. The residue is purified using silica gel column chromatography (10-15% EtOAc/Hex) to provide the title compound (0.89 g, 91%).

MS (ES) m/e 498.2 (M+18).

E. 6-{1-[4-(3,3-Dimethyl-2-oxo-butoxy)-3-methyl-phenyl]-1-ethyl-propyl}-benzo[b]thiophene-2-carboxylic acid A solution of 6-{1-[4-(3,3-dimethyl-2-oxo-butoxy)-3-methyl-phenyl]-1-ethyl-propyl}-benzo[b]thiophene-2-carboxylic acid ethyl ester (0.89 g, 1.86 mmol) in MeOH (5.0 mL) and THF (5.0 mL) and is treated with NaOH (2.0 M, 10.0 mL). The resulting mixture is stirred at RT for 2 h. The mixture is concentrated, acidified with HCl (1 N) until pH~3, and extracted with EtOAc (2×50 mL). The organic layer is dried over Na$_2$SO$_4$, concentrated, and purified using silica gel column chromatography (50% EtOAc/Hex) to afford the title compound (840 mg, 99%).

MS (ES) m/e 451.1(M−1), 470.2 (M+18).

Example 2

Preparation of 6-{1-ethyl-1-[4-(2-hydroxy-3,3-dimethyl-butoxy)-3-methyl-phenyl]-propyl}-benzo[b]thiophene-2-carboxylic acid

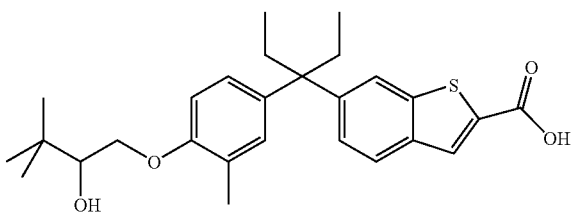

A solution of 6-{1-[4-(3,3-dimethyl-2-oxo-butoxy)-3-methyl-phenyl]-1-ethyl-propyl}-benzo[b]thiophene-2-carboxylic acid (102 mg, 0.226 mmol) in THF (5.0 mL) at RT is treated with NaBH$_4$ (17 mg, 0.451 mmol). The resulting mixture is stirred for 4 h. The reaction is quenched with HCl (1.0 N, 1.0 mL) and extracted with EtOAc (2×20 mL). The organic layer is dried over Na$_2$SO$_4$ and concentrated to afford the title compound (90 mg, 88%).

MS (ES) m/e 453.1 (M−1), 472.2 (M+18).

Example 3

Preparation of 6-{1-[4-(3,3-Dimethyl-2-oxo-butoxy)-3-methyl-phenyl]-1-ethyl-propyl}-benzo[b]thiophene-2-carboxylic acid dimethylamide

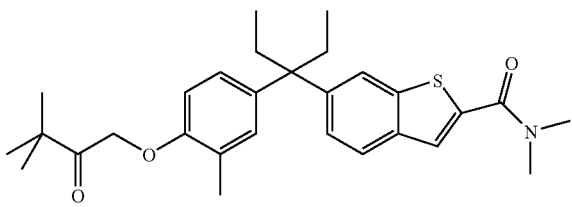

6-{1-[4-(3,3-Dimethyl-2-oxo-butoxy)-3-methyl-phenyl]-1-ethyl-propyl}-benzo[b]thiophene-2-carboxylic acid (290 mg, 0.642 mmol) in CH$_2$Cl$_2$ (5.0 mL) is treated with DMAP (235 mg, 1.93 mmol) and EDC (184 mg, 0.962 mmol). The mixture is stirred for 15 min at RT, and dimethylamine hydrochloride (78 mg, 0.962 mmol) is added. The reaction is stirred for 18 h and quenched with aqueous NH$_4$Cl (5.0 mL). The organic layer is loaded onto a silica gel column and purified with 50% EtOAc/Hex to afford the title compound (280 mg, 91%).

MS (ES) m/e 480.2 (M+1).

Example 4

Preparation of 6-{1-ethyl-1-[4-(2-hydroxy-3,3-dimethyl-butoxy)-3-methyl-phenyl]-propyl}-benzo[b]thiophene-2-carboxylic acid dimethylamide

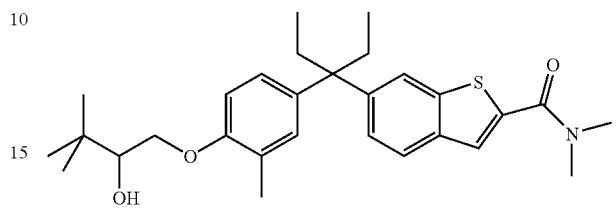

6-{1-[4-(3,3-Dimethyl-2-oxo-butoxy)-3-methyl-phenyl]-1-ethyl-propyl}-benzo[b]thiophene-2-carboxylic acid dimethylamide (235 mg, 0.490 mmol) is reduced by NaBH$_4$ (37 mg, 0.980 mmol) as in Step F11 to afford the title compound (230 mg, 100%).

MS (ES) m/e 482.2 (M+1).

Example 5

Preparation of [(6-{1-[4-(3,3-dimethyl-2-oxo-butoxy)-3-methyl-phenyl]-1-ethyl-propyl}-benzo[b]thiophene-2-carbonyl)-amino]-acetic acid

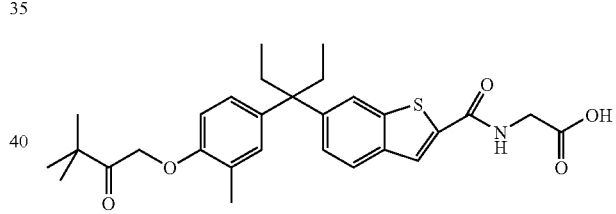

6-{1-[4-(3,3-Dimethyl-2-oxo-butoxy)-3-methyl-phenyl]-1-ethyl-propyl}-benzo[b]thiophene-2-carboxylic acid (270 mg, 0.596 mmol) in CH$_2$Cl$_2$ (5.0 mL) is treated with DMAP (218 mg, 1.79 mmol) and EDC (172 mg, 0.895 mmol). The mixture is stirred for 15 min at RT, and methyl ester hydrochloride (112 mg, 0.895 mmol) is added. The reaction is stirred for 18 h and quenched with NH$_4$Cl (5.0 mL). The organic layer is loaded onto a silica gel column and purified with 20-50% EtOAc/Hex to afford the intermediate amide ester.

The intermediate is dissolved in methanol (3.0 mL) and THF (2.0 mL) and treated with NaOH (2.0 M, 5.0 mL). The resulting mixture is stirred at RT for 3 h. The mixture is concentrated, acidified with HCl (1 N) to pH~3, and extracted with EtOAc (2×20 mL). The organic layer is dried over Na$_2$SO$_4$ and concentrated to afford the title compound (285 mg, 94%).

MS (ES) m/e 510.1 (M+1), 508.1 (M−1).

Example 6

Preparation of [(6-{1-ethyl-1-[4-(2-hydroxy-3,3-dimethyl-butoxy)-3-methyl-phenyl]-propyl}-benzo[b]thiophene-2-carbonyl)-amino]-acetic acid

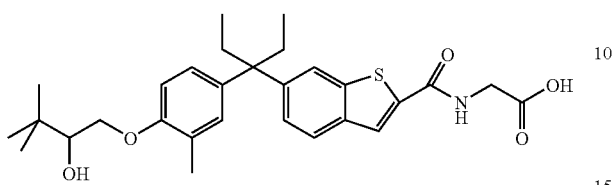

[(6-{1-[4-(3,3-Dimethyl-2-oxo-butoxy)-3-methyl-phenyl]-1-ethyl-propyl}-benzo[b]thiophene-2-carbonyl)-amino]-acetic acid (220 mg, 0.432 mmol) is reduced by NaBH₄ (33 mg, 0.863 mmol) as in Step F11 to afford the title compound (175 mg, 79%).

MS (ES) m/e 512.1 (M+1), 510.1 (M−1).

Example 7

Preparation of 2-{1-[4-(3,3-dimethyl-2-oxo-butoxy)-3-methyl-phenyl]-1-ethyl-propyl}-benzo[b]thiophene-6-carboxylic acid

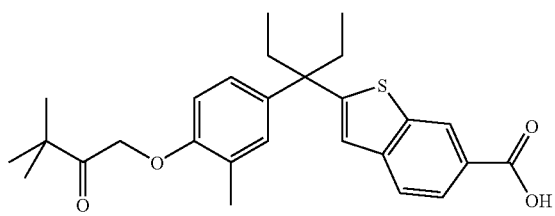

A. 2-(1-Ethyl-1-hydroxy-propyl)-benzo[b]thiophene-6-carboxylic acid

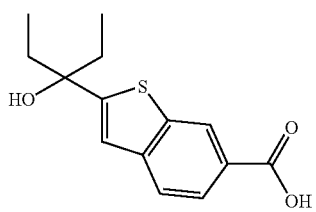

A solution of 6-iodo-benzo[b]thiophene-2-carboxylic acid ethyl ester (5.05 g, 15.2 mmol) in THF (200 mL) at −78° C. is de-oxygenated (vacuum/N2 purge 3×). Ethylmagnesium bromide (25.3 mL, 3.0 M) is added, and the reaction mixture is allowed to warm to RT over 30 min. The mixture is stirred for 10 min at RT, cooled to −78° C., and treated with clean dry ice (100 g). The mixture is allowed to warm to RT over 60 min and is quenched with HCl (50 mL, 1.0 M). THF is removed under vacuum, and the residue is extracted with EtOAc (3×100 mL). The organic layer is dried over Na₂SO₄ and concentrated to give the product (3.80 g, 94%).

MS (ES) m/e 263.0 (M−1).

B. 2-[1-Ethyl-1-(4-hydroxy-3-methyl-phenyl)-propyl]-benzo[b]thiophene-6-carboxylic acid

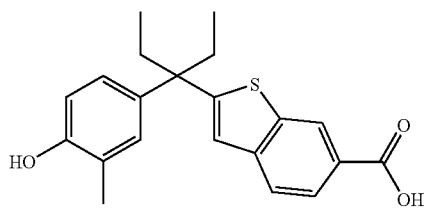

A solution of 2-(1-ethyl-1-hydroxy-propyl)-benzo[b]thiophene-6-carboxylic acid (3.80 g, 14.4 mmol) and o-cresol (1.94 g, 18.0 mmol) in CH₂Cl₂ (100 mL) at −40° C. is added BF₃-Et₂O (1.02 g, 7.20 mol). After stirring for 10 min, the reaction mixture is allowed to warm up to 0° C. over 30 min. The reaction is quenched with water (15 mL) and the aqueous layer is extracted with EtOAc (50 mL). The organic layer is dried over Na₂SO₄, concentrated, and purified by silica gel column chromatography (2% HOAc in 50% EtOAc/Hex) to give the product (3.98 g, 78%).

MS (ES) m/e 353.0 (M−1).

C. 2-[1-Ethyl-1-(4-hydroxy-3-methyl-phenyl)-propyl]-benzo[b]thiophene-6-carboxylic acid methyl ester

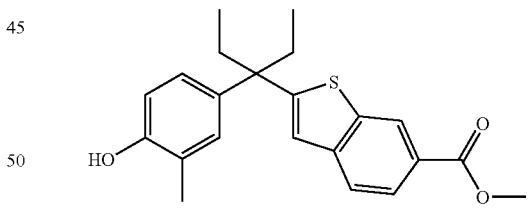

A solution of 2-[1-ethyl-1-(4-hydroxy-3-methyl-phenyl)-propyl]-benzo[b]thiophene-6-carboxylic acid (3.98 g, 11.23 mmol) in MeOH (100 mL) is treated with H₂SO₄ (concentrated, 1.0 mL). The mixture is stirred at 80° C. for 8 h and neutralized with aqueous NaHCO₃. The MeOH is removed under vacuum and the residue is extracted with EtOAc (2×100 mL). The combined organic layer is dried over Na₂SO₄, concentrated and purified by silica gel column chromatography (20% EtOAc/Hex) to give the product (4.05 g, 98%).

MS (ES) m/e 367.1 (M−1).

D. 2-{1-[4-(3,3-dimethyl-2-oxo-butoxy)-3-methyl-phenyl]-1-ethyl-propyl}-benzo[b]thiophene-6-carboxylic acid methyl ester

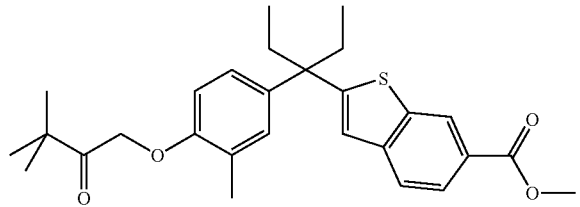

A solution of 2-[1-ethyl-1-(4-hydroxy-3-methyl-phenyl)-propyl]-benzo[b]thiophene-6-carboxylic acid methyl ester (4.05 g, 11.0 mmol) and 1-bromopinacolone (2.36 g, 13.2 mmol) in acetone (100 mL) is treated with $K_2CO_3$ (3.04 g, 22.0 mmol) and stirred at RT for 16 h. The mixture is filtered, and the filtrate is concentrated. The residue is purified by silica gel column chromatography (10-15% EtOAc/Hex) to provide the title compound (4.50 g, 88%).

MS (ES) m/e 484.2 (M+18).

E. 2-{1-[4-(3,3-Dimethyl-2-oxo-butoxy)-3-methyl-phenyl]-1-ethyl-propyl}-benzo[b]thiophene-6-carboxylic acid 2-{1-[4-(3,3-Dimethyl-2-oxo-butoxy)-3-methyl-phenyl]-1-ethyl-propyl}-benzo[b]thiophene-6-carboxylic acid methyl ester (120 mg, 0.257 mmol) is hydrolyzed as in Step E11 to give the title compound (72 mg, 62%).

MS (ES) m/e 451.2 (M-1), 470.2 (M+18).

Example 8

Preparation of 2-{1-Ethyl-1-[4-(2-hydroxy-3,3-dimethyl-butoxy)-3-methyl-phenyl]-propyl}-benzo[b]thiophene-6-carboxylic acid

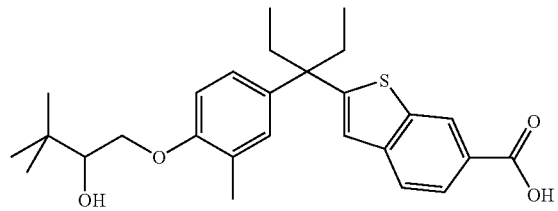

2-{1-[4-(3,3-Dimethyl-2-oxo-butoxy)-3-methyl-phenyl]-1-ethyl-propyl}-benzo[b]thiophene-6-carboxylic acid (53 mg, 0.117 mmol) is reduced by $NaBH_4$ (9 mg, 0.234 mmol) as in a reaction analogous to Example 2 to afford the title compound (53 mg, 99%).

MS (ES) m/e 453.2 (M-1), 472.2 (M+18).

Example 9

Preparation of 2-{1-[4-(3,3-Dimethyl-2-oxo-butoxy)-3-methyl-phenyl]-1-ethyl-propyl}-benzo[b]thiophene-6-carboxylic acid dimethylamide

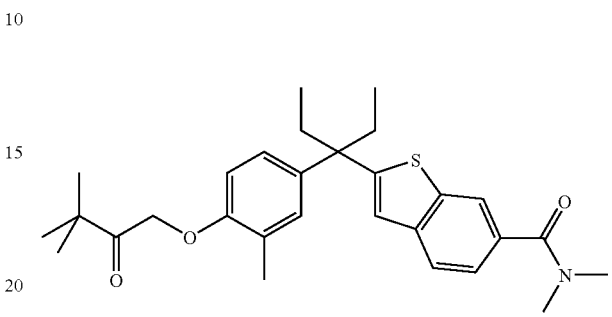

2-{1-[4-(3,3-Dimethyl-2-oxo-butoxy)-3-methyl-phenyl]-1-ethyl-propyl}-benzo[b]thiophene-6-carboxylic acid (175 mg, 0.387 mmol), DIMAP (142 mg, 1.16 mmol), EDC (111 mg, 0.580 mmol), and dimethylamine hydrochloride (47 mg, 0.580 mmol) are reacted analogous to Example 3 to afford the title compound (140 mg, 76%).

MS (ES) m/e 480.2 (M+1).

Example 10

Preparation of 2-{1-Ethyl-1-[4-(2-hydroxy-3,3-dimethyl-butoxy)-3-methyl-phenyl]-propyl}-benzo[b]thiophene-6-carboxylic acid dimethylamide

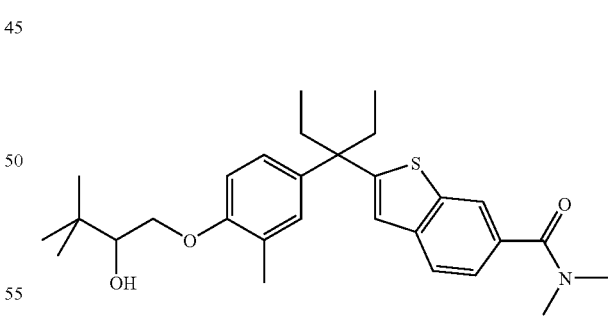

2-{1-[4-(3,3-Dimethyl-2-oxo-butoxy)-3-methyl-phenyl]-1-ethyl-propyl}-benzo[b]thiophene-6-carboxylic acid dimethylamide (90 mg, 0.188 mmol) is reduced using $NaBH_4$ (14 mg, 0.376 mmol) in a reaction analogous to Example 2 to afford the title compound (90 mg, 100%).

MS (ES) m/e 482.2 (M+1).

Example 11

Preparation of [(2-{1-[4-(3,3-dimethyl-2-oxo-butoxy)-3-methyl-phenyl]-1-ethyl-propyl}-benzo[b]thiophene-6-carbonyl)-amino]-acetic acid

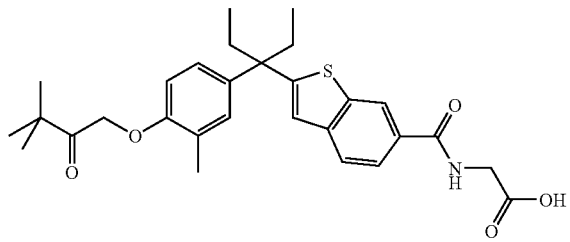

2-{1-[4-(3,3-Dimethyl-2-oxo-butoxy)-3-methyl-phenyl]-1-ethyl-propyl}-benzo[b]thiophene-6-carboxylic acid (175 mg, 0.387 mmol), DMAP (142 mg, 1.16 mmol), EDC (111 mg, 0.580 mmol), and glycine methyl ester hydrochloride (73 mg, 0.580 mmol) are reacted and hydrolyzed in a sequence analogous to Example 5 to afford the title compound (180 mg, 91%).

MS (ES) m/e 508.2 (M−1), 510.1 (M+1).

Example 12

Preparation of [(2-{1-Ethyl-1-[4-(2-hydroxy-3,3-dimethyl-butoxy)-3-methyl-phenyl]-propyl}-benzo[b]thiophene-6-carbonyl)-amino]-acetic acid

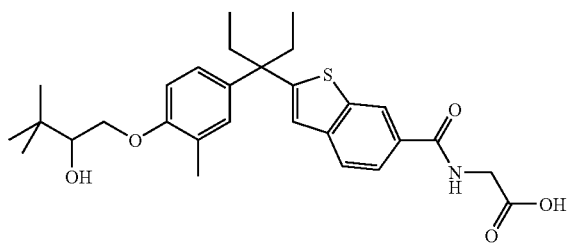

[(2-{1-[4-(3,3-Dimethyl-2-oxo-butoxy)-3-methyl-phenyl]-1-ethyl-propyl}-benzo[b]thiophene-6-carbonyl)-amino]-acetic acid (135 mg, 0.265 mmol) is reduced using NaBH$_4$ (20 mg, 0.530 mmol) as in example 2 to afford the title compound (135 mg, 99%).

MS (ES) m/e 512.2 (M+1), 510.2 (M−1).

Example 13

Preparation of 5-{1-[4-(3,3-dimethyl-2-oxo-butoxy)-3-methyl-phenyl]-1-ethyl-propyl}-benzo[b]thiophene-2-carboxylic acid

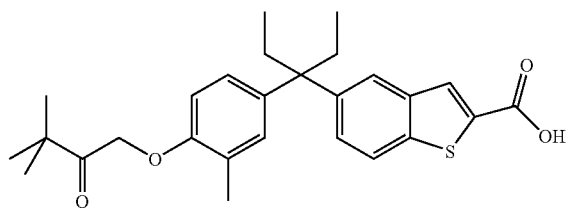

A. 1-(1-Ethyl-propenyl)-4-fluoro-benzene

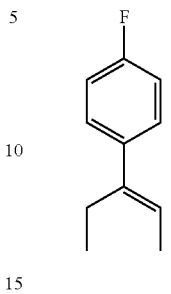

A solution of 4-fluoro-benzoic acid methyl ester (19.1 g, 114 mmol) in THF (300 mL) at −78° C. is treated with ethylmagnesium bromide (135 mL, 3.0 M). The reaction mixture is allowed to warm to 0° C. over 30 min and quenched with HCl (350 mL, 1.0 M). THF is removed under vacuum, and the residue is extracted with EtOAc (3×100 mL). The organic layer is dried over Na$_2$SO$_4$ and concentrated. The intermediate tertiary alcohol is dissolved in CH$_2$Cl$_2$ (200 mL), cooled to −40° C., and treated with BF$_3$-Et$_2$O (11.5 g, 91.0 mol). The reaction mixture is allowed to warm to 0° C. over 30 min and quenched with water (50 mL). The organic layer is dried over Na$_2$SO$_4$ and concentrated. The residue is purified using silica gel column chromatography (5% EtOAc/Hex) to afford the title compound (16.8 g, 90%).

H-NMR (ppm, CDCl$_3$), δ: 7.27 (2 H, m), 6.97 (2 H, m), 5.66 (1 H, q, J=7.0 Hz), 2.49 (2 H, q, J=7.0 Hz), 1.78 (3 H, d, J=7.0 Hz), 0.98 (3 H, t, J=7.0 Hz).

B. 5-(1-Ethyl-propenyl)-2-fluoro-benzaldehyde

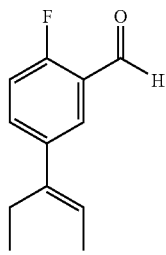

A solution of 1-(1-ethyl-propenyl)-4-fluoro-benzene (15.3 g, 93.2 mmol) in THF (150 mL) at −78° C. is treated with n-BuLi (70 mL, 1.6 M). The reaction mixture is allowed to warm to 0° C. over 60 min, cooled to −78° C., and treated with DMF (10.2 g, 140 mmol). The mixture is stirred for 10 min and quenched with HOAc (10 mL) and water (200 mL). The mixture is allowed to warm to RT, and the THF is removed under vacuum. The residue is extracted with EtOAc (2×100 mL, and the organic layer is dried over Na$_2$SO$_4$ andconcentrated. The crude product is purified using silica gel column chromatography (7% EtOAc/Hex) to afford the title compound (8.70 g, 49%).

H-NMR (ppm, CDCl$_3$), δ: 10.34 (1 H, s), 7.79 (1 H, dd, J=2.7, 6.6 Hz), 7.54 (1 H, m), 7.09 (1 H, dd, J=1.3, 9.7 Hz), 5.72 (1 H, q, J=7.0 Hz), 2.50 (2 H, q, J=7.5 Hz), 1.79 (3 H, d, J=7.0 Hz), 0.97 (3 H, t, J=7.5 Hz).

C. 5-(1-Ethyl-propenyl)-benzo[b]thiophene-2-carboxylic acid ethyl ester

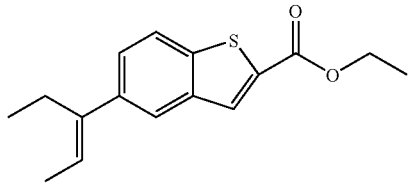

A solution of 5-(1-ethyl-propenyl)-2-fluoro-benzaldehyde (8.70 g, 45.3 mmol) in DMF (40 mL) is treated with mercapto-acetic acid ethyl ester (8.16 g, 67.9 mmol) and $K_2CO_3$ (12.5 g, 90.6 mmol). The resulting suspension is stirred at 80° C. for 60 min and quenched with water (300 mL). The mixture is extracted with EtOAc (2×200 mL), and the organic layer is dried over $Na_2SO_4$, concentrated, and purified using silica gel column chromatography (6% EtOAc/Hex), to give the title compound as an oil (11.0 g, 89%).

H-NMR (ppm, $CDCl_3$), δ: 8.01 (1 H; s), 7.78 (1 H, d, J=1.8 Hz), 7.75 (1 H, d, J=8.4 Hz), 7.44 (1 H, dd, J=1.8, 8.4 Hz), 5.75 (1 H, q, J=7.0 Hz), 4.41 (2 H, q, J=7.0 Hz), 2.58 (2 H, q, J=7.5 Hz), 1.82 (3 H, d, J=7.0 Hz), 1.42 (3 H, t, J=7.0 Hz), 0.97 (3 H, t, J=7.5 Hz).

D. 5-[1-Ethyl-1-(4-hydroxy-3-methyl-phenyl)-propyl]-benzo[b]thiophene-2-carboxylic acid ethyl ester

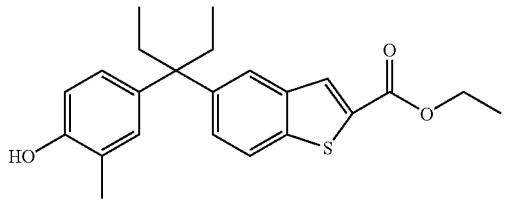

5-(1-Ethyl-propenyl)-benzo[b]thiophene-2-carboxylic acid ethyl ester (5.50 g, 20.0 mmol), o-cresol (4.33 g, 40.0 mmol), and $BF_3$-$Et_2O$ (10 mL) are reacted analogous to Example 1C to afford the title compound (5.97 g, 78%).

MS (ES) m/e 381.3 (M−1), 383.4 (M+1).

E. 5-{1-[4-(3,3-Dimethyl-2-oxo-butoxy)-3-methyl-phenyl]-1-ethyl-propyl}-benzo[b]thiophene-2-carboxylic acid ethyl ester

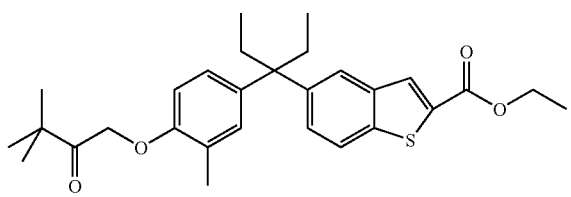

5-[1-Ethyl-1-(4-hydroxy-3-methyl-phenyl)-propyl]-benzo[b]thiophene-2-carboxylic acid ethyl ester (5.97 g, 15.6 mmol), 1-bromopinacolone (4.20 g, 23.4 mmol), and $K_2CO_3$ (6.46 g, 46.8 mmol) in acetone (100 mL) are reacted analogous to Example 1D to provide the title compound (7.10 g, 95%).

MS (ES) m/e 498.4 (M+18).

F. 5-{1-[4-(3,3-Dimethyl-2-oxo-butoxy)-3-methyl-phenyl]-1-ethyl-propyl}-benzo[b]thiophene-2-carboxylic acid 5-{1-[4-(3,3-Dimethyl-2-oxo-butoxy)-3-methyl-phenyl]-1-ethyl-propyl}-benzo[b]thiophene-2-carboxylic acid ethyl ester (2.50 g, 5.20 mmol) is hydrolyzed as in Step E11 to give the title compound (2.20 g, 94%).

MS (ES) m/e 451.2 (M−1), 470.2 (M+18).

Example 14

Preparation of 5-{1-ethyl-1-[4-(2-hydroxy-3,3-dimethyl-butoxy)-3-methyl-phenyl]-propyl}-benzo[b]thiophene-2-carboxylic acid

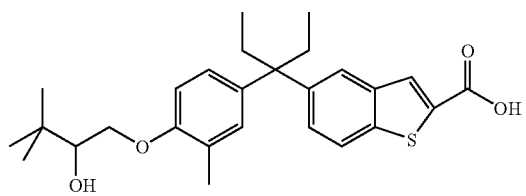

5-{1-[4-(3,3-Dimethyl-2-oxo-butoxy)-3-methyl-phenyl]-1-ethyl-propyl}-benzo[b]thiophene-2-carboxylic acid (0.280 g, 0.619 mmol) is reduced using $NaBH_4$ (14 mg, 0.376 mmol) analogous to Example 2 to afford the title compound (0.241 g, 86%).

MS (ES) m/e 453.1 (M−1), 472.2 (M+18).

Example 15

Preparation of [(5-{1-[4-(3,3-dimethyl-2-oxo-butoxy)-3-methyl-phenyl]-1-ethyl-propyl}-benzo[b]thiophene-2-carbonyl)-amino]-acetic acid

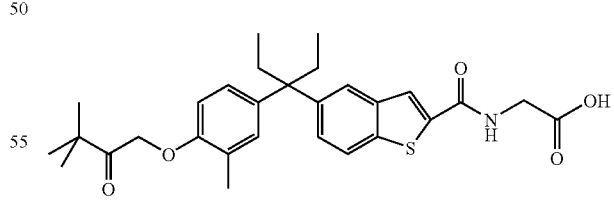

5-{1-[4-(3,3-Dimethyl-2-oxo-butoxy)-3-methyl-phenyl]-1-ethyl-propyl}-benzo[b]thiophene-2-carboxylic acid (310 mg, 0.686 mmol), DMAP (167 mg, 1.37 mmol), EDC (197 mg, 1.03 mmol), and glycine methyl ester hydrochloride (172 mg, 1.37 mmol) are reacted and hydrolyzed in a sequence analogous to Example 5 to afford the title compound (150 mg, 43%).

MS (ES) m/e 508.2 (M−1), 510.1 (M+1).

Example 16

Preparation of [(5-{1-ethyl-1-[4-(2-hydroxy-3,3-dimethyl-butoxy)-3-methyl-phenyl]-propyl}-benzo[b]thiophene-2-carbonyl)-amino]-acetic acid

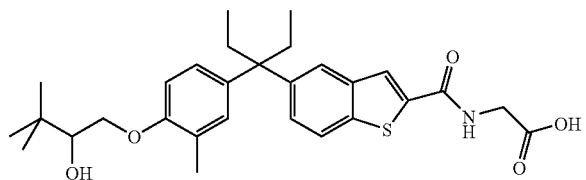

[(5-{1-[4-(3,3-Dimethyl-2-oxo-butoxy)-3-methyl-phenyl]-1-ethyl-propyl}-benzo[b]thiophene-2-carbonyl)-amino]-acetic acid (90 mg, 0.177 mmol) is reduced using NaBH₄ (13 mg, 0.354 mmol) in a reaction analogous to Example 2 to afford the title compound (73 mg, 81%).

MS (ES) m/e 510.2 (M−1), 512.2 (M+1).

Example 17

Preparation of 2-{1-[4-(3,3-dimethyl-2-oxo-butoxy)-3-methyl-phenyl]-1-ethyl-propyl}-benzo[b]thiophene-5-carboxylic acid

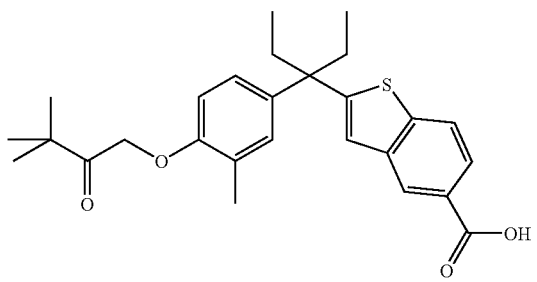

A. 5-Methoxy-benzo[b]thiophene-2-carboxylic acid ethyl ester

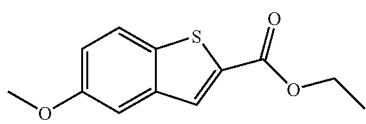

A solution of 2-fluoro-5-methoxy-benzaldehyde (4.35 g, 28.2 mmol) in DMF (30 mL) is added mercapto-acetic acid ethyl ester (3.71 mL, 33.9 mmol) and K₂CO₃ (7.86 g, 57.0 mmol). The resulting suspension is stirred at 80° C. for 60 min and quenched with water (300 mL). The mixture is extracted with EtOAc (2×200 mL), and the organic layer is dried over Na₂SO₄, concentrated, and purified by silica gel column chromatography (10% EtOAc/Hex), to give the title compound as an oil (4.40 g, 66%).

H-NMR (ppm, CDCl₃), δ: 7.97 (1 H, s), 7.70 (1 H, d, J=8.8 Hz), 7.27 (1 H, d, J=2.6 Hz), 7.09 (1 H, dd, J=2.6, 8.8 Hz), 4.41 (2 H, q, J=7.0 Hz), 3.88 (3 H, s), 1.42 (3 H, t, J=7.0 Hz).

B. 3-(5-Methoxy-benzo[b]thiophen-2-yl)-pentan-3-ol

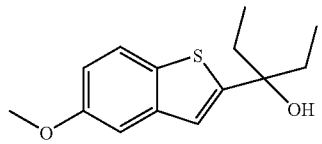

5-Methoxy-benzo[b]thiophene-2-carboxylic acid ethyl ester (4.13 g, 17.5 mmol) in THF (100 mL) at −78° C. is treated with ethylmagnesium bromide (17.5 mL, 3.0 M). The reaction mixture is allowed to warm to RT over 30 min and is stirred for 10 min. The mixture is quenched with water (40 mL) and acidified with HCl (50 mL, 1.0 M). THF is removed under vacuum, and the residue is extracted with EtOAc (2×40 mL). The organic layer is dried over Na₂SO₄, concentrated, and purified using silica gel column chromatography (10% EtOAc/Hex) to give the title compound (4.53 g, 97%).

H-NMR (ppm, CDCl₃), δ: 7.63 (1 H, d, J=8.8 Hz), 7.17 (1 H, d, J=2.2 Hz), 7.03 (1 H, s), 6.92 (1 H, dd, J=2.6, 8.8 Hz), 3.86 (3 H, s), 1.91 (4 H, q, J=7.0 Hz), 0.91 (6 H, t, J=7.0 Hz).

C. 4-[1-Ethyl-1-(5-methoxy-benzo[b]thiophen-2-yl)-propyl]-2-methyl-phenol

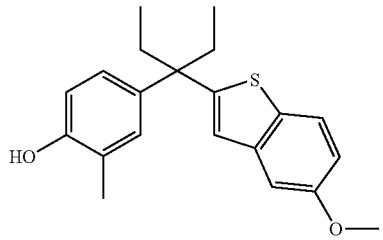

3-(5-Methoxy-benzo[b]thiophen-2-yl)-pentan-3-ol (2.16 g, 8.63 mmol), o-cresol (4.66 g, 43.1 mmol), and BF₃-Et₂O (1.64 mL, 12.9 mmol) are reacted analogous to Example 1C to afford the title compound (2.29 g, 78%).

MS (ES) m/e 339.2 (M−1), 341.3 (M+1).

D. 1-{4-[1-Ethyl-1-(5-methoxy-benzo[b]thiophen-2-yl)-propyl]-2-methyl-phenoxy}-3,3-dimethyl-butan-2-one (2131468) (PF1-A03098-163)

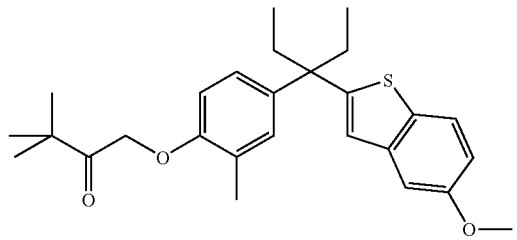

4-[1-Ethyl-1-(5-methoxy-benzo[b]thiophen-2-yl)-propyl]-2-methyl-phenol (7.80 g, 22.9 mmol), 1-bromopinacolone (8.20 g, 45.8 mmol), and K₂CO₃ (6.32 g, 45.8 mmol) in acetone (100 mL) are reacted analogous to Example 1D to provide the title compound (9.20 g, 92%).

H-NMR (ppm, CDCl₃), δ: 7.53 (1 H, d, J=8.8 Hz), 7.15 (1 H, d, J=2.6 Hz), 7.02-7.06 (3 H, m), 6.87 (1 H, dd, J=2.6, 8.8

Hz), 6.50 (1 H, d, J=8.4 Hz), 4.84 (2 H, s), 3.85 (3 H, s), 2.25 (3 H, s), 2.15 (4 H, q, J=7.5 Hz), 1.26 (9 H, s), 0.73 (6 H, t, J=7.5 Hz).

E. 1-{4-[1-Ethyl-1-(5-hydroxy-benzo[b]thiophen-2-yl)-propyl]-2-methyl-phenoxy}-3,3-dimethyl-butan-2-one

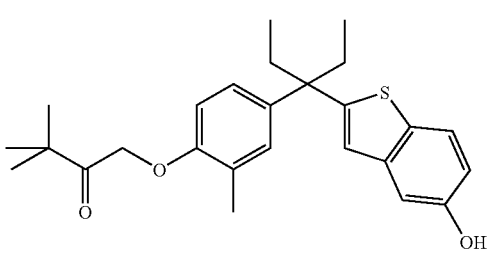

A solution of 1-{4-[1-ethyl-1-(5-methoxy-benzo[b]thiophen-2-yl)-propyl]-2-methyl-phenoxy}-3,3-dimethyl-butan-2-one (0.86 g, 1.96 mmol) in $CH_2Cl_2$ (15.0 mL) at 0° C. is treated with $BBr_3$ (3.0 mL, 2.94 mmol). The mixture is stirred for 2 h and quenched with water (10 mL). The aqueous layer is extracted with $CH_2Cl_2$ (30 mL). The organic layer is concentrated and purified using silica gel column chromatography (25% EtOAc/Hex) to afford the title compound (0.412 g, 50%).

H-NMR (ppm, $CDCl_3$), δ: 7.50 (1 H, d, J=8.4 Hz), 7.10 (1 H, d, J=2.6 Hz), 7.02-7.06 (2 H, m), 6.98 (1 H, s), 6.78 (1 H, dd, J=2.6, 8.8 Hz), 6.51 (1 H, d, J=8.4 Hz), 4.84 (2 H, s), 2.25 (3 H, s), 2.15 (4 H, q, J=7.5 Hz), 1.26 (9 H, s), 0.73 (6 H, t, J=7.5 Hz).

F. Trifluoromethanesulfonic acid 2-{1-[4-(3,3-dimethyl-2-oxo-butoxy)-3-methyl-phenyl]-1-ethyl-propyl}-benzo[b]thiophen-5-yl ester

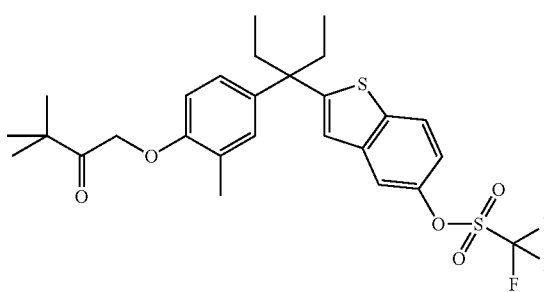

A solution of 1-{4-[1-ethyl-1-(5-hydroxy-benzo[b]thiophen-2-yl)-propyl]-2-methyl-phenoxy}-3,3-dimethyl-butan-2-one (3.21 g, 7.56 mmol) in $CH_2Cl_2$ (50 mL) at −78° C. is treated with 2,6-lutidine (1.32 mL, 11.3 mmol) and trifluoromethanesulfonic acid anhydride (1.78 mL, 10.6 mmol). The mixture is stirred and allowed to warm to −20° C. over 60 min. The mixture is quenched with water (5.0 mL). The organic layer is concentrated and purified using silica gel column chromatography (10% EtOAc/Hex) to afford the title compound (4.20 g, 99%).

H-NMR (ppm, $CDCl_3$), δ: 7.69 (1 H, d, J=8.8 Hz), 7.57 (1 H, d, J=2.2 Hz), 7.13 (1 H, s), 7.11 (1 H, dd, J=2.2, 8.8 Hz), 7.04 (1 H, s), 7.01 (1 H, dd, J=2.2, 8.8 Hz), 6.52 (1 H, d, J=8.4 Hz), 4.84 (2 H, s), 2.27 (3 H, s), 2.15 (4 H, q, J=7.5 Hz), 1.26 (9 H, s), 0.74 (6 H, t, J=7.5 Hz).

G. 2-{1-[4-(3,3-Dimethyl-2-oxo-butoxy)-3-methyl-phenyl]-1-ethyl-propyl}-benzo[b]thiophene-5-carboxylic acid methyl ester

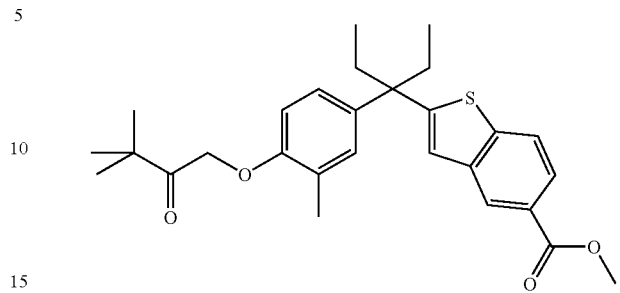

A solution of trifluoromethanesulfonic acid 2-{1-[4-(3,3-dimethyl-2-oxo-butoxy)-3-methyl-phenyl]-1-ethyl-propyl}-benzo[b]thiophen-5-yl ester (4.10 g, 7.36 mmol) in DMSO (15 mL) and MeOH (10 mL) is treated with $Pd(OAc)_2$ (0.169 g), DPPB (0.368 g) and $Et_3N$ (5.3 mL). The mixture is stirred under CO (100 psi) at 80° C. for 4 h. The MeOH is removed in vacuum, and the residue is poured into water (150 mL) and extracted with EtOAc (2×50 mL). The organic layer is dried over $Na_2SO_4$, concentrated, purified using silica gel column chromatography (10% EtOAc/Hex), to give the title compound as an oil (3.10 g, 90%).

H-NMR (ppm, $CDCl_3$), δ: 8.38 (1 H, d, J=2.6 Hz), 7.87 (1 H, dd, J=1.3, 8.4 Hz), 7.70 (1 H, d, J=8.8 Hz), 7.19 (1 H, s), 7.05 (1 H, s), 7.01 (1 H, dd, J=2.2, 8.4 Hz), 6.52 (1 H, d, J=8.4 Hz), 4.84 (2 H, s), 3.94 (3 H, s), 2.26 (3 H, s), 2.18 (4 H, q, J=7.5 Hz), 1.26 (9 H, s), 0.74 (6 H, t, J=7.5 Hz). MS (ES) m/e 484.4 (M+18).

H. 2-{1-[4-(3,3-Dimethyl-2-oxo-butoxy)-3-methyl-phenyl]-1-ethyl-propyl}-benzo[b]thiophene-5-carboxylic acid.

2-{1-[4-(3,3-Dimethyl-2-oxo-butoxy)-3-methyl-phenyl]-1-ethyl-propyl}-benzo[b]thiophene-5-carboxylic acid methyl ester (2.95 g, 6.32 mmol) is hydrolyzed as in Step E11 to give the title compound (2.80 g, 98%).

MS (ES) m/e 451.2 (M−1), 470.2 (M+18).

Example 18

Preparation of 2-{1-ethyl-1-[4-(2-hydroxy-3,3-dimethyl-butoxy)-3-methyl-phenyl]-propyl}-benzo[b]thiophene-5-carboxylic acid

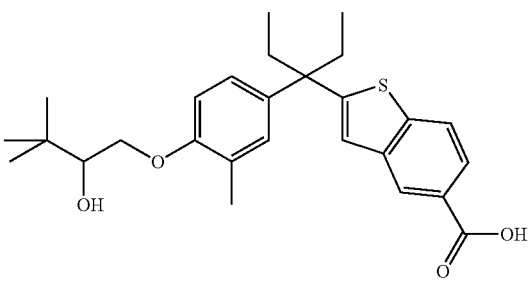

2-{1-[4-(3,3-Dimethyl-2-oxo-butoxy)-3-methyl-phenyl]-1-ethyl-propyl}-benzo[b]thiophene-5-carboxylic acid (330 mg, 0.730 mmol) is reduced using $NaBH_4$ (55 mg, 1.46 mmol) in a reaction analogous to Example 2 to afford the title compound (0.306 g, 92%).

MS (ES) m/e 453.2 (M−1), 472.2 (M+18).

Example 19

Preparation of [(2-{1-[4-(3,3-Dimethyl-2-oxo-butoxy)-3-methyl-phenyl]-1-ethyl-propyl}-benzo[b]thiophene-5-carbonyl)-amino]-acetic acid

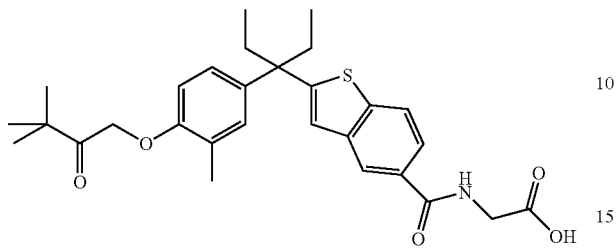

2-{1-[4-(3,3-Dimethyl-2-oxo-butoxy)-3-methyl-phenyl]-1-ethyl-propyl}-benzo[b]thiophene-5-carboxylic acid (310 mg, 0.686 mmol), DMAP (167 mg, 1.37 mmol), EDC (197 mg, 1.03 mmol), and glycine methyl ester hydrochloride (172 mg, 1.37 mmol) are reacted and hydrolyzed in a sequence analogous to Example 5 to afford the title compound (246 mg, 70%).

MS (ES) m/e 508.2 (M−1), 510.1 (M+1).

Example 20

Preparation of [(2-{1-Ethyl-1-[4-(2-hydroxy-3,3-dimethyl-butoxy)-3-methyl-phenyl]-propyl}-benzo[b]thiophene-5-carbonyl)-amino]-acetic acid

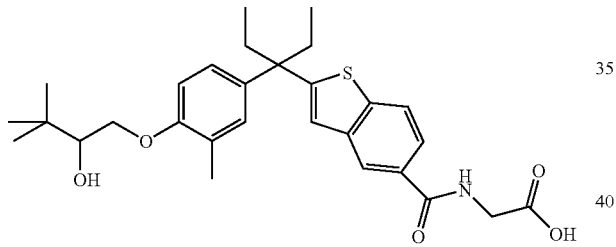

[(2-{1-[4-(3,3-Dimethyl-2-oxo-butoxy)-3-methyl-phenyl]-1-ethyl-propyl}-benzo[b]thiophene-5-carbonyl)-amino]-acetic acid (150 mg, 0.295 mmol) is reduced using NaBH$_4$ (22 mg, 0.589 mmol) analogous to Example 2 to afford the title compound (130 mg, 86%).

MS (ES) m/e 510.2 (M−1), 512.2 (M+1).

Example 21

Preparation of 2-{1-[4-(3,3-Dimethyl-2-oxo-butoxy)-3-methyl-phenyl]-1-ethyl-propyl}-benzo[b]thiophene-5-carboxylic acid dimethylamide

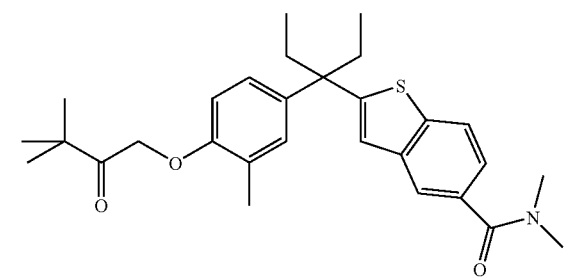

A solution of 2-{1-[4-(3,3-dimethyl-2-oxo-butoxy)-3-methyl-phenyl]-1-ethyl-propyl}-benzo[b]thiophene-5-carboxylic acid (210 mg, 0.464 mmol) in CH$_2$Cl$_2$ (5.0 mL) is treated with Et$_3$N (1.0 mL), HOBT (94 mg, 0.70 mmol), and EDC (134 mg, 0.70 mmol). The mixture is stirred for 10 min at RT, and dimethylamine (1.0 mL, 2.0 M in THF) is added. The reaction mixture is stirred for 18 h, loaded onto a silica gel column, and eluted with 65% EtOAc/Hex to afford the title compound (90 mg, 41%).

MS (ES) m/e 480.4 (M+1).

Example 22

Preparation of 2-{1-Ethyl-1-[4-(2-ethyl-2-hydroxy-butoxy)-3-methyl-phenyl]-propyl}benzo[b]thiophene-6-carboxylic acid

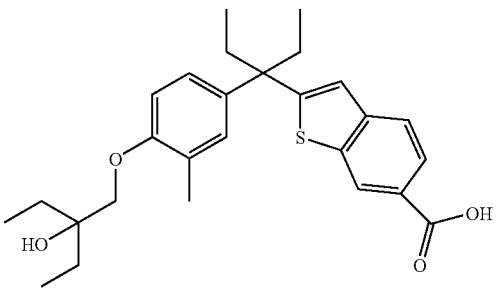

A. {4-[1-Ethyl-1-(6-methoxy-benzo[b]thiophen-2-yl)-propyl]-2-methyl-phenoxy}-acetic acid methyl ester

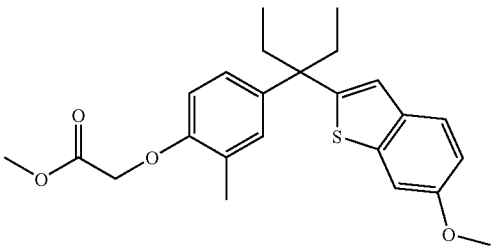

To a mixture of 4-[1-ethyl-1-(6-methoxy-benzo[b]thiophen-2-yl)-propyl]-2-methyl-phenol (2.53 g, 7.43 mmol) and acetonitrile (25 mL) is added methyl bromoacetate (0.84 mL, 8.92 mmol), powdered potassium carbonate (4.10 g, 29.72 mmol), and potassium iodide (0.12 g, 0.74 mmol). The resulting slurry is stirred at reflux temperature for 2 h, filtered, and concentrated. The residue is dissolved in diethyl ether (100 mL), washed with water (75 ml), brine (75 mL), dried over MgSO$_4$, filtered, and concentrated to give the title compound (1.5 g, 3.63 mmol, 49%). $^1$H NMR (CDCl$_3$), δ 0.74 (t, J =7.2 Hz, 6H), 2.17 (q, J =14.7, 7.5 Hz, 4H), 2.25 (s, 3H), 2.30 (s, 2H), 3.80 (s, 3H), 3.86 (s, 3H), 3.60 (d, J=8.6 Hz, 1H), 6.89 (dd, J=8.6, 2.5 Hz, 1H), 7.04 (s, 1H), 7.07 (s, 1H), 7.16 (d, J=2.5 Hz, 1H), 7.55 (d, J=8.9 Hz, 1H).

B. 3-{4-[1-Ethyl-1-(6-methoxy-benzo[b]thiophen-2-yl)-propyl]-2-methyl-phenoxymethyl}-pentan-3-ol

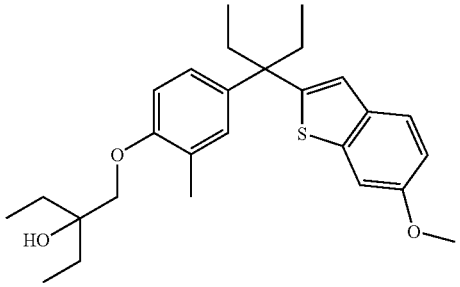

To a mixture of {4-[1-ethyl-1-(6-methoxy-benzo[b]thiophen-2-yl)-propyl]-2-methyl-phenoxy}-acetic acid methyl ester (1.50 g, 3.64 mmol) and THF (20 mL) is added ethyl magnesium bromide (3.0 mL, 9.1 mmol, 3M in THF). The solution is heated at a reflux for 3 h, diluted with saturated ammonia chloride solution (80 mL), extracted with diethyl ether (2×75 mL), dried over MgSO$_4$, filtered, and concentrated. The residue is purified by silica gel chromatography (10% to 30% EtOAc gradient) to give the title compound (0.90 g, 2.04 mmol, 56%). $^1$H NMR (CDCl$_3$), δ 0.75 (t, J=7.6 Hz, 6H), 0.95 (t, J=7.4 Hz, 6H), 1.68 (q, J=14.8, 7.5 Hz, 4H), 2.13-2.24 (m, 7H), 3.81 (s, 2H), 3.86 (s, 3H), 6.73 (dd, J =8.2 Hz, 1H), 6.89 (dd, J =8.8, 2.6 Hz, 1H), 7.06 (s, 2H), 7.09 (dd, J=8.4, 2.5 Hz, 1H), 7.17 (d, J=2.7 Hz, 1H), 7.55 (d, J=8.8 Hz, 1H). LC/MS (m/z): calcd. for C$_{27}$H$_{37}$O$_3$S (M+H)$^+$: 441.3; found: 441.2.

C. 2-{1-Ethyl-1-[4-(2-ethyl-2-hydroxy-butoxy)-3-methyl-phenyl]-propyl}benzo[b]thiophen-6-ol

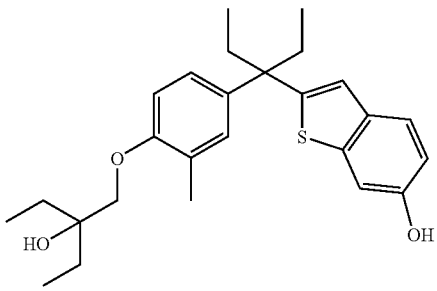

To a solution of 3-{4-[1-ethyl-1-(6-methoxy-benzo[b]thiophen-2-yl)-propyl]-2-methyl-phenoxymethyl}-3-pentan-3-ol (0.80 g, 1.82 mmol) and DMF (10 mL) is added NaSEt (1.53 g, 18.15 mmol). The resulting solution is heated at 100° C. overnight, diluted with diethyl ether (50 mL), washed with water (3×50 mL), brine (50 mL), dried with MgSO$_4$, filtered and concentrated. The resulting residue is purified by silica gel chromatography (10% to 40% EtOAc gradient) to give the title compound (0.67 g, 1.57 mmol, 87%). $^1$H NMR (CDCl$_3$), δ 0.75 (t, J=7.2 Hz, 6H), 0.95 (t, J=7.4 Hz, 6H), 1.67 (q, J=15.1, 7.4 Hz, 4H), 2.12-2.24 (m, 7H), 3.82 (s, 2H), 6.73 (d, J=8.6 Hz, 1H), 6.79 (dd, J=9.0, 2.6 Hz, 1H), 6.79 (dd, J=9.0, 2.6 Hz, 1H), 7.00 (s, 1H), 7.05 (d, J=2.2 Hz, 1H), 7.08 (dd, J=8.2, 2.6 Hz, 1H), 7.11 (d, J=2.2 Hz, 1H), 7.49 (d, J=9.0 Hz, 1H). LC/MS (m/z): calcd. for C$_{26}$H$_{35}$O$_3$S (M+H)$^+$: 427.2; found: 427.1.

D. Trifluoro-methanesulfonic acid 2-{1-ethyl-1-[4-(2-ethyl-2-hydroxy-butoxy)-3-methyl-phenyl]-propyl}-benzo[b]thiophen-6-yl ester

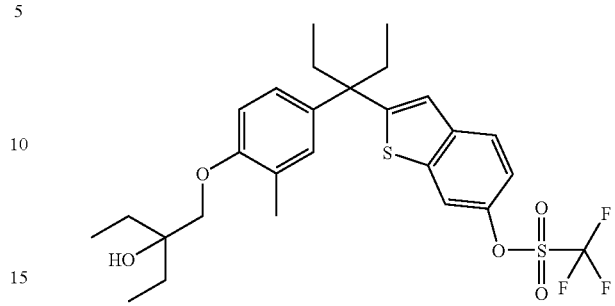

To a solution of 2-{1-Ethyl-1-[4-(2-ethyl-2-hydroxy-butoxy)-3-methyl-phenyl]-propyl}benzo[b]thiophen-6-ol (0.67 g, 1.57 mmol) and dichloromethane (5 mL) is added NEt$_3$ (0.44 mL, 3.14 mmol). The solution is cooled to 0° C., and triflouromethane-sulfonic anhydride (0.28 mL, 1.65 mmol) is added. The solution is warmed to RT, diluted with diethyl ether (30 mL), washed with saturated NaHCO$_3$ (20 mL), dried with MgSO$_4$, filtered, and concentrated to give the title compound (0.22 g, 0.40 mmol, 85%). $^1$H NMR (CDCl$_3$), δ 0.75 (t, J=7.3 Hz, 6H), 0.95 (t, J=7.5 Hz, 6H), 1.68 (q, J=14.8, 7.6 Hz, 4H), 2.14-2.27 (m, 7H), 3.82 (s, 2H), 6.74 (d, J=8.3 Hz, 1H), 7.03 (d, J=2.1 Hz, 1H), 7.08 (dd, J=8.7, 2.5 Hz, 1H), 7.13(dd, J=8.7, 2.9 Hz, 1H), 7.14 (s, 1H), 7.58 (d, J=2.1 Hz, 1H), 7.70 (d, J=8.3 Hz, 1H). LC/MS (m/z): calcd. for C$_{27}$H$_{34}$F$_3$O$_5$S$_2$ (M+H)$^+$; 559.2; found: 576.1.

E. 2-{1-Ethyl-1-[4-(2-ethyl-2-hydroxy-butoxy)-3-methyl-phenyl]-propyl}benzo[b]thiophene-6-carboxylic acid methyl ester

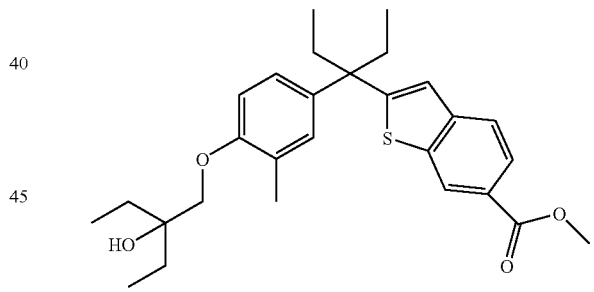

To a solution of trifluoro-methanesulfonic acid 2-{1-ethyl-1-[4-(2-ethyl-2-hydroxy-butoxy)-3-methyl-phenyl]-propyl}-benzo[b]thiophen-6-yl ester (0.66 g, 1.19 mmol) and DMSO (15 mL) is added MeOH (10 mL), NEt$_3$ (0.77 mL), DPPB (0.054 g, 0.13 mmol), Pd(OAc)$_2$ (0.024, 0.01 mmol), and CO (100 psi). The solution is heated at 80° C. overnight, diluted with 1M HCl (100 mL), and extracted with diethyl ether (2×50 mL). The combined organic layers are washed with water (75 mL) then brine (75 mL), dried MgSO$_4$, filtered, and concentrated. The residue is purified by silica gel chromatography (10% to 40% EtOAc gradient) to give the title compound (0.84 g, 2.04 mmol, 68%). $^1$H NMR (CDCl$_3$), δ 0.75 (t, J=7.2 Hz, 6H), 0.95 (t, J=7.7 Hz, 6H), 1.67 (q, J=14.6, 7.5 Hz, 4H), 2.14-2.25 (m, 7H), 3.81 (s, 2H), 3.95 (s, 3H), 6.73 (d, J=8.7 Hz, 1H), 7.04 (d, J=2.2 Hz, 1H), 7.08 (dd, J=8.4, 2.2 Hz, 1H), 7.20 (s, 1H), 7.71 (d, J=8.5 Hz, 1H), 7.89 (dd, J=8.4, 1.7 Hz, 1H), 8.39 (d, J=1.7 Hz, 1H). LC/MS (m/z): calcd. for C$_{28}$H$_{37}$O$_4$S (M+H)$^+$: 469.2; found: 486.2.

F. 2-{1-Ethyl-1-[4-(2-ethyl-2-hydroxy-butoxy)-3-methyl-phenyl]-propyl}benzo[b]thiophene-6-carboxylic acid 2-{1-Ethyl-1-[4-(2-ethyl-2-hydroxy-butoxy)-3-methyl-phenyl]-propyl}benzo[b]thiophene-6-carboxylic acid methyl ester (0.48 g, 1.02 mmol) is dissolved in MeOH (2 mL) and treated with H2O (0.5 mL) and NaOH (0.20 g, 5.12 mmol). The resulting mixture is heated at a reflux for 2 h, cooled to RT, and stirred overnight. The solution is diluted with H$_2$O (10 mL), adjusted to pH 3-4 using 1 M HCl, and extracted with EtOAc (40 mL). The EtOAc layer is washed with brine (20 mL), dried with MgSO$_4$, filtered, and concentrated to yield the title compound (0.42 g, 0.92 mmol, 89%). $^1$H NMR (CDCl$_3$), δ 0.76 (t, J=7.5 Hz, 6H), 0.95 (t, J=7.5 Hz, 6H), 1.68 (q, J=14.8, 7.5 Hz, 4H), 2.25-2.27 (m, 7H), 3.82 (s, 2H), 6.74 (d, J=8.8 Hz, 1H), 7.05 (d, J=2.3 Hz, 1H), 7.09 (dd, J=8.5, 2.1 Hz, 1H), 7.24 (s, 1H), 7.75 (d, J=8.4 Hz, 1H), 7.96 (dd, J=8.3, 1.7 Hz, 1H), 8.48 (d, J=1.7 Hz, 1H). Exact mass (m/z): calcd. for C$_{27}$H$_{35}$O$_4$S (M+H)$^+$: 454.2; found: 472.3.

Example 23

Preparation of 5-{1-[4-(2-tert-Butyl-[1,3]dioxolan-2-ylmethoxy)-3-methyl-phenyl]-1-ethyl-propyl}-benzo[b]thiophene-2-carboxylic acid ethyl ester

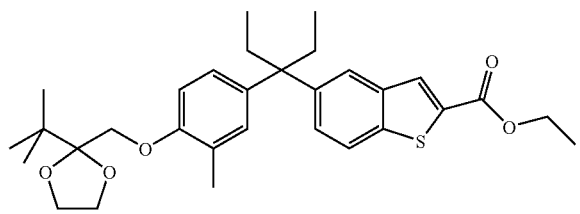

A solution of 5-{1-[4-(3,3-dimethyl-2-oxo-butoxy)-3-methyl-phenyl]-1-ethyl-propyl}-benzo[b]thiophene-2-carboxylic acid ethyl ester (170 mg, 0.354 mmol)) in ethylene glycol (3.0 mL) is treated with BF$_3$-Et$_2$O (2.0 mL). The mixture is stirred at 90° C. for 6 h, cooled to RT, and quenched with water (50 mL). The mixture is extracted with EtOAc (2×20 mL), and the organic layer is concentrated and purified using silica gel column chromatography (10% EtOAc/Hex) to afford the product as an oil (94 mg, 51%).

MS (ES) m/e 542.3 (M+18).

Example 24

Preparation of methanesulfonic acid 2-{1-[4-(3,3-dimethyl-2-oxo-butoxy)-3-methyl-phenyl]-1-ethyl-propyl}-benzo[b]thiophen-5-yl ester

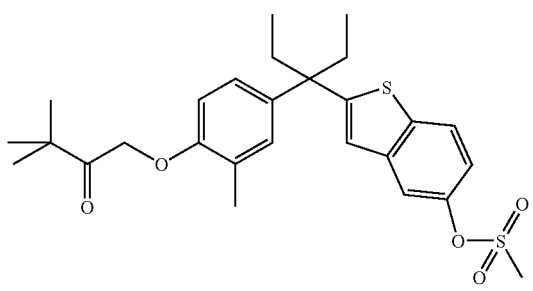

A solution of 1-{4-[1-ethyl-1-(5-hydroxy-benzo[b]thiophen-2-yl)-propyl]-2-methyl-phenoxy}-3,3-dimethyl-butan-2-one (260 mg, 0.612 mmol) in CH$_2$Cl$_2$ (20 mL) at RT is treated with Et$_3$N (0.40 mL) and methanesulfonyl chloride (140 mg, 1.22 mmol). The mixture is stirred for 30 min and quenched with water (1.0 mL). The organic layer is concentrated and purified using silica gel column chromatography (25% EtOAc/Hex) to afford the title compound (190 mg, 62%). NMR (ppm, CDCl$_3$), δ: 7.67 (1 H, d, J=8.8 Hz), 7.59 (1 H, d, J=2.2 Hz), 7.13 (1 H, dd, J=2.2, 8.8 Hz), 7.11 (1 H, s), 7.01-7.04 (2 H, m), 6.51 (1 H, d, J=8.4 Hz), 4.84 (2 H, s), 3.16 (3 H, s), 2.26 (3 H, s), 2.15 (4 H, q, J=7.5 Hz), 1.26 (9 H, s), 0.74 (6H, t, J=7.5 Hz).

MS (ES) m/e 520.3 (M+18).

Example 25

Preparation of enantiomers of 2-{1-ethyl-1-[4-(2-hydroxy-3,3-dimethyl-butoxy)-3-methyl-phenyl]-propyl}-benzo[b]thiophene-6-carboxylic acid

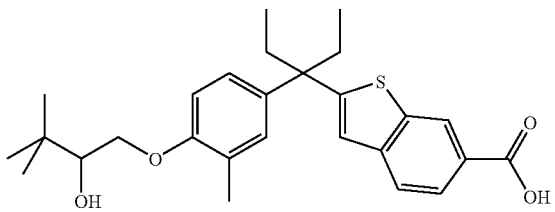

Step A: Preparation of racemic of 2-{1-ethyl-1-[4-(2-hydroxy-3,3-dimethyl-butoxy)-3-methyl-phenyl]-propyl}-benzo[b]thiophene-6-carboxylic acid methyl ester

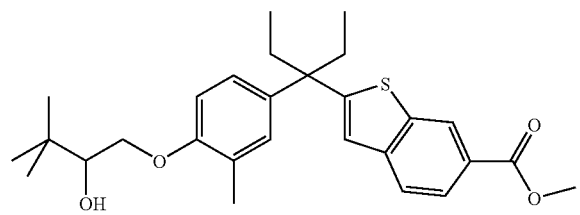

2-{1-[4-(3,3-Dimethyl-2-oxo-butoxy)-3-methyl-phenyl]-1-ethyl-propyl}-benzo[b]thiophene-6-carboxylic acid methyl ester (4.50 g, 9.64 mmol) in THF (100 mL) is reacted with NaBH$_4$ (0.37 g, 9.64 mmol) analogous to Example 2 to obtain the title compound (3.90 g, 86%).

Step B: Preparation of enantiomers of 2-{1-ethyl-1-[4-(2-hydroxy-3,3-dimethyl-butoxy)-3-methyl-phenyl]-propyl}-benzo[b]thiophene-6-carboxylic acid methyl ester A mixture of racemic 2-{1-ethyl-1-[4-(2-hydroxy-3,3-dimethyl-butoxy)-3-methyl-phenyl]-propyl}-benzo[b]thiophene-6-carboxylic acid methyl ester (3.90 g) is chromatographed with Chiralpak AD column to give enantiomer 1, Example QE1 (1.495 g, 38%) and enantiomer 2, Example QE2 (1.489 g, 38%).

Enantiomer 1, Example 25A
HPLC: ChiralPak AD (4.6×150); 60% MeOH/40% ACN/ 0.05% dmea; 0.6 mL/min (flow rate); uv: 287 nm.
Rt=6.0 m.
NMR eq to Step A.
Enantiomer 2, Example 25B
HPLC: ChiralPak AD (4.6×150); 60% MeOH/40% ACN/ 0.05% dmea; 0.6 mL/min (flow rate); uv: 287 nm.
Rt=8.5 m.
NMR eq to Step A.

Step C:

Enantiomer 1 (1.495 g, 3.19 mmol) is hydrolysis analogous to Example 7, step E to provide acid 2290264 (1.44 g, 99%). MS are eq to those in Example 8.

Enantiomer 2 (1.489 g, 3.18 mmol) is hydrolysis analogous to Example 7, step E to provide acid 2290265 (1.44 g, 99%). MS are eq to those in Example 8.

Example 26

D-2-[(2-{1-Ethyl-1-[4-(2-ethyl-2-hydroxy-butoxy)-3-methyl-phenyl]-propyl}-benzo[b]thiophene-6-carbonyl)-amino]-propionic acid methyl ester

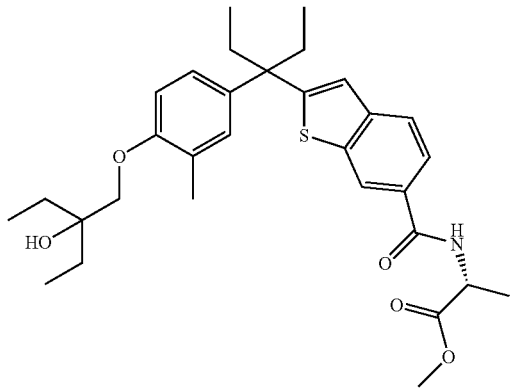

Using the procedure analogous to Example 5, from 2-{1'-ethyl-1-[4-(2-ethyl-2-hydroxy-butoxy)-3-methyl-phenyl]-propyl}benzo[b]thiophene-6-carboxylic acid (example 22) (0.10 g, 0.22 mmol) and D-alanine methyl ester hydrochloride salt (0.034 g, 0.24 mmol), EDCI (0.046 g, 0.24 mmol), HOBt (0.032 g, 0.24 mmol), NEt$_3$ (0.12 mL, 0.88 mmol) and DMF (2 mL) to furnish the titled compound (0.079 g, 0.15 mmol, 66%). LC/MS (m/z): calcd. for $C_{31}H_{41}NO_5S$ (M+H)$^+$: 540.3; found: 540.1.

Example 27

D-2-[(2-{1-Ethyl-1-[4-(2-ethyl-2-hydroxy-butoxy)-3-methyl-phenyl]-propyl}-benzo[b]thiophene-6-carbonyl)-amino]-propionic acid

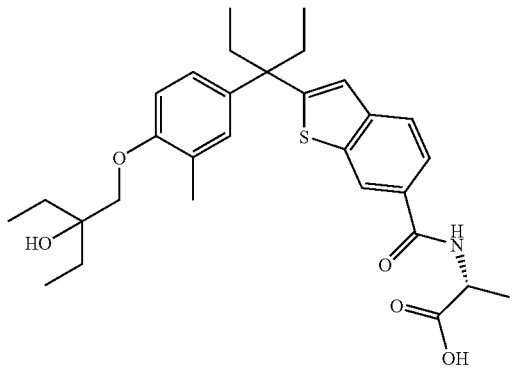

Using the procedure analogous to Example 5, from D-2-[(2-{1-Ethyl-1-[4-(2-ethyl-2-hydroxy-butoxy)-3-methyl-phenyl]-propyl}-benzo[b]thiophene-6-carbonyl)-amino]-propionic acid methyl ester, example 26 (0.079 g, 0.15 mmol) and NaOH (0.03 g, 0.73 mmol) to furnish the titled compound (0.059 g, 0.11 mmol, 79%). LC/MS (m/z): calcd. for $C_{30}H_{39}NO_5S$ (M+H)$^+$: 526.3; found: 526.1.

Example 28

L-2-[(2-{1-Ethyl-1-[4-(2-ethyl-2-hydroxy-butoxy)-3-methyl-phenyl]-propyl}-benzo[b]thiophene-6-carbonyl)-amino]-propionic acid methyl ester

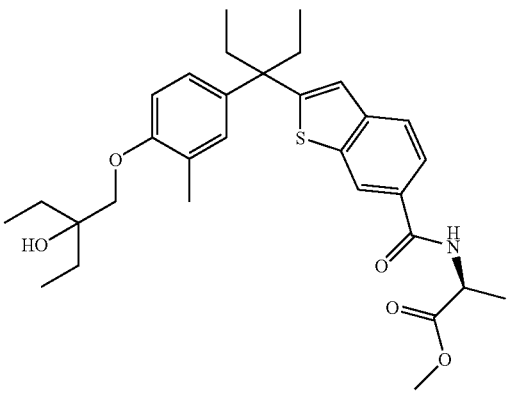

Using the procedure analogous to Example 5, from 2-{1-ethyl-1-[4-(2-ethyl-2-hydroxy-butoxy)-3-methyl-phenyl]-propyl}benzo[b]thiophene-6-carboxylic acid (example 22) (0.10 g, 0.22 mmol) and L-alanine methyl ester hydrochloride salt (0.034 g, 0.24 mmol) EDCI (0.046 g, 0.24 mmol), HOBt (0.032 g, 0.24 mmol), NEt$_3$ (0.12 mL, 0.88 mmol) and DMF (2 mL) to furnish the titled compound (0.10 g, 0.19 mmol, 83%). LC/MS (m/z): calcd. for $C_{31}H_{41}NO_5S$ (M+H)$^+$: 540.3; found: 540.2.

Example 29

L-2-[(2-{1-Ethyl-1-[4-(2-ethyl-2-hydroxy-butoxy)-3-methyl-phenyl]-propyl}-benzo[b]thiophene-6-carbonyl)-amino]-propionic acid

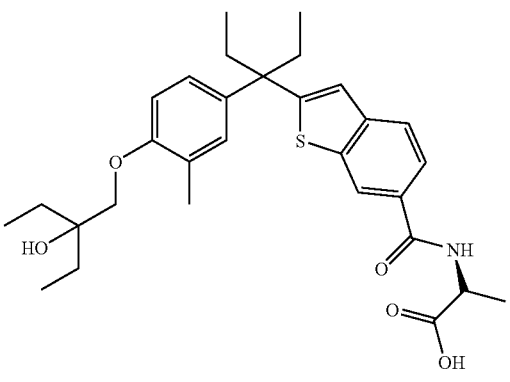

Using the procedure analogous to Example 5, from L-2-[(2-{ 1-ethyl-1-[4-(2-ethyl-2-hydroxy-butoxy)-3-methylphenyl]-propyl}-benzo[b]thiophene-6-carbonyl)-amino]-propionic acid methyl ester, example 28 (0.10 g, 0.19 mmol) and NaOH (0.037 g, 0.93 mmol) to furnish the titled compound (0.092 g, 0.18 mmol, 95%). LC/MS (m/z): calcd. for $C_{30}H_{39}NO_5S$ $(M+H)^+$: 526.3; found: 526.1.

Example 30

2-[(2-{1-Ethyl-1-[4-(2-ethyl-2-hydroxy-butoxy)-3-methyl-phenyl]-propyl}-benzo[b]thiophene-6-carbonyl)-amino]-2-methyl-propionic acid methyl ester

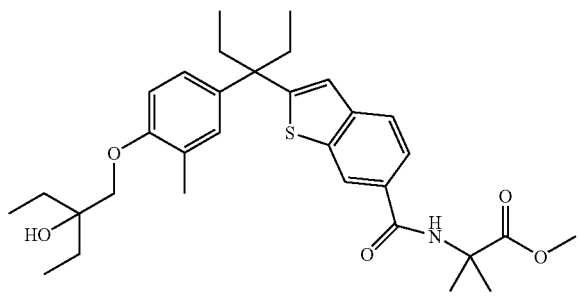

Using the procedure analogous to 5, from 2-{1-ethyl-1-[4-(2-ethyl-2-hydroxy-butoxy)-3-methyl-phenyl]-propyl}benzo[b]thiophene-6-carboxylic acid (example 22) (0.10 g, 0.22 mmol) and α-aminoisobutyric methyl ester hydrochloride salt (0.040 g, 0.24 mmol) EDCI (0.046 g, 0.24 mmol), HOBt (0.032 g, 0.24 mmol), $NEt_3$ (0.12 mL, 0.88 mmol) and DMF (2 mL) to furnish the titled compound (0.10 g, 0.18 mmol, 83%). LC/MS (m/z): calcd. for $C_{32}H_{43}NO_5S$ $(M+H)^+$: 554.3; found: 554.3.

Example 31

2-[(2-{1-Ethyl-1-[4-(2-ethyl-2-hydroxy-butoxy)-3-methyl-phenyl]-propyl}-benzo[b]thiophene-6-carbonyl)-amino]-2-methyl-propionic acid

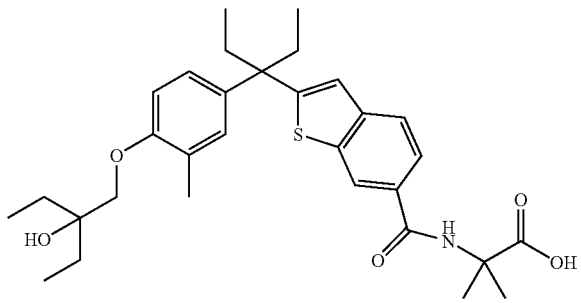

Using the procedure analogous to Example 5, from 2-[(2-{1-Ethyl-1-[4-(2-ethyl-2-hydroxy-butoxy)-3-methyl-phenyl]-propyl}-benzo[b]thiophene-6-carbonyl)-amino]-2-methyl-propionic acid methyl ester, example 30 (0.10 g, 0.18 mmol) and NaOH (0.036 g, 0.90 mmol) to furnish the titled compound (0.088 g, 0.016 mmol, 91%). LC/MS (m/z): calcd. for $C_{31}H_{41}NO_5S$ $(M+H)^+$: 540.3; found: 540.3.

Compounds of the Invention—Salts, Stereoisomers, & Prodrugs:

Salts of the compounds represented by formulae IA, IB, and IC are an additional aspect of the invention. The skilled artisan will also appreciate that the family of compounds of formulae I include acidic and basic members and that the present invention includes pharmaceutically acceptable salts thereof.

In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, ammonium, calcium, magnesium, aluminum, zinc, and the like. Sodium and potassium salts are particularly preferred. Salts are conveniently prepared from the free acid by treating the acid in solution with a base or by exposing the acid to an ion exchange resin. For example, a carboxylic acid substituent on the compound of Formula I may be selected as —$CO_2H$ and salts may be formed by reaction with appropriate bases (e.g., NaOH, KOH) to yield the corresponding sodium and potassium salt.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, choline, clavulanate, citrate, chloride, chloroprocaine, choline, diethanolamine, dihydrochloride, diphosphate, edetate, edisylate, estolate, esylate, ethylenediamine, fluoride, fumarate, gluceptate, gluconate, glutamate, glycolylarsanilate, hexylresorcinate, hydrabamine, bromide, chloride, hydrobromide, hydrochloride, hydroxynaphthoate, iodide, isothionate, lactate, lactobionate, laurate, malate, maleate, malseate, mandelate, meglumine, mesylate, mesviate, methylbromide, methylnitrate, methylsulfate, mucate, napsylate, nitrate, oleate, oxalate, palmitate, pamoate, pantothenate, phosphate, polygalacturonate, procane, salicylate, stearate, subacetate, succinate, sulfate, tannate, tartrate, teoclate, tosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a chiral column may be used such as those sold by Daicel Chemical Industries identified by the trademarks: CHIRALPAK AD, CHIRALPAK AS, CHIRAL- PAK OD, CHIRALPAK OJ, CHIRALPAK OA, CHIRALPAK OB, CHIRALPAK OC, CHIRALPAK OF, CHIRALPAK OG, CHIRALPAK OK, and CHIRALPAK CA-1.

By another conventional method, a racemic mixture may be reacted with a single enantiomer of some other compound. This changes the racemic form into a mixture of diastereomers. These diastereomers, because they have different melting points, different boiling points, and different solubilities can be separated by conventional means, such as crystallization.

The present invention is also embodied in mixtures of compounds of formulae IA, IB, or IC.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy)alkyl esters or ((alkoxycarbonyl)oxy)alkyl esters. Particularly preferred esters to use as prodrugs are; methyl, ethyl, propyl, isopropyl, n-butyl, isobutyl, morpholinoethyl, and N,N-diethylglycolamido.

N,N-diethylglycolamido ester prodrugs may be prepared by reaction of the sodium salt of a compound of Formula IA or IB (in a medium such as dimethylformamide) with 2-chloro-N,N-diethylacetamide (available from Aldrich Chemical Co., Milwaukee, Wis. USA; Item No. 25,099-6).

Morpholinylethyl ester prodrugs may be prepared by reaction of the sodium salt of a compound of Formula IA or IB (in a medium such as dimethylformamide) 4-(2-chloroethyl) morpholine hydrochloride (available from Aldrich Chemical Co., Milwaukee, Wis. USA, Item No. C5,220-3). For example, prodrugs may be prepared by reaction of the sodium salt for a compound of Formula IA or IB with;

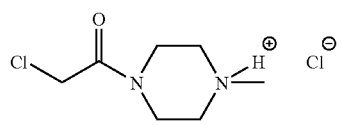

and sodium iodide to provide the ester prodrug pendent group

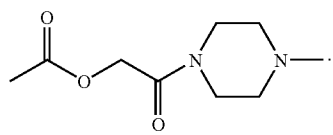

Also, lower alkyl (viz., $C_1$-$C_8$) ester prodrugs may be prepared by conventional means such as reacting the sodium or potassium salt (derived by forming the salt of any acidic compound of the invention; viz., reaction of a base such as KOH with an acidic group such as —$CO_2H$) of a compound of Formula IA or IB with an alkyl iodide such as methyl iodide, ethyl iodide, n-propyl iodide, isopropyl iodide. Typical ester prodrug substituents are

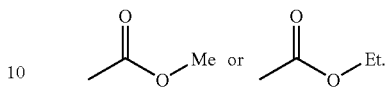

Pharmaceutical Formulations Containing the Novel Compounds of the Invention:

Pharmaceutical formulations of the invention are prepared by combining (e.g., mixing) a therapeutically effective amount of the compound of the invention (compounds of Formula IA, IB, or IC) together with a pharmaceutically acceptable carrier or diluent. The present pharmaceutical formulations are prepared by known procedures using well-known and readily available ingredients.

In making the compositions of the present invention, the compounds of the invention will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the compound. The compounds of the present invention are preferably formulated prior to administration.

The compounds of the invention may also be delivered by suitable formulations contained in a transderm patch. Alternatively, the compounds of the invention may be delived to a patient by sublingual administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided Active ingredient. In table a compound of the invention I is mixed with a carrier having the necessary binding properties in suitable proportions and compacted in the shape and size desired. The powders and tablets preferably contain from about 1 to about 99 weight percent of the compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active Ingredient may be dissolved or suspended in a pharmaceutically acceptable carrier, such as sterile water, sterile organic solvent or a mixture of both. The compounds can often be dissolved in a suitable organic solvent, for instance aqueous propylene glycol. Other compositions can be made by dispersing the finely divided compounds of the invention in aqueous starch or sodium carboxymethyl cellulose solution or in a suitable oil.

Methods of Using the Compounds of the Invention:

Many disease states are benefited by treatment with the compounds of Formula IA, IB, or IC include, but are not limited to:

disease states characterized by abnormal calcium regulation disease states characterized by abnormal cell proliferation disease states characterized by abnormal cell differentiation disease states characterized by abnormal immune response disease states characterized by abnormal dermatological conditions disease states characterized by neurodegenerative condition disease states characterized by inflammation disease states characterized by vitamin D sensitivity disease states characterized by hyperproliferative disorders.

Specific disease states benefited by treatment of the compounds of Formula IA, IB and IC include, but are not limited to:

Acne
Actinic keratosis
Alopecia
Alzheimer's disease
Benign prostatic hyperplasia
Bladder cancer
Bone maintenance in zero gravity
Bone fracture healing
Breast cancer
Chemoprovention of Cancer
Crohn's disease
Colon cancer
Type I diabetes
Host-graft rejection
Hypercalcemia
Type II diabetes
Leukemia
Multiple sclerosis
Myelodysplastic syndrome
Insufficient sebum secretion
Osteomalacia
Osteoporosis
Insufficient dermal firmness
Insufficient dermal hydration
Psoriatic arthritis
Prostate cancer
Psoriasis
Renal osteodystrophy
Rheumatoid arthritis
Scleroderma
Skin cancer
Systemic lupus erythematosus
Skin cell damage from Mustard vesicants
Ulcerative colitis
Vitiligo
Wrinkles Particularly preferred is the treatment of psoriasis and osteoporosis by administration to a mammal (including a human) of a therapeutically effective amount of compounds of Formulae IA, IB or IC. By "pharmaceutically effective amount" it is meant that quantity of pharmaceutical agent corresponding to formulae IA, IB, or IC which prevents, removes or reduces the deleterious effects of a disease state in mammals, including humans.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a pharmaceutically effective amount typically in the range of from about 0.0001 mg/kg/day to about 50 mg/kg/day of body weight of an active compound of this invention. Preferably the dose of compounds of the invention will be from 0.0001 to 5 mg/kg/day of body weight.

Preferably compounds of the invention or pharmaceutical formulations containing these compounds are in unit dosage form for administration to a mammal. The unit dosage form can be a capsule or tablet itself, or the appropriate number of any of these. The quantity of Active ingredient in a unit dose of composition may be varied or adjusted from about 0.0001 to about 1000 milligrams or more according to the particular treatment involved. It may be appreciated that it is necessary to make routine variations to the dosage depending on the age and condition of the patient. Dosage will also depend on the route of administration. The compounds of the invention may be administered by a variety of routes including oral, aerosol, rectal, transdermal, sublingual, subcutaneous, intravenous, intramuscular, and intranasal. Particularly preferred is the treatment of psoriasis with an ointment type formulation containing the compounds of the invention. The ointment formulation may be applied as needed, typically from one to 6 times daily.

Treatment of psoriasis is preferably done with topical application by a formulation in the form of a cream, oil, emulsion, paste or ointment containing a therapeutically effective amount of a compound of the invention. The formulation for topical treatment contains from 0.5 to 0.00005 weight percent, preferably from 0.05 to 0.0005 weight percent, and most preferably from 0.025 to 0.001 of a Active Ingredient.

For example, two semisolid topical preparations useful as vehicles for VDR modulators in treatment and prevention of psoriasis are as follows:

| Polyethylene Glycol Ointment USP (p. 2495) Prepare Polyethylene Glycol Ointment as follows: | |
|---|---|
| Polyethylene Glycol 3350 | 400 g. |
| Polyethylene Glycol 400 | 600 g. |
| To make | 1000 g. |

Heat the two ingredients on a water bath to 65C. Allow to cool, and stir until congealed. If a firmer preparation is desired, replace up to 100 g of the polyethylene glycol 400 with an equal amount of polyethylene glycol 3350.

| Hydrophilic Ointment USP (p. 1216) Prepare Hydrophilic Ointment as follows: | |
|---|---|
| Methylparaben | 0.25 g. |
| Propylparaben | 0.15 g. |
| Sodium Lauryl Sulfate | 10 g. |

-continued

| Hydrophilic Ointment USP (p. 1216) Prepare Hydrophilic Ointment as follows: | |
|---|---|
| Propylene Glycol | 120 g. |
| Stearyl Alcohol | 250 g. |
| White Petrolatum | 250 g. |
| Purified Water | 370 g. |
| To make about | 1000 g. |

The Stearyl Alcohol and White Petrolatum are melted on a steam bath, and warmed to about 75 C. The other ingredients, previously dissolved in the water are added, warmed to 75 C, and the mixture stirred until it congeals.

For each of the above formulations the Active Ingredient is added during the heating step in an amount that is from 0.5 to 0.00005 weight percent, preferably from 0.05 to 0.0005 weight percent, and most preferably from 0.025 to 0.001 weight percent of the total ointment weight. (Source:— United States Pharmacopoeia 24, United States Pharmacopeial Convention, 1999)

Conventional therapy for osteoporosis includes; (i) estrogens, (ii) androgens, (iii) calcium supplements, (iv) vitamin D metabolites, (v) thiazide diuretics, (vi) calcitonin, (vii) bisphosphonates, (viii) SERMS, and (ix) fluorides (see, Harrison's Principles of Internal Medicine, 13$^{th}$ edition, 1994, published by McGraw Hill Publ., ISBN 0-07-032370-4, pgs. 2172-77; the disclosure of which is incorporated herein by reference.). Any one or combination of these conventional therapies may be used in combination with the method of treatment using compounds of Formulae IA, IB, or IC as taught herein. For example, in a method of treating osteoporosis, the vitamin D receptor modulator compounds of the invention may be administered separately or simultaneously with a conventional therapy. Alternatively, the vitamin D receptor modulator compounds of the invention may be combined with conventional therapeutic agents in a formulation for treatment of osteoporosis such as set out below:

A formulation for treating osteoporosis comprising:
  Ingredient (A1): a vitamin D receptor modulator represented by formula (IA), (IB), or (IC), or a pharmaceutically acceptable salt or prodrug derivative thereof;
  Ingredient (B1):
    one or more co-agents that are conventional for treatment osteoporosis selected from the group consisting of:
      a. estrogens,
      b. androgens,
      c. calcium supplements,
      d. vitamin D metabolites,
      e. thiazide diuretics,
      f. calcitonin,
      g. bisphosphonates,
      h. SERMS, and
      i. fluorides.
  Ingredient (C1): optionally, a carrier or diluent.

Typically useful formulations are those wherein the weight ratio of (A1) to (B1) is from 10:1 to 1:1000 and preferably from 1:1 to 1:100.

Combination Therapy for Psoriasis:

Conventional therapy for psoriasis includes topical glucocorticoids, salicylic acid, crude coal tar, ultraviolet light, and methotrexate (see, Harrison's Principles of Internal Medicine, 13$^{th}$ edition, 1994, published by McGraw Hill Publ., ISBN 0-07-032370-4, pgs. 2172-77). Any one or combination of these conventional therapies may be used in combination with the method of treatment using compounds of Formulae IA, IB, or IC as taught herein. For example, in a method of treating osteoporosis, the vitamin D receptor modulator compounds of the invention (e.g., as defined by Formulae IA, IB or IC) may be topically administered separately or simultaneously with a conventional therapy. Alternatively, the vitamin D receptor modulator compounds of the invention may be combined with conventional therapeutic agents in a topically applied formulation for treatment of osteoporosis such as set out below:

A formulation for treating psoriasis comprising:
  Ingredient (A2): a vitamin D receptor modulator represented by formula (IA), (IB), or (IC), or a pharmaceutically acceptable salt or prodrug derivative thereof;
  Ingredient (B2):
    one or more co-agents that are conventional for treatment psoriasis selected from the group consisting of:
      a. topical glucocorticoids,
      b. salicylic acid, or
      c. crude coal tar.
  Ingredient (C2): optionally, a carrier or diluent.

Typically useful formulations are those wherein the weight ratio of (A2) to (B2) is from 1:10 to 1:100000 and preferably from 1:100 to 1:10000.

Experimental Results:

TABLE 1

Summary of Experimental Results

| Test Cmpd.[1] | RXR-VDR heterodimer[2] $EC_{50}$ (nM) | VDR $EC_{50}$ (nM) (Caco-2 cells)[3] | OCN Promoter[4] $EC_{50}$ (nM) | Mouse Hypercal[5] μg/Kg/d |
|---|---|---|---|---|
| Ex. 1 | 234/14 | 432 | 2/1 | <300 |
| Ex. 2 | 30 | 411 | 1 | |
| Ex. 3 | 442/67 | 869 | 7/168 | |
| Ex. 4 | 401/19 | 555 | 20/15 | |
| Ex. 5 | 2/27 | 342 | 1 | >300 |
| Ex. 6 | 18/0.4 | 331 | 1/0.1 | |
| Ex 7 | 159/9 | 791 | 1 | >300 |
| Ex. 8 | 135/1 | 409 | 0.8/0.3 | |
| Ex. 9 | 959/27 | 1271 | 41/35 | |
| Ex. 10 | 323 | 690 | 24/18 | |
| Ex. 11 | 45 | 299 | 0.2 | >300 |
| Ex. 12 | 19/2 | 137 | 0.3 | |
| Ex. 13 | 488/111 | 994 | 9/28 | >300 |
| Ex 14 | 376/26 | 941 | 6 | |
| Ex 15 | 539/63 | | 20/60 | <1000 |
| Ex 16 | 254/108 | 938 | 19/39 | |
| Ex 17 | 272/51 | 631 | 4/3 | >300 |
| Ex 18 | 242/3 | 748 | 2.4/1.3 | |
| Ex 19 | 114/21 | 815 | 4.7 | >300 |
| Ex 20 | 24 | 314 | 5 | |
| Ex 21 | 134/24 | 708 | 29/48 | >1000 |
| Ex 22 | 458/139 | 1057 | 32/15 | |
| Ex 23 | | | 161 | |
| Ex 24 | 695 | | 215 | |

TABLE 2

Summary of Experimental Results

| Test Cmpd.[1] | Kera. Prolif. $IC_{50}$ (nM) | IL-10. $IC_{50}$ (nM) |
|---|---|---|
| Ex. 1 | 11/23 | 109 |
| Ex. 2 | 1 | 24 |
| Ex. 3 | >1000 | 351 |
| Ex. 4 | | |
| Ex. 5 | 4 | 6 |

TABLE 2-continued

Summary of Experimental Results

| Test Cmpd.[1] | Kera. Prolif. IC$_{50}$ (nM) | IL-10. IC$_{50}$ (nM) |
|---|---|---|
| Ex. 6 | 4 | 4 |
| Ex 7 | 1000 | |
| Ex. 8 | 1 | 15 |
| Ex. 9 | 1000 | |
| Ex. 10 | 573 | |
| Ex. 11 | 2 | 10 |
| Ex. 12 | 1 | |
| Ex. 13 | | |
| Ex 14 | | |
| Ex 15 | | |
| Ex 16 | 384 | |
| Ex 17 | 404 | |
| Ex 18 | 1.8 | 89 |
| Ex 19 | 16 | 149 |
| Ex 20 | 98 | 386 |
| Ex 21 | 162 | |
| Ex 22 | 154 | |
| Ex 24 | 232 | |

TABLE 3 of Experimental Results (comparison compounds)

| Test Cmpd.[1] | RXR-VDR (SaOS-2 cells)[2] EC$_{50}$ (nM) | VDR CTF (Caco-2 cells)[3] EC$_{50}$ (nM) | OCN Promoter[4] EC$_{50}$ (nM) | Mouse Hypercal[5] µg/Kg/d |
|---|---|---|---|---|
| AA | 5.02 | 16 | 5 | 0.06 |
| BB | 10.32 | 169.81 | 8.24 | 20 |
| CC | 2427.7 | | 2680.9 | |
| DD | 109.44 | | 31.1 | 1000 |
| EE | 429.99 | 891.16 | 341.25 | 1000 |
| FF | 3/1 | 57 | 0.28 | |

TABLE 4 of Experimental Results (comparison compounds)

| Test Cmpd.[1] | Kera. Prolif. IC$_{50}$ (nM) | IL-10 IC$_{50}$ (nM) |
|---|---|---|
| AA | 120 | 1.2 |
| BB | 10 | 28 |
| CC | — | — |
| DD | 1060 | |
| EE | | |
| FF | 103 | 0.5 |

Explanation of Table 5 and 6 column numerical superscripts:

1. Test Compound numbers refer to the products of the corresponding Example Nos. that is, compounds within the scope of the invention 2. The control experiments are done with the double letter coded compounds identified as follows:

"AA"=1α,25-dihydroxyvitamin D$_3$

"BB"=3-(4-{1-Ethyl-1-[4-(2-hydroxy-3,3-dimethyl-butoxy)-3-methyl-phenyl]-propyl}-2-methyl-phenoxy)-propane-1,2-diol "CC"=1-(4-{1-[4-(3,3-Dimethyl-2-oxo-butoxy)-3-methyl-phenyl]-cyclohexyl}-2-methyl-phenoxy)-3,3-dimethyl-butan-2-one

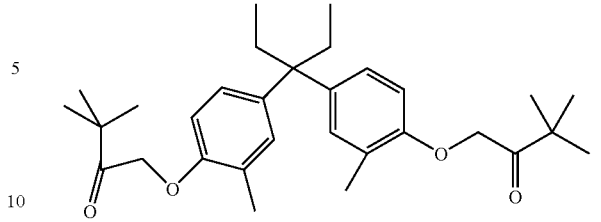

"DD"=compound represented by the formula:
"EE"=compound represented by the formula:

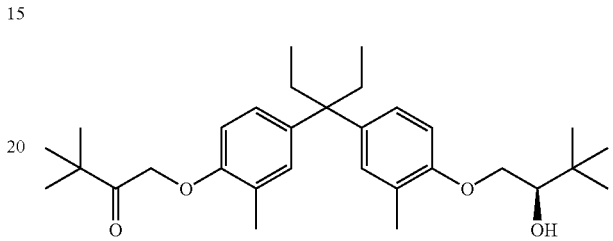

"FF"=calcipotriol (structural formula below):

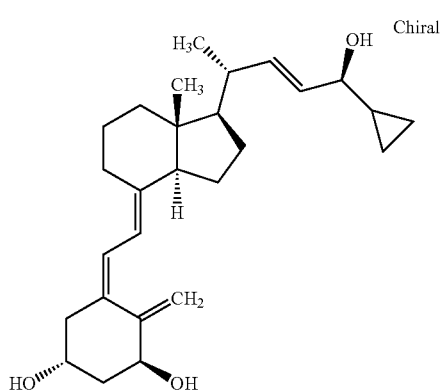

2. The RXR-VDR heterodimerization (SaOS-2 cells) test is described in the "Assay" section of the Description, infra.

3. The VDR CTF (Caco-2 cells) test is described in the "Assay" section of the Description, infra.

4. The OCN Promoter test is described in the "Assay" section of the Description, infra.

5. The Mouse Hypercalcemia test is described in the "Assay" section of the Description, infra.

6. The keratinocyte proliferation assay is described in the "Assay" section of the Description, infra.

7. The IL-10 induction assay is described in the "Assay" section of the Description, infra.

Assay Methods

Use of the Assay Methods:

The evaluation of the novel compounds of the invention for osteoporosis and other related diseases is done using a plurality of test results. The use of multiple assays is necessary since the combined properties of (i) high activity for the vitamin D receptor, and (ii) prevention of hypercalcemia must be achieved to have utility for the methods of treating diseases, which are also, aspects of this invention. Some of the tests described below are believed related to other tests and measure related properties of compounds. Consequently, a compound may be considered to have utility in the practice of the invention if is meets most, if not all, of the acceptance criteria for the above described tests.

The evaluation of the novel compounds of the invention for psoriasis is done using the Keratinocyte Proliferation Assay in combination with other assays that measure inhibition of IL-2 production and stimulation of IL-10 production in peripheral blood mononuclear cells (PBMCs).

Brief Description, Utility and Acceptance Criteria for the Assay Methods:

1. The RXR-VDR Heterodimer Assay:

This assay provides the VDR activity of a test compound. It is desirable to have low EC50 values for a compound in this assay. The lower the EC50 value, the more active the compound will be as a VDR agonist. Desired assay results are EC50 values less than or equal to 600 nM. Preferred assay results are less than 250 nM, and most preferably less than 150 nM.

2. The Caco-2 Cell Co-Transfection Assay:

The Caco-2 cell assay is an indicator for the undesirable condition of hypercalcemia. This co-transfection assay is a surrogate assay for in vivo calcemic activity of VDR ligands. It is desirable to have high EC50 values for a test compound in this assay. The higher the EC50 values for a compound the less calcemic it will be in vivo. Desired assay results are EC50 greater than or equal to 300 nM. Preferred assay results are greater than 1000 nM.

3. The OCN (Osteocalcin) Promoter Assay

The OCN Promoter Assay is an indicator and marker for osteoporosis. Desired assay results are EC50 less than or equal to 325 nM. Preferred assay results are less than 50 nM.

4. The Mouse Hypercalcemia Assay

The Mouse Hypercalcemia Assay is a six day hypercalcemia test for toxicity and selectivity. Acceptable test results are levels greater than 300 µg/kg/day. Preferred assay results are levels greater than 1000 µg/kg/day.

5. The Keratinocyte Proliferation Assay

This Assay is indicative for the treatment of psoriasis. An acceptable test result is IC50 value of less than or equal to 300 nM. Preferred assay results are IC50 values of less than 100 nM.

6. The IL-10 Induction Assay

This is an in vitro efficacy assay for psoriasis, abscess and adhesion. Psoriasis involves both keratinocytes and immune cells. IL-10 is a unique cytokine because it is anti-inflammatory and immunosuppressive. This assay tells us whether a VDRM is able to function as an agonist in PBMCs (primary blood mononuclear cells) or not. A lower EC50 value is desirable in this assay since a compound with a lower EC50 value will be a better agonist in PBMCs. An acceptable test result is an EC50 value of less than 200 nM. Preferred assay results are EC50 values of less than 100 nM.

7. Other Compound Assay Standards

An alternative measure of the therapeutic index (bone efficacy vx. Hypervcalcemia) of compounds of the invention for treatment of osteoporosis is a numerical ratio calculated as follows:

Dose Threshold needed to induce hypercalcemia divided by Dose Threshold needed for bone efficacy An alternative measusre of the therapeutic index (in vivo keratinocyte proliferation vs. hypercalcemia) of compounds of the invention for treatment of psoriasis is a numerical ratio calculated as follows:

Dose Threshold needed to induce hypercalcemia divided by Dose Threshold needed to induce keratinocyte proliferation For the above ratios, Dose Thresholds are determined from dose response curve data.

8. The CaT1 (Calcium Transporter 1) Assay

The CaT1 Assay is an indicator for the undesirable condition of hypercalcemia. The higher the EC50 values for a compound the less calcemic it will be in vivo. Desired assay results are EC50 greater than or equal to 500 nM. Preferred assay results are greater than 1000 nM.

Details of the Assay Methods:

(1) Materials and Method for RXR-VDR Heterodimerization Assay:

Transfection Method:
FuGENE 6 Transfection Reagent (Roche Cat # 1 814 443)
Growth Media:
D-MEM High Glucose (Gibco BRL Cat # 11054-020), 10% FBS, 1% antibiotic-antimycotic (Ab-Am)
FBS heat inactivated (Gibco BRL Cat # 10092-147)
Ab-Am (Gibco BRL Cat # 15240-062)
Cells:
Grow SaOs-2 cells in T-152 $cm^2$ culture flasks in growth media.
Keep the density at $5-6 \times 10^5$ cells/ml
Passage cells 1:3 twice a week
Add Trypsin EDTA (Gibco BRL Cat # 25300-020)and incubate
Resuspend cells in plating media and transfer into growth media.
Wash Media:
HBSS Low Glucose Without Phenol Red (Gibco BRL Cat # 14175-095), 1% Ab-Am
Plating Media:
D-MEM Low Glucose Without Phenol Red (Gibco BRL Cat # 11054-020), 1% Ab-Am D-MEM
Stripped FBS (Hyclone Cat# SH30068.03 Lot # AHM9371)
Ab-Am
Transfection/Treatment Media:
D-MEM Low Glucose Without Phenol Red only
T-152 $cm^2$ Culture Flask:
Use Corning Coastar T-152 $cm^2$ culture flask (Cat # 430825) to grow the cells
Flat well Plates:
Use well plate to plate cells
Use Deep well plate sterile to make up treatment media.
Luciferase Assay Reagent:
Use Steady-Glo Luciferase Reagent from Promega (Cat # E2550) Consists of:
a. E2533 Assay Substrate, lyopholized product and
b. E2543 Assay Buffer.
Thaw at room temperature
Store
Cell Harvesting
Aspirate media from culture flask, rinse cells with HBSS and aspirate.
Add trypsin and incubate.
When cells appear detached, resuspend cells in growth media.

Transfer into a new flask with fresh growth media for passaging the cells.
Plate well plates and two extra plates
A. Cell Count
Mix the cell suspension using pipette
Use Hematocytometer to count the cells
Load cell suspension onto the hemocytometer chamber
Count cells.
Plate Seeding:
Use plating media 10% Stripped FBS in D-MEM Low Glucose, Without Phenol Red, 1% Ab-Am
Plate 14 plates @ 165 µl/well.
In sterile flask add cell suspension to plating media.
Mix.
Add cells/well.
Place the cells in the incubator.
Cells should be about 75% confluent prior to transfection.

DAY 2: Transfection

Step 1: DNA and Media
Add plain DMEM media to tubes for mixing the DNA
Add the Reporter gene pFR-LUC
Add the Ga14-RXR-DEF and VP16-VDR-LBD Step 2: FuGENE and Media
Prepare plain DMEM media in a ubes for mixing FuGENE
Add FuGENE 6 Transfection Reagent
Incubate Step 3: FuGENE, DNA and Media Complex
Add FuGENE Media complex from step 2 to DNA Media complex from step 1
Incubate Step 4: FuGENE, DNA and Media Complex to-well plate
Add FuGENE-DNA-Media complex from step 3 to each plate
Incubate.

Day 3: Dosing
Treatment preparation
Allow for transfection time
Make a stock solution of the compounds in DMSO
Vortex until all the compounds has been dissolved.
Further dilute in D-MEM (Low Glucose—With out Phenol Red)
Add compounds in quadruplicate to give final volume
Incubate.

Day 4: Luciferase Assay
Read the plates after drug treatment
Remove part of media from all the wells and leave remainder
Add Steady-Glo Luciferase Reagent mixture/wells
Incubate
Count each well using a Luminescence counter, Top Count NXT by Packard
Set a delay between plates to reduce the background.

(2) Materials and Method for the Caco-2 Cell Assay:

Caco-2 cells, grown in phenol red free, DMEM (Invitrogen, Carlsbad, Calif.) containing 10% charcoal-stripped FCS (Hyclone, Logan, Utah), were transfected with Fugene 6 reagent (Roche Diagnostics, Indianapolis, Ind.). Cells (5000/well) were plated 18 h before transfection in a 96 well plate. The Cells were transfected with Ga14-responsive reporter pFRLuc (150 ng, Stratagene, La Jolla Calif.) and the receptor expression vector pGa14-VDR-LBD (10 ng), along with Fugene 6 reagent (0.2 µl/well). The DNA-Fugene complex was formed by incubating the mixture for 30 min at room temperature. The cells were transfected in triplicate for 5 h, and treated with various concentrations of VDR ligands (form 0.01 nM to 10,000 nM concentration range) 18 h post-transfection. The luciferase activity was quantified using Steady-Glo reagent kit (Promega, Madison, Wis.) as per manufacturer's specifications.

(3) Materials and Method for the OCN Promoter Assay:

The activation of osteocalcin by VDR ligands was evaluated in a rat osteoblast-like cell line RG-15 (ROS 17/2.8) stably expressing rat osteocalcin promoter fused with luciferase reporter gene. The stable cell lines were established as reported before (Activation of Osteocalcin Transcription involves interaction of protein kinase A- and Protein kinase C-dependent pathways. Boguslawski, G., Hale, L. V., Yu, X.-P., Miles, R. R., Onyia, J. E., Santerre R. F., Chandrasekhar, S. J Biol. Chem. 275, 999-1006, 2000). Confluent RG-15 cells maintained in DMEM/F-12 medium (3:1) containing 5% FBS, 300 µg/ml G418 and at 37° C. under 5% $CO_2$/95% air atmosphere were trypsinized (0.25% trypsin) and plated into white opaque 96-well cell culture plates (25000 cells/well). After 24 hr, cells (in DMEM/F-12 medium+2% FBS) were treated with various concentrations of compounds, dissolved in DMSO. The final DMSO concentration remained at 0.01% (v/v). After 48 hr treatment, the medium was removed, cells were lysed with 50 µl of lysis buffer (From Luciferase reporter assay system, Roche Diagnostics, Indianapolis, Ind.) and assayed for luciferase activity using the Luciferase Reporter Gene Assay kit from Boehringer Mannheim as per manufacturer's specifications.

(4) Materials and Method for the Mouse Hypercalcemia Assay:

Weanling, virus-antibody-free, five to six weeks old female DBF mice (Harlan, Indianapolis, Ind.) are used for all the studies. Animals are allowed to acclimate to local vivarium conditions for 2 days. Mice are maintained on a 12 hr light/dark cycle at 22° C. with ad lib access to food (TD 5001 with 1.2% Ca and 0.9%P, Teklad, Madison, Wis.) and water. The animals then are divided into groups with 4-5 mice per group. Different doses of test compounds prepared in 10% Ethanol and 90% sesame oil are administered to mice orally via gavage for 6 days. $1\alpha$-$25(OH)_2D_3$ 0.5 µg/kg/d was also given to one group of mice as the positive control. Serum ionized calcium is evaluated at 6 hours after the last dosing under isoflurane anesthesia by Ciba-Corning Ca++/PH Analyzer, (Model 634, Chiron Diagnostics Corp., East Walpole, Mass.). Raw data of group differences is assessed by analysis of variance (ANOVA) using Fisher's protected least significant difference (PLSD) where the significance level was $P<0.05$.

(5) The Keratinocyte Proliferation Assay:

KERtr cells (Human skin keratinocyte transformed with a retrovirus vector, obtained from ATCC) were plated in 96-well flat-bottomed plates (3000 cells/well) in 100 µl keratinocyte serum free medium supplemented with bovine pituitary extract in the absence of EGF (Life Technologies, Rockville, Md.) and incubated at 37° C. for two days. The cells were treated with various concentrations of VDR ligands (ten-fold serial dilution from 10,000 nM to 0.1 nM in triplicate), dissolved in 100 µl keratinocyte serum free medium supplemented with bovine pituitary extract in the absence of EGF and incubated at 37° C. for 72 hr. BrdU (5-bromo-2'-deoxyuridine) incorporation was analyzed as a measure of DNA replication (Cell proliferation ELISA kit, Roche Diagnostics, Indianapolis, Ind.) and absorbance was measured at 405 nm. Potency values ($IC_{50}$) values were determined as the concentration (nM) of compound that elicited a half-maximal response.

(6) Materials and Method for human IL-10 Induction Assay:

Isolation of peripheral blood mononuclear cells (PBMCs):
A. Collect 50 ml of human blood and dilute with media, RPMI-1640.
B. Prepare sterile tubes with ficol.
C. Add diluted blood to tubes.
D. Centrifuge.
E. Discard the top layer and collect the cells from middle layer.
F. Divide all cells into four tubes and add media.
G. Centrifuge.
H. Aspirate off media and resuspend.
I. Collect all cells
J. Centrifuge. at 1200 rpm for 10 minutes.
K. Resuspend in RPMI-1640 with 2% FBS and count cells
Stimulation of PBMC:
L. Prepare TPA in DMSO.
M. Dissolve PHA in water.
N. Plate TPA/PHA treated PBMCs in well plates.
O. Incubate.
Treatment:
P. Prepare all compound dilutions in plain RPMI-1640 media.
Q. Add diluted compound.
R. Incubate.
Sample Collection and assay:
S. Remove all the cells by centrifugation and assay the supernatant for IL-10 by immunoassay.
T. Perform IL-10 assay using anti-human IL-10 antibody coated beads, as described by the manufacturer (Linco Research Inc., St. Charles, Mo.).

(8) CaT1 Assay

Human colon carcinoma, Caco-2 cells, maintained in DMEM (high glucose with 25 mM Hepes buffer; Invitrogen, Carlsbad, Calif.) supplemented with 10% fetal bovine serum (Invitrogen, Carlsbad, Calif.), are plated at 5500 cell per well in a 96-well plate in a total volume of 100 μl/well. The cells are kept in the 96-well plate for 6 days to differentiate them to small intestinal cells that express the calcium transporter, CaT1. On day 3 after plating, old media is removed and replaced with fresh media (150 μl/well). On day 6 the old media is removed and the cells are kept in treatment media (180 μl/well) that contained 10% charcoal stripped fetal bovine serum (Hyclone, Logan, Utah) in DMEM (low glucose, without phenol red; Invitrogen, Carlsbad, Calif.). The cells are treated with various concentrations of VDR ligands (from 0.01 nM to 10,000 nM concentration range) prepared in treatment media (20 μl/well). Twenty hours post-treatment, total RNA is prepared by RNeasy 96 method as described by the manufacturer (Qiagen, Valencia, Calif.). The RNA is reverse transcribed and amplified for human CaT1 and GAPDH (control) messages by quantitative RT-PCR using ABI PRISM 7900HT Sequence Detection System according to manufacturer's instructions (Applied Biosystems, Foster City, Calif.). Optimized primer pairs and probes for human CaT1 and GAPDH genes are obtained commercially (Applied Biosystems, Foster City, Calif.). Each 20 μl quantitative RT-PCR reaction in a 384-well Taqman PCR plate consists of forward and reverse primers (900 nM), Taqman probe (200 nM), total RNA (4 μl form each well of the 96-well culture plate) and 10 μl of Taqman Universal PCR Master Mix (Roche Diagnostics, Indianapolis, Ind.). Reactions are incubated at 48° C. for 30 minutes, followed by 10 minutes at 95° C. and subjected to 40 cycles of PCR (95° C. for 15 seconds followed by 60° C. for 1 minute). GAPDH is used as an internal control and its primer and probe set are obtained commercially (Applied Biosystems, Foster City, Calif.).

We claim:

1. A compound or a pharmaceutically acceptable salt thereof represented by a formula below:

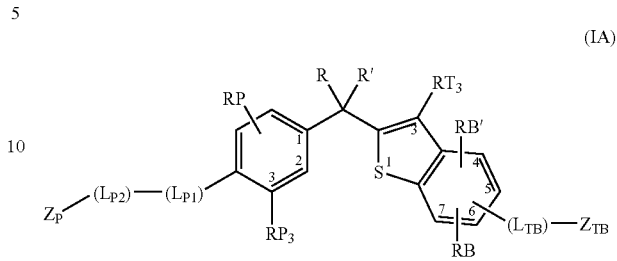

(IA)

wherein
$R$ and $R'$ are independently $C_1$-$C_5$ alkyl, or together R and R' form a carbocyclic ring having from 3 to 8 carbon atoms;
$RP_3$ is hydrogen, or $C_1$-$C_5$ alkyl;
$(L_{P1})$ is —$(CH_2)_m$—O—;
$(L_{P2})$ is

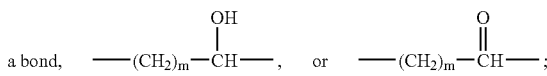

is where m is 0, 1, or 2;
$Z_P$ is a branched $C_3$-$C_5$ alkyl or 1-ethyl-1-hydroxypropyl;
$Z_{TB}$ is selected from
—O—SO$_2$—($C_1$-$C_5$ alkyl,)
—CO$_2$H,
—CO$_2$Me,
—CO$_2$Et,
—C(O)NH$_2$,
—C(O)NMe$_2$,
—C(O)NH—CH$_2$—C(O)OH,
—C(O)NH—CH$_2$—C(O)OMe,
—C(O)NH—CH$_2$—C(O)OEt,
—C(O)NH—CH$_2$—C(O)OiPr,
—C(O)NH—CH$_2$—C(O)OtBu,
—C(O)NH—CH(Me)-C(O)OH,
—C(O)NH—CH(Me)-C(O)OMe,
—C(O)NH—CH(Me)-C(O)OEt,
—C(O)NH—CH(Me)-C(O)iPr,
—C(O)NH—CH(Me)-C(O)tBu,
—C(O)NH—CH(Et)-C(O)OH,
—C(O)NH—C(Me)$_2$-C(O)OH,
—C(O)NH—C(Me)$_2$-C(O)OMe,
—C(O)NH—C(Me)$_2$-C(O)OEt,
—C(O)NH—C(Me)$_2$-C(O)iPr,
—C(O)NH—C(Me)$_2$-C(O)tBu,
provided that -($L_{TB}$)-$Z_{TB}$ is substituted at either the 5 or 6 position of the benzothiophene ring.

2. The compound of claim 1, or a pharmaceutically acceptable salt thereof,
wherein
R and R' are independently methy or ethyl;
$RP_3$ is hydrogen, methyl, or ethyl; and
$(L_{P2})$ is a bond or —CH(OH)—.

3. A compound according to claim 1 represented by formulae below or a pharmaceutically acceptable salt thereof:

C7)
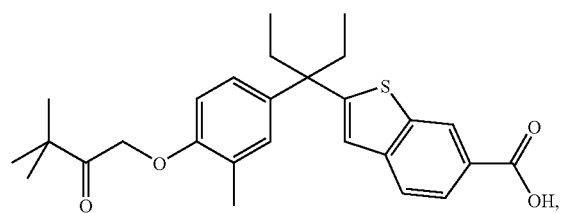
C8)
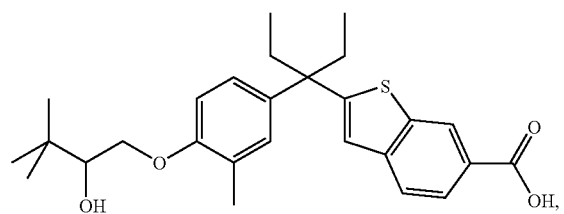
C9)
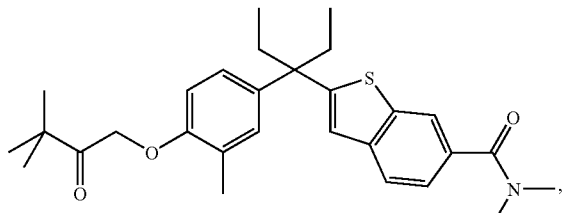
C10)
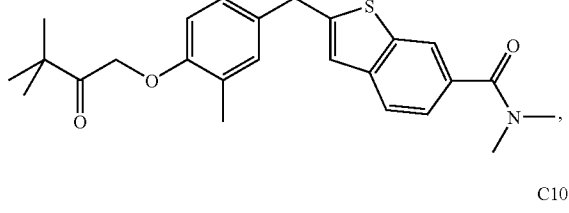
C11)
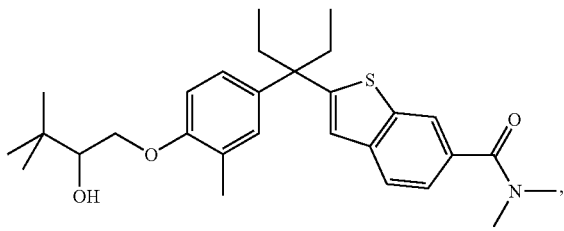
C12)
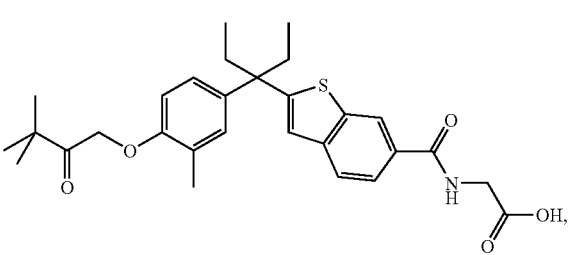
-continued
C17)
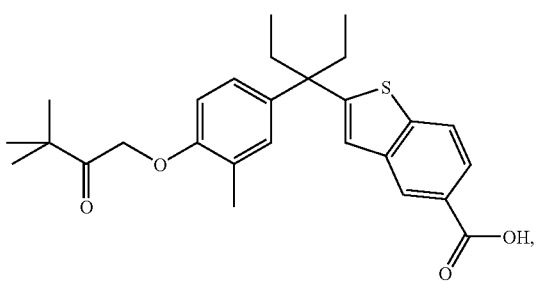
C18)
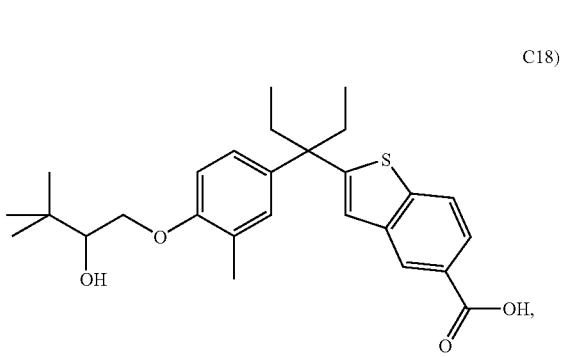
C19)
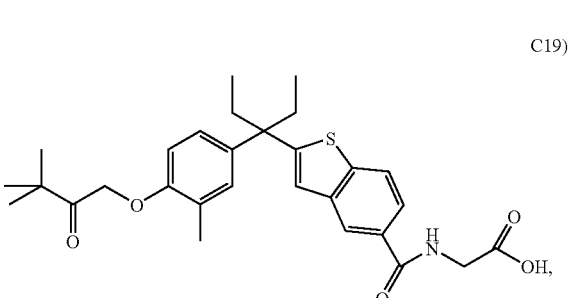
C20)
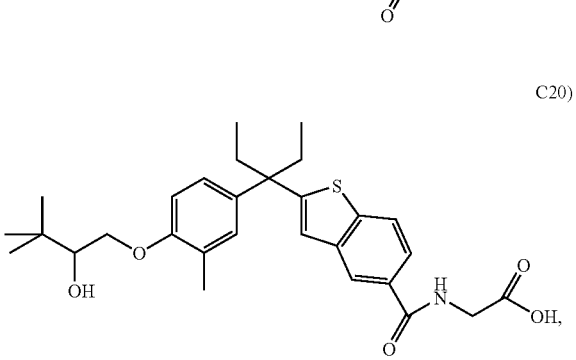
C21)
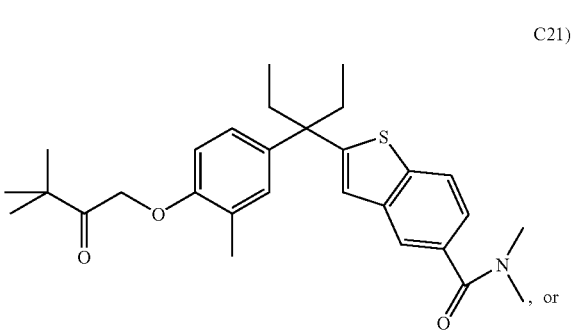, or

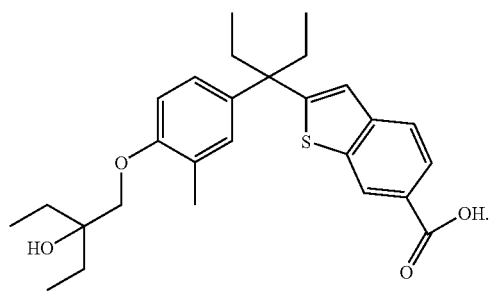

4. The compound according to claim 1 represented by the structural formula AA or a pharmaceutically acceptable salt thereof:

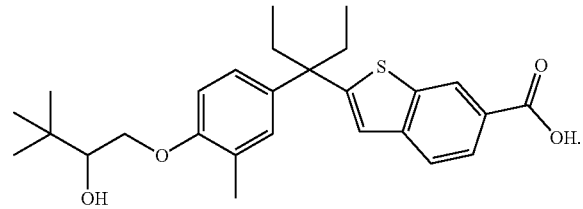

5. A compound according to claim 1 or a pharmaceutically acceptable salt thereof wherein said compound is selected from

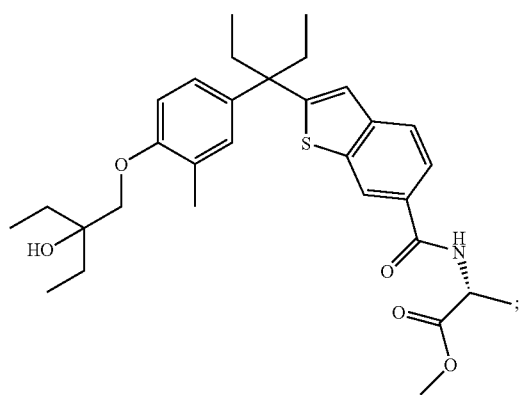

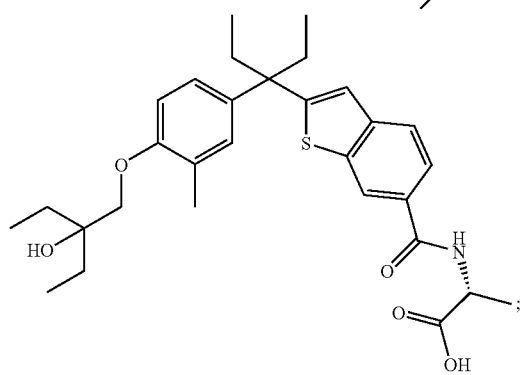

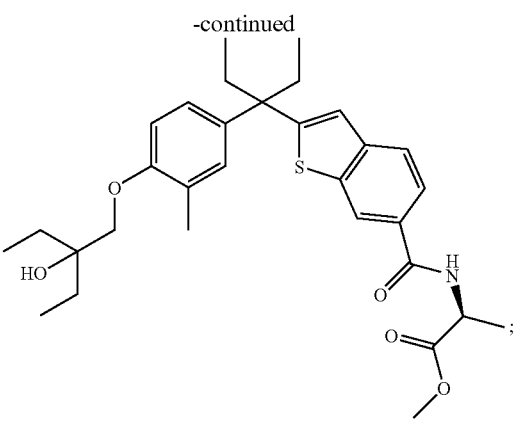

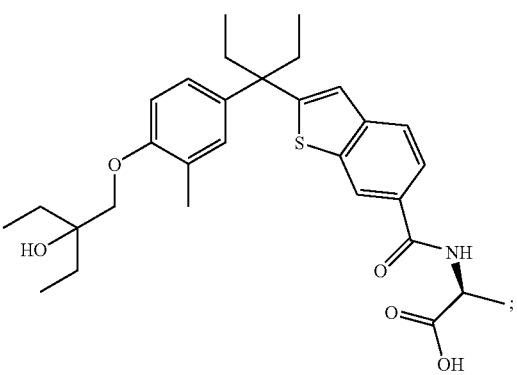

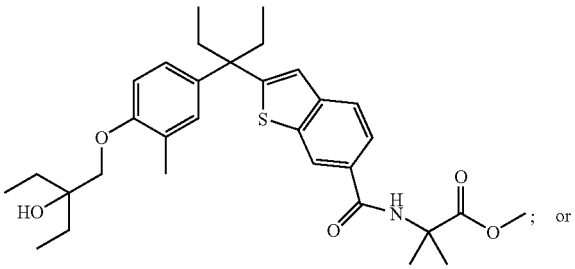

6. A compound according to claim 1 wherein the pharmaceutically acceptable salt is a sodium or potassium salt.

7. A pharmaceutical formulation comprising the compound according to claim 1 together with a pharmaceutically acceptable carrier or diluent.

8. A method of treating a mammal to alleviate the pathological effects of Osteoporosis or Psoriasis, wherein the method comprises administering a pharmaceutically effective amount of at least one compound according to claim 1 or a pharmaceutically acceptable salt thereof.

9. The method of claim 8 for the treatment of psoriasis.

10. The method of claim 8 for the treatment of osteoporosis.

11. A compound of according to claim 1, or a pharmaceutically acceptable salt thereof,
R and R' are each ethyl;
$RP_3$ is methyl; and
$(L_{P2})$ is a —C(O)— or —CH(OH)—.

12. A compound according to claim 1 wherein $Z_{TB}$ includes a carboxylic acid group functionalized as a N,N-diethylglycolamido ester or morpholinylethyl ester.

13. A compound according to claim 4 wherein the pharmaceutically acceptable salt is a sodium or potassium salt.

14. A pharmaceutical formulation comprising the compound according to claim 4 together with a pharmaceutically acceptable carrier or diluent.

15. A method of treating a mammal to alleviate the pathological effects of Osteoporosis or Psoriasis, wherein the method comprises administering a pharmaceutically effective amount of at least one compound according to claim 4 or a pharmaceutically acceptable salt thereof.

16. The method of claim 15 for the treatment of psoriasis.

17. The method of claim 15 for the treatment of osteoporosis.

* * * * *